(12) United States Patent
Rotthier et al.

(10) Patent No.: US 9,828,638 B2
(45) Date of Patent: Nov. 28, 2017

(54) MUTATIONS IN SPTLC2 GENE ASSOCIATED WITH SENSORY NEUROPATHY

(75) Inventors: Annelies Rotthier, Olen (BE); Vincent Timmerman, Broechem-Ranst (BE); Michaela Auer-Grumbach, Graz (AT); Thorsten Hornemann, Zürich (CH)

(73) Assignees: VIB VZW, Gent (BE); Universiteit Antwerpen, Antwerp (BE); University of Zurich, Zurich (CH); Medical University of Graz, Graz (AT)

( * ) Notice: Subject to any disclaimer, the term of this patent is extended or adjusted under 35 U.S.C. 154(b) by 423 days.

(21) Appl. No.: 13/823,080

(22) PCT Filed: Sep. 19, 2011

(86) PCT No.: PCT/EP2011/066212
§ 371 (c)(1),
(2), (4) Date: May 28, 2013

(87) PCT Pub. No.: WO2012/035164
PCT Pub. Date: Mar. 22, 2012

(65) Prior Publication Data
US 2013/0236894 A1 Sep. 12, 2013

Related U.S. Application Data

(60) Provisional application No. 61/403,619, filed on Sep. 17, 2010.

(30) Foreign Application Priority Data

Sep. 17, 2010 (GB) .................................. 1015581.0

(51) Int. Cl.
*C12Q 1/68* (2006.01)
(52) U.S. Cl.
CPC ..... *C12Q 1/6883* (2013.01); *C12Q 2600/156* (2013.01)
(58) Field of Classification Search
None
See application file for complete search history.

(56) References Cited

FOREIGN PATENT DOCUMENTS

WO WO 2011/089146 A1 7/2011
WO WO 2012/035164 A1 3/2012

OTHER PUBLICATIONS

Ss48420144 (for r534830263, dbSNP, NCBI, NLM, 2005).*
Dawkins et al; Neuromuscular Disorders, vol. 12, pp. 656-658, 2002.*
International Search Report PCT/EP2011/066212, dated Jan. 18, 2012.
Bejaouii et al., SPTLC1 is mutated in hereditary sensory neuropathy, type I, Nature Publishing Group, http://genetics.nature.com nature genetics, dated Mar. 2001, pp. 261-262, vol. 27.
Dawkins et al., Mutations in SPTLC1, encoding serine palmitoyltransferase, long chain base subunit-1, cause hereditary sensory neuropathy type I, Nature Publishing Group, http://genetics.nature.com nature genetics, dated Mar. 2001, pp. 309-312, vol. 27.
Dawkins et al., Exclusion of serine palmitoyltransferase long chain base subunit 2 (SPTLC2) as a common cause for hereditary sensory neuropathy, Neuromuscular Disorders, www.elsevier.com/locate/nmd dated 2002, pp. 656-658, vol. 12.
Gable, et al., Mutations in the Yeast LCB1 and LCB2 Genes, Including Those Corresponding to the Hereditary Sensory Neuropathy Type I Mutations, Dominantly Inactivate Serine Palmitoyltransferase, The Journal of Biological Chemistry, dated Mar. 22, 2002, pp. 10194-10200, vol. 277, No. 12.
Houlden et al., Clinical, pathological and genetic characterization of hereditary sensory and autonomic neuropathy type I (HSAN I), Brain, dated 2006, pp. 411-425, vol. 129.
Linn et al., Functional characterization of the promoter for the mouse SPTLC2 gene, which encodes subunit 2 of serine palmitoyltransferase, FEBS Letters, dated 2006, pp. 6217-6223, vol. 580.
Monaghan et al., Mutations in the Lcb2p subunit of serine palmitoyltransferase eliminate the requirement for the TSC3 gene in *Saccharomyces cerevisiae*, Yeast, Published online in Wiley InterScience (www.interscience.wiley.com), dated 2002, pp. 659-670, vol. 19.
Rotthier et al., Genes for hereditary sensory and autonomic neuropathies: a genotype—phenotype correlation, Brain, dated 2009, pp. 2699-2711, vol. 132.
Rotthier et al., Mutations in the SPTLC2 Subunit of Serine Palmitoyltransferase Cause Hereditary Sensory and Autonomic Neuropathy Type I, The American Journal of Human Genetics, dated Oct. 8, 2010, pp. 513-522, vol. 87.
Rotthier et al., Characterization of Two Mutations in the SPTLC1 Subunit of Serine Palmitoyltransferase Associated with Hereditary Sensory and Autonomic Neuropathy Type I, Human Mutation, Mutation in Brief 32: E2211-E2225, dated Jan. 31, 2011.
XP-002665770, http://ibis.internal.epo.org/exam/dbfetch.jsp?id=GENESEQN:ABC43244 dated Feb. 21, 2002.

* cited by examiner

*Primary Examiner* — Jehanne Sitton
(74) *Attorney, Agent, or Firm* — Foley & Lardner LLP

(57) ABSTRACT

Described are methods and kits for identifying a subject at risk of, or having, a sensory neuropathy related disease, such as sensory neuropathies. In particular, the disclosure is based on the determination of mutations in the SPTLC2 gene causing sensory neuropathies.

8 Claims, 8 Drawing Sheets

FIGURE 2 (Continued)
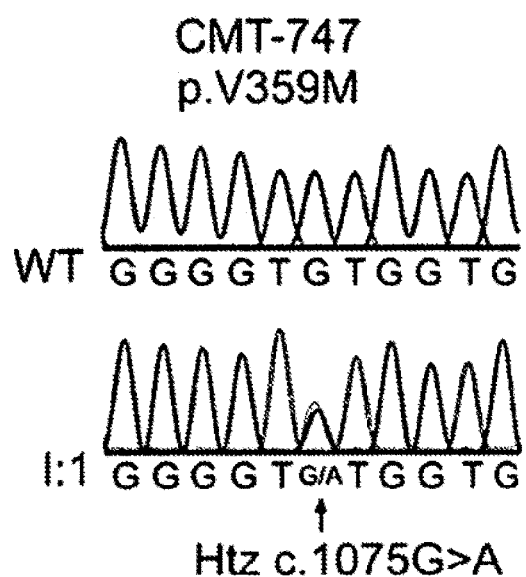
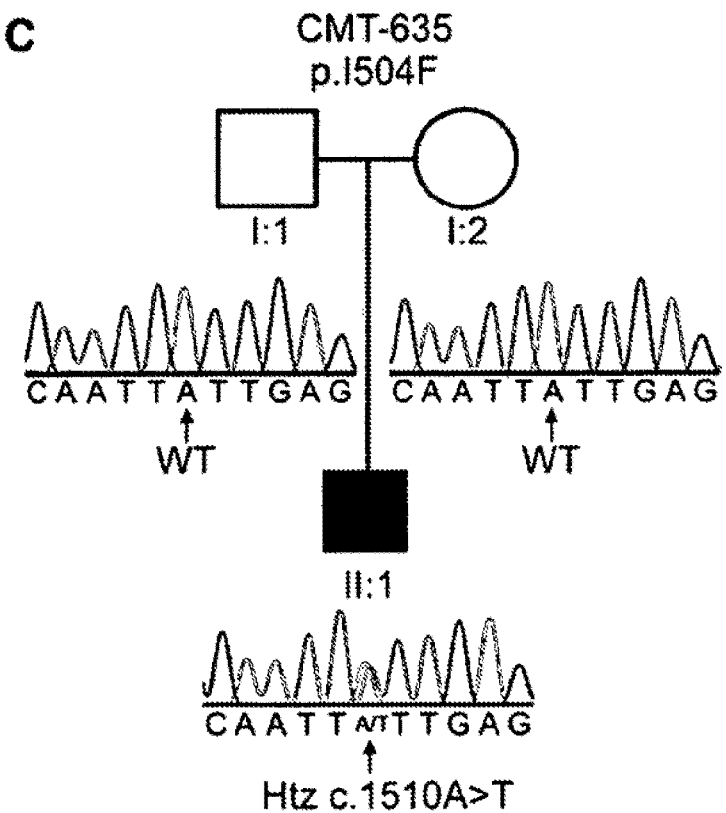

| | | |
|---|---|---|
| Homo sapiens | SIGALGPTGRGVVEYFGLDPEDVDVMMGTFTKSFGASGGYIGGKKELIDY | 397 |
| Bos Taurus | SIGALGPTGRGVVDYFGLDPEDVDIMMGTFTKSFGASGGYIGGKKALIDY | 397 |
| Rattusnorvegicus | SIGALGPSGRGVVDYFGLDPEDVDVMMGTFTKSFGASGGYIGGKKELIDY | 395 |
| Musmusculus | SIGALGPSGRGVVDYFGLDPEDVDVMMGTFTKSFGASGGYIGGKKELIDY | 395 |
| Daniorerio | SIGALGPGGRGVVEYFGLDPRDVDIMMGTFTKSFGAAGGYIGGRKDLIDY | 369 |
| D. melanogaster | SVGAMGSRGRGVTDYFNVDPKEVDILMGTFTKSFGSAGGYLAGSKKLIDF | 443 |
| S. cerevisiae | SIGAMGPTGRGVCEIFGVDPKDVDILMGTFTKSFGAAGGYIAADQWIIDR | 384 |
| S. paucimobilis | SMGFFGPNGRGVYEAQGLEG-QIDFVVGTFSKSVGTVGGFVVSNHPKFEA | 283 |
| | | |
| Homo sapiens | GFPATPIIESRARFCLSAAHTKEILDTALKEIDEVGDLLQLK-------Y | 539 |
| Bostaurus | GFPATPIIESRARFCLSAAHTRETLDTALKEIDEVGDLLHLK-------Y | 539 |
| Rattusnorvegicus | GFPATPIIESRARFCLSAAHTKEILDTALKEIDEVGDLLQLK-------Y | 537 |
| Musmusculus | GFPATPIIESRARFCLSAAHTKEILDTALKEIDEVGDLLQLK-------Y | 537 |
| Daniorerio | GFPATPIIESRARFCISAAHSKEMLDRALDVISEVGDLLQLK-------Y | 511 |
| D. melanogaster | GFPATPIMEGRIRFCLSAAHTKEQLDFALEAIDEIADDLGLK-------Y | 585 |
| S. cerevisiae | AYPATPLIESRVRFCMSASLTKEDIDYLLRHVSEVGDKLNLKSNSGKSSY | 533 |
| S. paucimobilis | RPPATPAGTFLLRCSICAEHTPAQIQTVLGMFQAAGRAVGVIG------- | 420 |

B

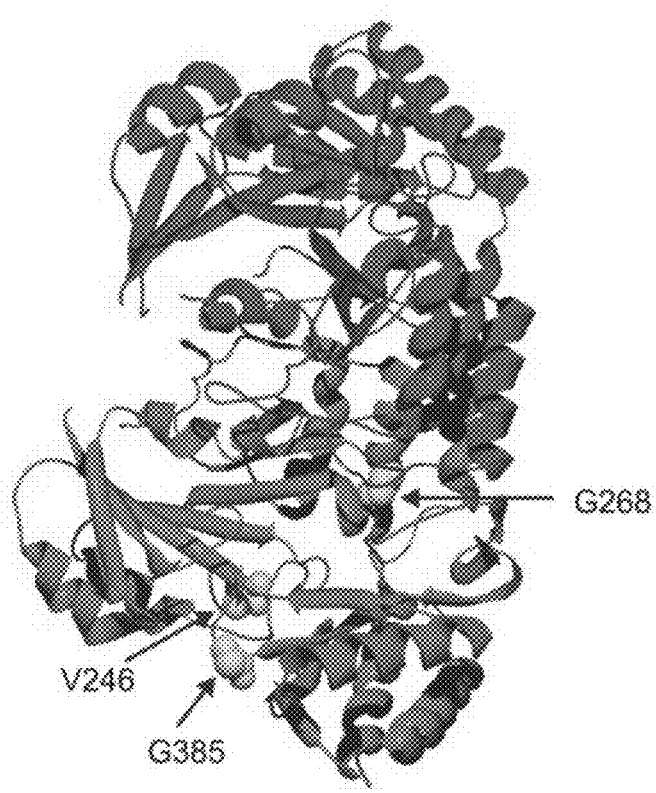

FIGURE 4
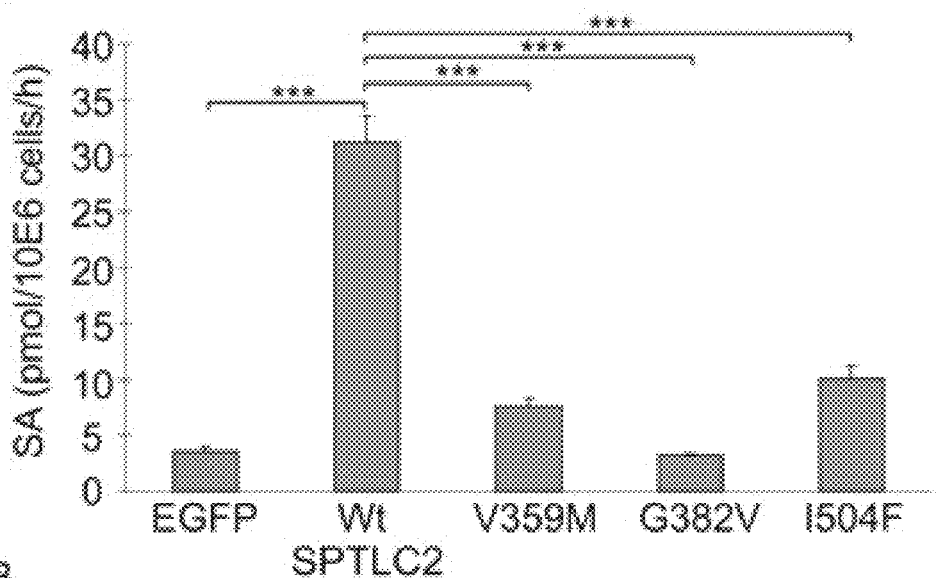
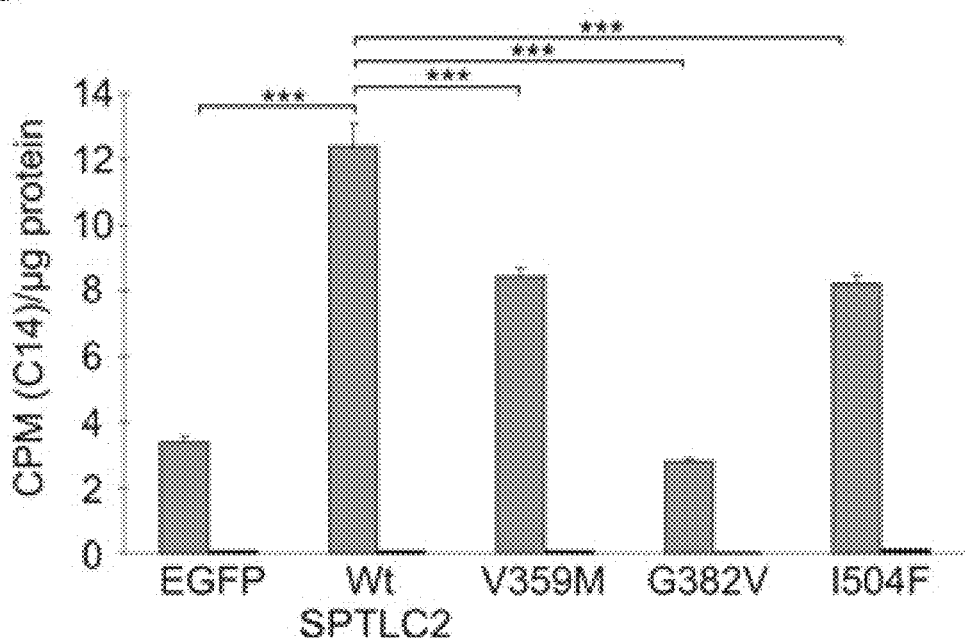

FIGURE 6
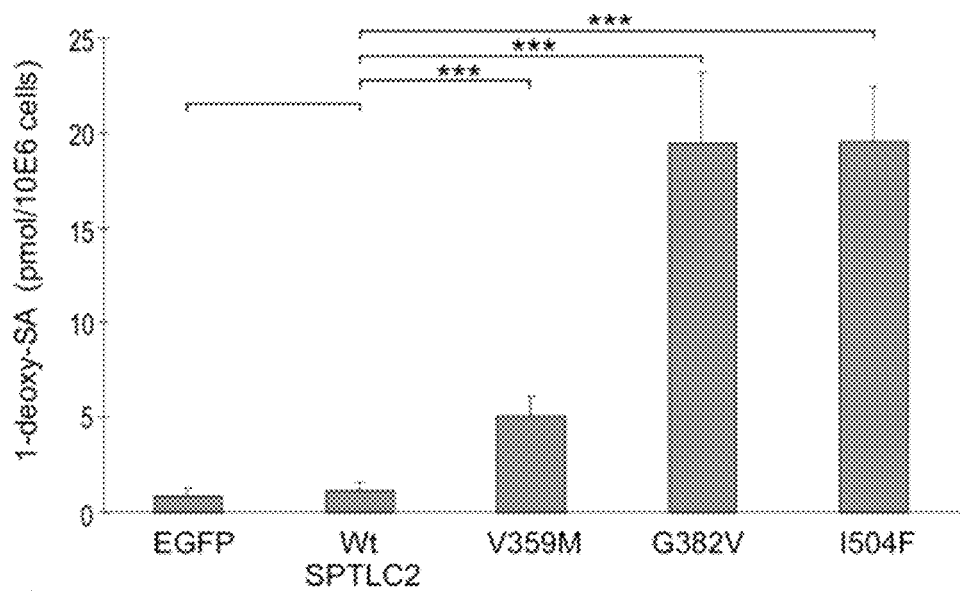
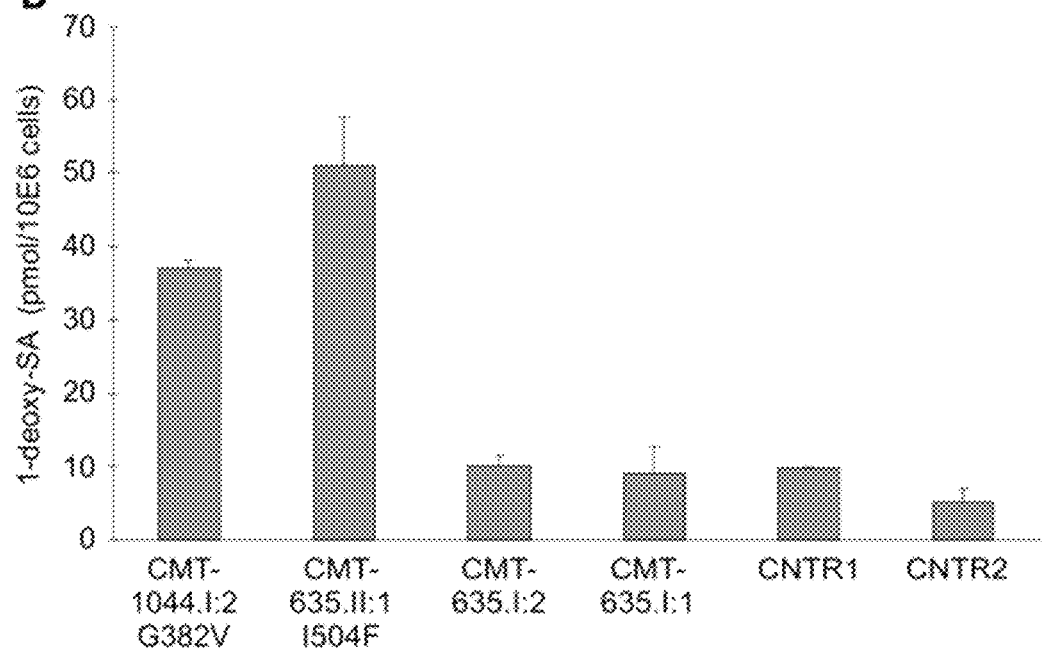

MUTATIONS IN SPTLC2 GENE ASSOCIATED WITH SENSORY NEUROPATHY

CROSS-REFERENCE TO RELATED APPLICATION

This application claims the benefit of U.S. Provisional Patent Application Ser. No. 61/403,619, filed Sep. 17, 2010, the disclosure of which is hereby incorporated herein in its entirety by this reference.

The patent or application file contains at least one drawing executed in color. Copies of this patent or patent application publication with color drawing(s) will be provided by the Office upon request and payment of the necessary fee.

TECHNICAL FIELD

The present invention relates to a method and kit for identifying a subject at risk of, or having, a sensory neuropathy related disease. In particular, the present invention is based on the determination of mutations in the SPTLC2 gene causing said sensory neuropathies.

BACKGROUND OF THE INVENTION

Hereditary sensory neuropathies (HSNs) form part of the inherited peripheral neuropathies which are generally subdivided into three categories, reflecting the selective or predominant involvement of the motor or sensory peripheral nervous system. The most common variants are the hereditary motor and sensory neuropathies (HMSNs), also called Charcot-Marie-Tooth syndrome, in which both the motor and sensory nerves are affected (Dyck et al. 1993). When only the peripheral motor nervous system is affected, the neuropathy is classified as distal hereditary motor neuropathy (Harding 1993). In contrast, sensory dysfunction prevails in the HSNs. As the autonomic nervous system is involved to a varying degree in HSNs they are often referred to as hereditary sensory and autonomic neuropathies (HSANs) (Dyck 1993).

The HSNs/HSANs are a clinically and genetically heterogeneous group of disorders. Patients usually exhibit prominent distal sensory loss with manifest insensitivity to pain in some. The prominent distal sensory loss frequently leads to chronic ulcerations in feet and hands, sometimes resulting in severe complications such as extensive soft tissue infections, osteomyelitis necessitating amputations of toes and fingers or, in rare instances, even of more proximal parts of the extremities (Dyck 1993). Autonomic dysfunction, such as anhidrosis, fever, blood pressure fluctuations and gastro-intestinal disturbances are present in some patients. Electrophysiologically, axonal nerve damage of sensory neurons is often found, but additional demyelination may also be present (Auer-Grumbach et al. 2003).

HSAN can be transmitted as an autosomal dominant (AD) or autosomal recessive (AR) trait. Isolated patients have also been described (Dyck 1993; Auer-Grumbach 2004). The AD types of HSAN usually present in the second or third decade of life with marked sensory involvement and minimal autonomic and variable motor involvement, while AR HSAN present either as congenital syndromes with striking sensory and autonomic abnormalities or as almost pure autonomic disorders (Verpoorten et al. 2006a).

A classification of the hereditary sensory neuropathies into types HSAN I-V (Dyck, 1993) was made based on age at onset, inheritance pattern and additional features. Molecular genetic research has shown that at least seven genes are associated with the different types of HSNs/HSANs (located on the worldwide web at www.molgen.ua.ac.be/CMTMutations/). Two genes have been associated with AD HSAN: missense mutations in serine palmitoyltransferase (SPT) long chain subunit 1 (SPTLC1) are found in families and individuals with HSAN type I, an adult-onset sensory neuropathy (Bejaoui et al. 2001; Dawkins et al. 2001). Mutations in the small GPTase late endosomal protein RAB7, cause CMT2B (Verhoeven et al. 2003; Meggouh et al. 2006). Mutations in the WNK1/HSN2 gene (protein kinase with-no-lysine(K)-1/hereditary sensory neuropathy type 2) and FAM134B cause AR HSAN type II, an early-onset ulcero-mutilating sensory neuropathy (Lafreniere et al. 2004; Kurth et al. 2009). HSAN type III, also known as Familial Dysautonomia or Riley-Day syndrome, presents with typical prominent autonomic manifestations early in life and is caused by mutations in the inhibitor of kappa-light polypeptide gene enhancer in B cells, kinase complex associated protein (IKBKAP) (Slaugenhaupt et al. 2001). Mutations in neurotrophic tyrosine kinase, receptor type 1 (NTRK1) are reported in families with congenital insensitivity to pain, anhidrosis and mental retardation (CIPA or HSAN type IV) (Indo et al. 1996). HSAN type V, a phenotype closely related to CIPA but with normal mental development and less pronounced anhidrosis, can be caused by mutations in nerve growth factor beta (NGFB) (Einarsdottir et al. 2004) but also by NTRK1-mutations (Houlden et al. 2001; Einarsdottir et al. 2004). Apart from these six HSAN subtypes other forms with distinct additional features exist, e.g., HSAN with gastroesophageal reflux and cough (Kok et al. 2003) and HSAN with spastic paraplegia (Bouhouche et al. 2006b). Recently, the gene for this last form has been identified as cytosolic chaperonin-containing t-complex peptide-1 (CCT5) (Bouhouche et al. 2006a).

The identification of causative genes for the HSAN forms in recent years has provided preliminary insights in the pathogenesis of these rare neuropathies although the fundamental underlying pathomechanisms still remain to be unveiled (Verhoeven et al. 2006). Additional descriptions of HSAN families and patients with known or novel genetic defects are needed to further refine the existing classification and to get a better insight into the molecular basis of these disorders.

SUMMARY OF THE INVENTION

The present invention has identified for the first time a clear link between nucleic acid variations in the SPTLC2 gene and sensory neuropathies. Accordingly, said new genetic markers provide a reliable diagnosis of or prediction of the risk to develop a sensory neuropathy related disease or disorder. Identification of such a genetic variation may not only provide insight as to why the response to treatment varies amongst individuals, but also may potentially decrease morbidity and mortality through improved risk assessment and the administration of personalized medicine.

Accordingly, the present invention provides a method and kit for identifying a subject at risk of, or having, a sensory neuropathy disease, comprising detecting the presence or absence of at least one nucleic acid variant in the SPTLC2 gene, whereby the presence of at least one nucleic acid variant identifies whether a subject is at risk of or has a sensory neuropathy disease. Specific regions of interest in the SPTLC2 gene are the coding region of the SPTLC2 gene. The sensory neuropathy disease preferably is a hereditary sensory and autonomic neuropathy disease selected from the group consisting of HSAN type 1, HSAN type 2, HSAN type 3, HSAN type 4 and HSAN type 5.

The methods and kits of the present invention can be carried out in combination with other methods for identifying a subject at risk of, or having, a sensory neuropathy disease. In a preferred embodiment the methods and kits are carried out in combination with a method for the detection of the presence or absence of a nucleic acid variant, or other markers, in any other gene.

Any detection method for the diagnosis and/or prognosis of a sensory neuropathy related disease or disorder forms part of the present invention. Preferred methods and means for the detection of the presence or absence of the nucleic acid variants of the present invention are hybridization, sequencing, PCR, primer extension, MLPA, OLA, restriction site analysis or high-resolution melting analysis for mutation scanning, or a combination thereof.

A further embodiment of the present invention relates to a method for selecting an appropriate treatment or therapeutic agent for a subject at risk of, or having, a sensory neuropathy disease, comprising determining the status of the sensory neuropathy disease by the methods of the present invention and selecting an appropriate treatment or therapeutic agent.

DESCRIPTION OF THE DRAWINGS

FIG. 3. Conservation of mutations among species and structural view of the bacterial SPT enzyme (A) ClustalW multiple protein alignment of the SPTLC2 orthologues from human (*Homo sapiens*), mouse (*Mus musculus*), rat (*Rattus norvegicus*), taurus (*Bos Taurus*), zebrafish (*Danio rerio*), fly (*Drosophila melanogaster*), baker's yeast (*Saccharomyces cerevisiae*) and Gram-negative bacteria with SPT-activity (*Sphingomonas paucimobilis*). (B) SPT structure of the *Sphingomonas paucimobilis*SPT homodimer (PDB ID: 2JGT) with the dimeric subunits represented in red and blue. The highlighted amino acids (V246, G268 and G385) correspond to the amino acids (V359, G382 and I504) mutated in the HSAN-I patients (see alignment in panel A).

FIG. 4. In vitro SPT activity measurements of HSAN-I associated SPTLC2 mutants. (A) Fumonisin B1 block assay. SPT activity in HEK293 cells stably expressing wt or mutant SPTLC2 is analyzed by measuring SA accumulation after treatment with Fumonisin B 1. Stable expression of wt SPTLC2 generates an 8.5-fold increase in SPT activity (p=3.24E-5), while the G382V mutant does not increase the SPT activity (p=0.18). The V359M and I504F mutations increase the activity significantly (p=0.00063 and 0.00064, respectively) but not to the same extent as wt SPTLC2. EGFP transfected cells served as control. (B) Radioactive-based SPT activity assay. SPT activity of HEK293 cells stably expressing wt or mutant SPTLC2 was determined by measuring the incorporation of $^{14}C$-labeled L-serine in vitro. Stable expression of wt SPTLC2 results in a significant increase in SPT activity, whereas the expression of G382V fails to raise SPT activity above basal levels. Expression of the V359M or I504F mutant elevates SPT activity, but not as drastically as wt SPTLC2. The right bars represent SPT activity in the presence of the SPT inhibitor myriocin (negative control; see FIG. 1). CPM: Counts per minute. *** P-value<0.001; SA: sphinganine. Data is represented as a mean with error bars representing standard deviations. Error bars and standard deviation were calculated based on three independent experiments.

FIG. 6. SPTLC2 mutations affect the enzymatic affinity of SPT. (A) Levels of 1-deoxy-SA in HEK293 cells stably expressing wt or mutant SPTLC2 are measured after an acid and base hydrolysis assay of the extracted lipids. Expression of wt SPTLC2 does not change cellular 1-deoxy-SA levels (p=0.55), whereas all three HSAN-I associated mutants result in significantly elevated 1-deoxy-SA levels (p=0.0025 for V359M; 0.00093 for G382V; 0.00048 for I504F). (B) 1-deoxy-SA levels in HSAN-I patient lymphoblastoid cell lines. The two HSAN-I patients CMT-1044.I:2 (G382V mutation) and CMT-635.II:1 (I504F mutation) show higher levels of 1-deoxy-SA compared to the unaffected parents of CMT-635.II:1 and to two unrelated control individuals. Unfortunately, no lymphoblast cells were available of patient CMT-747.I:1 carrying the V359M mutation. *** P-value<0.001; SA: sphinganine. Data is represented as a mean with error bars representing standard deviations. Error bars and standard deviation was calculated based on three independent experiments.

DETAILED DESCRIPTION OF THE INVENTION

Definitions

Figure 1:
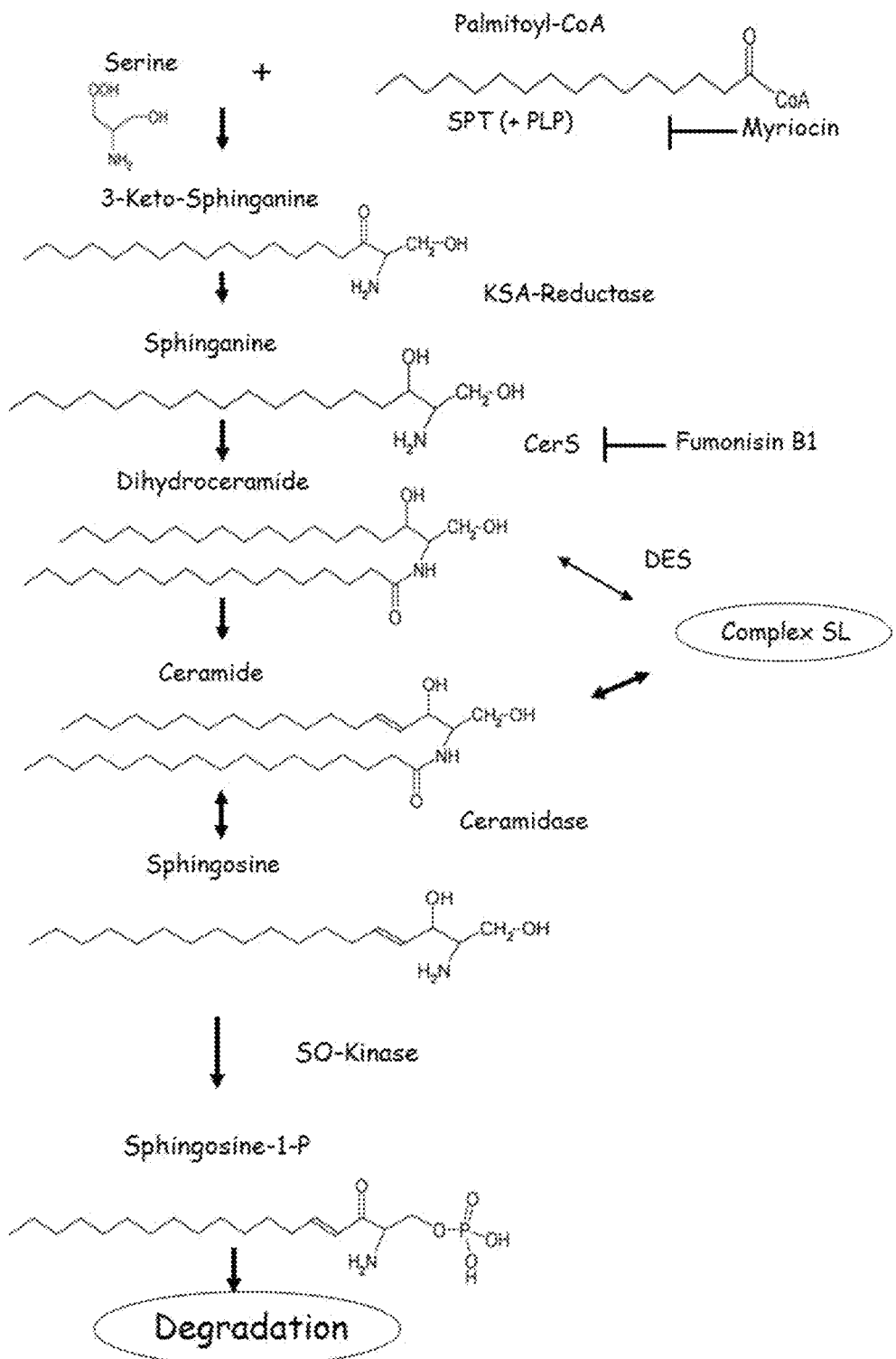
FIG. 1. De novo sphingolipid biosynthesis pathway. Left: the canonical pathway with L-serine; right the alternative, disease-related pathway with L-alanine. Condensation with L-alanine instead of L-serine gives rise to a metabolite lacking the $C_1$ hydroxyl group, obstructing conversion to complex SLs and degradation. The enzymes of the pathway are denoted in green. Myriocin and Fumonisin B1 are mycotoxins inhibiting the enzymes SPT and CerS respectively. SPT: serine palmitoyltransferase; PLP: pyridoxal-5'-phosphate; KSA: 3-keto-sphinganine; CerS: Ceramide synthase; DES: dihydroceramidedesaturase; SO: sphingosine; SL: sphingholipids.
Figure 1:
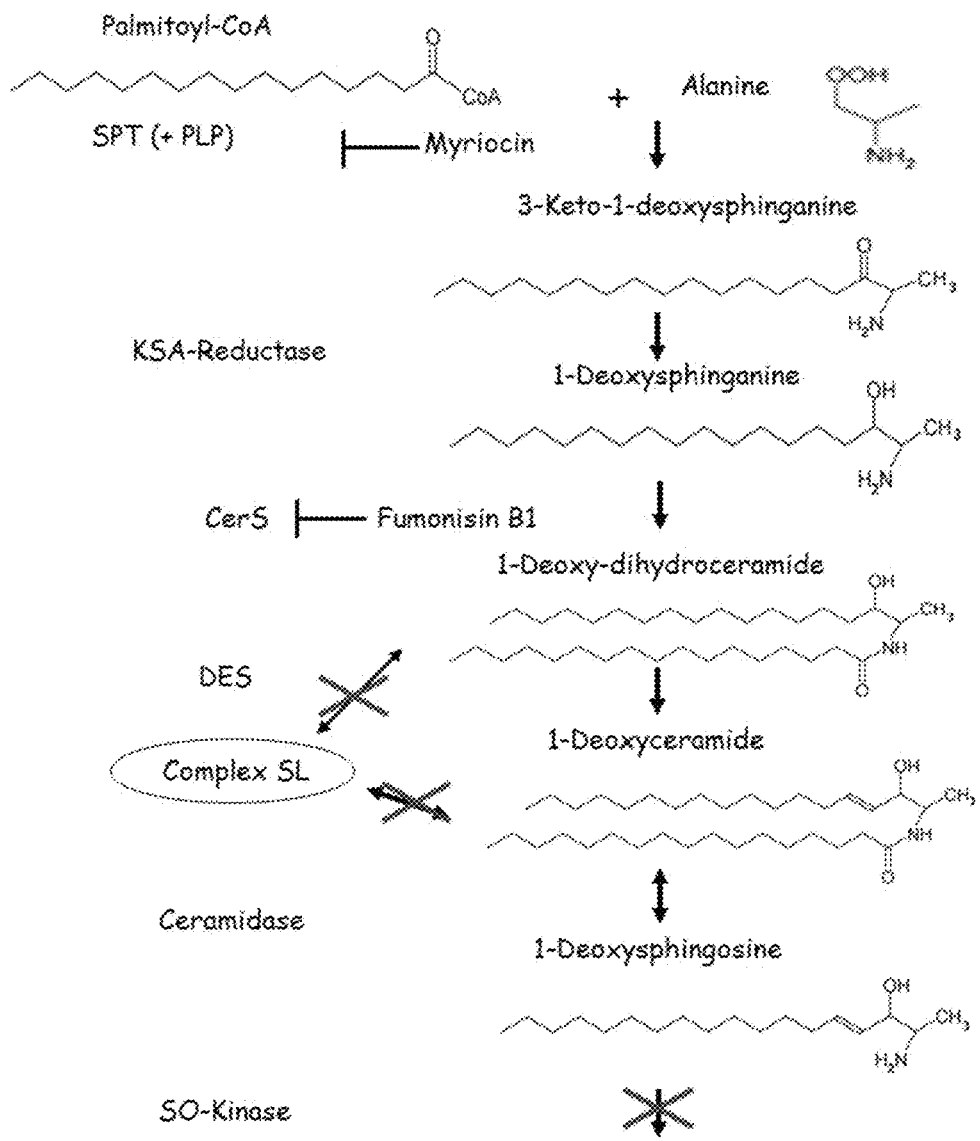

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g., "a" or "an," "the," this includes a plural of that noun unless something else is specifically stated.

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, for example, Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol L CRC Press (1976); Handbook of Biochemistry: Section A Proteins, Vol π, CRC Press (1976).

As used herein, the terms "polypeptide," "protein," "peptide" are used interchangeably and refer to a polymeric form of amino acids of any length, which can include coded and non-coded amino acids, chemically or biochemically modified or derivatized amino acids, and polypeptides having modified peptide backbones.

As used herein, the terms "nucleic acid," "polynucleotide," "polynucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular. A nucleic acid that is up to about 100 nucleotides in length, is often also referred to as an oligonucleotide.

As used herein, the term "allele" is one of several alternative forms of a gene or DNA sequence at a specific chromosomal location (locus). At each autosomal locus an individual possesses two alleles, one inherited from the father and one from the mother. The term "genotype" means the genetic constitution of an individual, either overall or at a specific locus.

As used herein, the term "homozygous" refers to having two of the same alleles at a locus. The term "heterozygous" refers to having different alleles at a locus.

As used herein, the terms "disorder" and "disease" are used interchangeably.

DETAILED DESCRIPTION

Systematic screening of the known HSAN genes in a large series of patients yielded pathogenic mutations in only 19% of probands (Rotthier et al. 2009), suggesting the involvement of other disease associated genes. By screening a set of functional candidate genes in a large HSAN cohort, the present inventors identified three heterozygous missense mutations in the SPTLC2 subunit of serine palmitoyltransferase (SPT), the first and rate-limiting enzyme in the de novo sphingolipid biosynthesis pathway, in four index patients presenting with a typical HSAN type I phenotype. This is particularly surprising since SPTLC2 was previously excluded as a cause for HSAN type I (Dawkins et al. 2002). Moreover, these mutations result in a partial to complete loss of SPT-activity and cause the formation of 1-deoxysphinganine, a neurotoxic metabolite. So, the present findings extend the genetic heterogeneity in HSAN related diseases and enlarge the group of HSAN neuropathies associated with SPT defects.

Thus, according to a first aspect, the invention relates to a method of identifying a subject at risk of, or having, a sensory neuropathy disease, comprising detecting the presence or absence of at least one nucleic acid variant in the SPTLC2 gene or a part thereof, whereby the presence of at least one nucleic acid variant identifies whether a subject is at risk of or has a sensory neuropathy disease.

As used herein, the term "SPTLC2 gene" refers to the gene encoding the second subunit of the serine palmitoyltransferase (SPT). The SPT enzyme is a multisubunit structure, consisting of dimeric subunits of SPTLC1 with either SPTLC2 or SPTLC3 (Hornemann et al. 2007). It is associated with the endoplasmic reticulum (ER) where it catalyzes the pyridixal-5'phosphate (PLP) dependent condensation of L-serine with palmitoyl-CoA. This is the first and rate-limiting step in the de novo biosynthesis of sphingolipids (see also FIG. 1). Sphingolipids are essential components of all eukaryotic cells where they play important roles in membrane structure and in intracellular signaling.

The reference nucleic acid and protein sequences indicated in the current invention are derived from GeneBank (NCBI) and indicated by their respective accession number, as is well known to the person skilled in the art. Frequent updates of the nomenclature for the description of sequence variations are provided on the website of the Human Genome Variation Society. Accordingly, the nucleotide numbering of the coding DNA and RNA reference sequence is as follows: nucleotide +1 is the A of the ATG-translation initiation codon, there is no nucleotide 0, the nucleotide 5' of the ATG-translation initiation codon is −1. The nucleotide number is preceded by "g." when a genomic or by "c." when a cDNA reference sequence is used. Substitutions are designated by ">". Similarly, the amino acid number is preceded by "p" when a protein reference sequence is used.

The human SPTLC2 gene (serine palmitoyltransferase long chain subunit 2) is located at chromosome 14 at location 14q24.3 and comprises 12 exons. The reference nucleic acid sequence for the human SPTLC2 is NC_000014.8 (gDNA; Version: NC_000014.8 GI:224589805; Region: complement(77973269.78083109); SEQ ID NO:1) or NM_004863 (cDNA; Version: NM_004863.2 GI:31881646; SEQ ID NO:2). The reference protein sequence encoded by the human SPTLC2 gene is NP_004854 (Version: NP_004854.1 GI:4758668; SEQ ID NO:3).

The term "nucleic acid variant" or "polymorphism" or "variant" as used in the present invention, means that the nucleic acid sequence at a certain position in the SPTLC2 gene differs relative to one or more reference nucleic acid sequences. The most simple nucleic acid polymorphism is a polymorphism affecting a single nucleotide, i.e., a single nucleotide polymorphism or SNP. Nucleic acid polymorphisms further include any number of contiguous and/or non-contiguous differences in the primary nucleotide sequence of the nucleic acid under investigation relative to the primary nucleotide sequence of one or more reference nucleic acids. The term "polymorphic position" or "position" refers to the nucleic acid position at which a nucleic acid polymorphism arises. Nucleic acid sequences comprising at least one such polymorphism are referred to as "polymorphic nucleic acid sequences," "polymorphic polynucleotides," "polymorphic sequences" or the like. The polymorphism or nucleic acid variant can be an insertion, deletion, substitution, tandem repeat or similar.

The phrase "detecting the presence or absence," e.g., of a genetic marker as used herein, refers to determining whether or not the relevant genetic event, linked with the occurrence of a disease, is present. In practice, both the absence and the presence of a certain event can function as markers. Accordingly, reference to detecting the presence of a nucleic acid variant generally encompasses determining whether the marker is present, either based on the absence or the presence of the variant in a sample. Moreover, this also includes the possible finding that the marker is not present in the sample, i.e., determining the absence (or presence) of a nucleic acid variant. In both cases determining the presence of the marker can also be done indirectly, e.g., where the presence of a nucleic acid variant is linked to disease, the occurrence of this marker can also be done by determining the homozygous presence of the corresponding allele not comprising the nucleic acid variant. Similarly, allele specific oligonucleotide primers and probes for detecting the presence of a SNP can be specific for the allele where the SNP is not present.

In a specific embodiment, the present invention relates to a method according to the present invention, wherein the SPTLC2 genotype has at least one variant allele of the SPTLC2 gene (heterozygous). In a further embodiment, the method of the invention relates to a method according to the present invention, wherein the SPTLC2 genotype has two variant or wild-type alleles of the SPTLC2 gene (homozygous).

The method of the present invention is particularly suited for the diagnosis and/or prognosis of a sensory neuropathy related disease or disorder in a subject, preferably a human. A sensory neuropathy related disease includes, without limitation, a hereditary sensory neuropathy (HSN), otherwise referred to as hereditary sensory and autonomic neuropathy (HSAN), which can be further classified into HSAN type 1, HSAN type 2, HSAN type 3, HSAN type 4 and HSAN type 5 (see Background section). With the methods of the present invention, the risk for developing a sensory neuropathy disorder can be determined. The "subject" on which the method of the present invention is carried out can be any subject for which the diagnosis/prognosis/risk of an sensory neuropathy needs to be determined. The subject may be a non-human subject such as (but not limited to) a cow, a pig, a sheep, a goat, a horse, a monkey, a rabbit, a dog, a cat, a mouse, a rat, a hamster, a zebrafish, a pufferfish (Fugu), a fly, a worm or *C. elegans*. More preferably, the subject is a primate. Even more preferably, the subject is a human.

In a further embodiment, the method of the invention comprises the step of determining whether one or more nucleic acid variants in the SPTLC2 gene are present in 0, 1 or 2 copies, more particularly whether a nucleic acid variant in the SPTLC2 gene is present in one or both alleles.

In another embodiment of the above method the presence or absence of the nucleic acid variant can be detected in the SPTLC2 gene or part thereof. Within the present context, "part thereof" refers to the region of interest, i.e., the region of the SPTLC2 gene comprising a nucleic acid variant. More particular, "a part thereof" refers to the 5'UTR, the promoter region, exon 1, intron 1, exon 2, intron 2, exon 3, intron 3, exon 4, intron 4, exon 5, intron 5, exon 6, intron 6, exon 7, intron 7, exon 8, intron 8, exon 9, intron 9, exon 10, intron 10, exon 11, intron 11, exon 12, and/or intron 12. Preferably, the polymorphism is located in the promoter region and/or in the coding region of the SPTLC2 gene, e.g., in at least one of the exons of the SPTLC2 gene. Typically, the nucleic acid variant is, without limitation, a substitution, deletion, insertion, duplication, translocation and/or inversion of at least one nucleotide.

The invention relates in particular to any polymorphism located within the coding region of the SPTLC2 gene as can be identified in the cDNA sequence (SEQ ID NO:2). More particularly, the nucleic acid variant is detected in at least one position of the coding region of the SPTLC2 gene including, without limitation, position 1145, 1075 or 1510 of the cDNA sequence (These positions are relative to the ATG start codon beginning at position 189 of SEQ ID NO: 2. The corresponding positions in SEQ ID NO: 2 are 1333, 1263, and 1698 respectively). More specific, the nucleic acid variant is c.1145G>T, resulting in the amino acid change G382V. Or, the nucleic acid variant is c.1075G>A, resulting in the amino acid change V359M. Or, the nucleic acid variant is c.1510A>T, resulting in the amino acid change I504F.

As used herein, the term "wild-type" sequence is analogous to the "reference" sequence, and both terms are used interchangeably herein. The reference sequence for e.g., the wild-type human SPTLC2 gene can be the genomic DNA sequence as identified by NC_000014 (gDNA; Version: NC_000014.8 GI:224589805; SEQ ID NO:1) or the cDNA sequence including the coding sequence as identified by NM_004863 (cDNA; Version: NM_004863.2 GI:31881646; SEQ ID NO:2). For example, the allele may be normal as in the reference sequence(s), or it may be a variant, such as a structural or a non-structural variant. The amino acid sequence of the wild-type human SPTLC2 protein is identified by SEQ ID NO:3.

It will be apparent to the person skilled in the art that there are a large number of analytical procedures which may be used to detect the presence or absence of the nucleic acid variants mentioned herein. Nucleic acid from any nucleated cell can be used as the starting point for such assay techniques and may be isolated according to standard nucleic acid preparation procedures well known to those of skill in the art. Many current methods for the detection of allelic variation are reviewed by Nollau et al. (1997), and in standard textbooks, for example, "Laboratory Protocols for Mutation Detection," Ed. by U. Landegren, Oxford University Press, 1996 and "PCR," $2^{nd}$ Edition" by Newton & Graham, BIOS Scientific Publishers Limited, 1997 (incorporated herein by reference).

The method of the present invention can be carried out in vivo or in vitro. Preferred, however, is in vitro detection of nucleic acid variants in the SPTLC2 gene in a biological sample obtained from the subject. The term "biological sample" means a tissue sample or a body fluid sample. A tissue sample includes, but is not limited to, buccal cells, a brain sample, a skin sample, organ sample, placental tissue or fetal cells. The term "body fluid" refers to all fluids that are present in the body including but not limited to blood, plasma, serum, lymph, synovial fluid, amniotic fluid, urine, saliva or cerebrospinal fluid. The biological sample may also be obtained by subjecting it to a pretreatment if necessary, for example, by homogenizing or extracting. Such a pretreatment may be selected appropriately by those skilled in the art depending on the biological sample to be subjected.

A nucleic acid comprising an intended sequence prepared from a biological sample may be prepared from DNA (e.g., gDNA or cDNA) or RNA (e.g., mRNA). Release, concentration and isolation of the nucleic acids from the sample can be done by any method known in the art. Currently, various commercial kits are available such as the QIAamp Blood Kit from Qiagen (Hilden, Germany) for the isolation of nucleic acids from blood samples, or the "High pure PCR Template Preparation Kit" (Roche Diagnostics, Basel, Switzerland) or the DNA purification kits (PureGene, Gentra, Minneapolis, US). Other, well-known procedures for the isolation of DNA or RNA from a biological sample are also available (Sambrook et al., 1989; Ausubel et al., 2003).

When the quantity of the nucleic acid is low or insufficient for the assessment, the nucleic acid may be amplified. Such amplification procedures can be accomplished by those methods known in the art, including, for example, the polymerase chain reaction (PCR), ligase chain reaction (LCR), nucleic acid sequence-based amplification (NASBA), strand displacement amplification, rolling circle amplification, T7- polymerase amplification, and reverse transcription polymerase reaction (RT-PCR).

After performing the extraction and/or amplification procedure, the presence or absence of certain nucleic acid variants in the target sequence can be detected. Numerous methods for detecting a single nucleotide anomaly in nucleic acid sequences are well-known in the art. The present invention is not limited by any particular method used to detect the target sequences disclosed herein. Examples of such methods are described by Gut (2001) and Syvanen (2001), and include, but are not limited to, hybridization methods such as reverse dot blot, Line Probe Assay (LiPA), geneChip™ microarrays, dynamic allel-specific hybridization (DASH), peptide nucleic acid (PNA) and locked nucleic acid (LNA) probes, TaqMan™ (5 'nuclease assay) and molecular beacons; allele-specific PCR methods such as intercalating dye, FRET primers and Alphascreen™; primer extension methods such as ARMS, kinetic PCR, SNPstream™, Genetic Bit Analysis™ (GBA), multiplex minisequencing, SNaPshot, pyrosequencing, MassExtend, MassArray, Goodassay, microarray miniseq, APEX (arrayed primer extension), sequence specific priming (SSP), microarray primer extension, Tag arrays, coded microspheres, template-directed incorporation (TDI), fluorescence polarization; oligonucleotide ligation methods such as colorimetric OLA, sequence-coded OLA, multiplex ligation-dependent probe amplification (MLPA), microarray ligation, ligase chain reaction, padlock probes and rolling circle amplification; endonuclease cleavage methods such as restriction site analysis (RFLP) and Invader™ assay; high-resolution melting (HRM) analysis for mutation scanning. In a preferred embodiment, the detection of the presence or absence of a nucleic acid variant is determined by DNA or RNA hybridization, sequencing, PCR, primer extension, MLPA, oligonucleotide ligation assay (OLA), restriction site analysis, or high-resolution melting (HRM) analysis for mutation scanning, or a combination thereof. Accordingly, the method of the present invention optionally comprises the steps of isolating nucleic acids from the sample and/or an amplification step.

The present invention also provides isolated oligonucleotides, i.e., primers and probes, in order to amplify and/or detect nucleic acid variants and/or the wild-type sequence of the SPTLC2 gene. The wild-type sequence of the SPTLC2 gene is identified by its genomic DNA sequence (SEQ ID NO:1) or cDNA sequence (SEQ ID NO:2). Such primers or probes, specifically hybridizing to the target nucleic acid, are of any convenient length such as to consist of at least 8, 9, 10, 11, 12, 13, 14 or 15 nucleotides and up to 40 nucleotides, up to 30 nucleotides or more conveniently up to 25 nucleotides in length, such as, for example, 8, 9, 10, 11, 12, 13, 14, 15, 16, 17, 18, 19, 20, 21, 22, 23, 24 or 25 nucleotides in length. In general, such primers or probes will comprise nucleotide sequences entirely complementary to the corresponding wild-type or variant locus in the SPTLC2 gene. However, if required one or more nucleotides may be added or one or more mismatches may be introduced, provided that the discriminatory power of the oligonucleotide primer or probe is not unduly affected.

An oligonucleotide primer (or primer pair) designed to specifically recognize and amplify either a wild-type or variant allele at a locus is referred to as an allele specific primer (or primer pair). The same applies for an allele specific probe, i.e., an oligonucleotide probe that specifically hybridizes to either a wild-type or variant allele.

Specific length and sequence of the probes and primers will depend on the complexity of the required nucleic acid target, as well as on the reaction conditions such as temperature and ionic strength. In general, the hybridization conditions are to be stringent as known in the art. "Stringent" refers to the condition under which a nucleotide sequence can bind to related or non-specific sequences. For example, high temperature and lower salt increases stringency such that non-specific binding or binding with low melting temperature will dissolve.

The primers or probes of the invention may carry one or more labels to facilitate detection. The nature of the label is not critical to the invention and may be fluorescent, chemiluminescent, enzymatic, radioactive, chemical or other, provided it doesn't interfere with correct hybridizing of the oligonucleotide.

In a preferred embodiment, the primer or probe consists of 10 to 30 nucleotides, preferably 15 to 30 or 15 to 25 nucleotides, and is capable of specifically forming a hybrid with a part of the SPTLC2 gene and is at least one or more selected from the group consisting of: 1) an oligonucleotide capable of hybridizing under a stringent condition with the sequence as represented by SEQ ID NO:1 or 2, or the complementary thereof; 2) an oligonucleotide of which the sequence is for 80, 85 or 90% identical to the sequence as represented by SEQ ID NO:1 or 2, or the complementary thereof; and 3) an oligonucleotide capable of hybridizing under a stringent condition with the sequence as represented by SEQ ID NO:1 or 2, wherein one or more nucleotides was subjected to a variation such as a substitution, deletion, insertion or addition, or the complementary thereof.

More particular, the present invention relates to an isolated oligonucleotide consisting of 10 to 30 nucleotides, preferably 15 to 30 or 15 to 25 nucleotides, for detecting the presence of one or more nucleic acid variants in SEQ ID NO:1 or 2, or the complementary strand. More specific, the nucleic acid variants are located at position 1145, 1075 or 1510 relative to the ATG start codon beginning at position 189 of SEQ ID NO:2 (The corresponding numbering in SEQ ID NO: 2 is 1333, 1263, and 1698 respectively).

The polymorphism located in the SPTLC2 gene may also be detected in vitro by determining in the isolated SPTLC2 protein the presence or absence of an amino acid change by sequencing said protein. The amino acid change may also be detected by any conventional method known in the art, for example, by mass-spectroscopy, gel electrophoresis, MALDI-TOF mass spectroscopy, ELISA, protein arrays, determination of the molecular weight, or by isoelectrofocusing.

Any human gene can be studied together with the method of the present invention. Of the different genetic markers identified, further important risk factors are polymorphisms or nucleic acid variations in one or more of the following genes (Rotthier et al. 2009): SPTLC1 (e.g., Bejaoui et al. 2001; Dawkins et al. 2001), RAB7A (e.g., Verhoeven et al. 2003; Meggouh et al. 2006), WNK1/HSN2 (e.g., Lafreniere et al. 2004), IKBKAP (e.g., Slaugenhaupt et al. 2001), FAM134B (e.g., Kurth et al. 2009), NTRK1 (e.g., Indo et al. 1996), NGFβ (e.g., Einarsdottir et al. 2004; Houlden et al. 2001), CCT5 (e.g., Bouhouche et al. 2006a), or SCN9A (e.g., Cox et al. 2006).

In a further embodiment, the method of the present invention may also be used in determining whether and which therapeutic agent might be suitable for a patient being at risk of, or having a sensory neuropathy disease. The therapeutic agent may be used to prevent or treat the disease. As used herein, the term "preventing a disease" means inhibiting or reversing the onset of the disease, inhibiting or reversing the initial signs of the disease, inhibiting the appearance of clinical symptoms of the disease. As used herein, the term "treating a disease" includes substantially inhibiting the disease, substantially slowing or reversing the progression of the disease, substantially ameliorating clinical symptoms of the disease or substantially preventing the appearance of clinical symptoms of the disease.

Another aspect of the invention relates to a diagnostic kit for use in the method as described herein. More specific, the invention encompasses a kit for identifying a subject at risk of, at risk of having, or having, a sensory neuropathy disease. This kit can be based on the detection of nucleic acid variants in the SPTLC2 gene of said subject. Accordingly, the kit of the present invention comprises reagents that selectively detect a nucleic acid variant in the SPTLC2 gene.

A kit based on the detection of nucleic acid variants in the SPTLC2 gene may comprise:
(a) a means or reagent for detecting the presence or absence of one or more nucleic acid variants in the SPTLC2 gene of said subject; and
(b) optionally, a means for determining, from the nucleic acid variants detected with the means of step (a), whether the subject is at risk of, or has, a sensory neuropathy disease.

More preferred, the kit comprises a means for detecting the presence or absence of one or more nucleic acid variants in the coding region of the SPTLC2 gene. In a preferred embodiment of the present invention, the kit comprises:
(a) a means or reagent for detecting the presence or absence of a nucleic acid variant at one or more of the following positions 1145, 1075 or 1510 of the coding region of the SPTLC2 gene, as can be identified by the cDNA sequence (SEQ ID NO: 2); and
(b) optionally, a means for determining, from the nucleic acid variants detected with the means of step (a), whether the subject is at risk of, or has, an sensory neuropathy disease.

In a specific embodiment the means or reagents in step (a) of said kit may comprise, without limitation:

(i) when appropriate, a means for obtaining a target SPTLC2 polynucleic acid present in a biological sample and/or obtaining the nucleotide sequence thereof;
(ii) at least one oligonucleotide suitable for detection of a target SPTLC2 nucleic acid and/or at least one oligonucleotide pair suitable for amplification of a target SPTLC2 polynucleic acid;
(iii) when appropriate, an agent for denaturing nucleic acids;
(iv) when appropriate, an enzyme capable of modifying a double stranded or single stranded nucleic acid molecule;
(v) when appropriate, a hybridization buffer, or components necessary for producing said buffer;
(vi) when appropriate, a wash solution, or components necessary for producing said solution;
(vii) when appropriate, a means for detecting partially or completely denatured polynucleic acids and/or a means for detecting hybrids formed in the preceding hybridization and/or a means for detecting enzymatic modifications of nucleic acids;
(viii) when appropriate, a means for attaching an oligonucleotide to a known location on a solid support.

In a preferred embodiment the means or reagent in step (a) of said kit comprises at least one oligonucleotide probe suitable for detection of a target SPTLC2 nucleic acid. In a specific embodiment, the target SPTLC2 nucleic acid is located in the coding region, or part thereof. Even more specific, the target SPTLC2 nucleic acid is located at cDNA position 1145, 1075 and/or 1510 of the SPTLC2 gene. The designated positions either have the wild-type nucleotides or nucleic acid variants thereof. Optionally, the means or reagent in step (a) also includes at least one pair of primers suitable for amplification of a target SPTLC2 polynucleic acid. More particular, the target polynucleic acid is the coding region of the SPTLC2 gene, or part thereof. Even more specific, the target SPTLC2 polynucleic acid comprises cDNA position 1145, 1075 and/or 1510 of the SPTLC2 gene. The designated positions either have the wild-type nucleotides or nucleic acid variants thereof.

The term "hybridization buffer" means a buffer allowing a hybridization reaction between the oligonucleotides and the polynucleic acids present in the sample, or the amplified products, under the appropriate stringency conditions. The term "wash solution" means a solution enabling washing of the hybrids formed under the appropriate stringency conditions.

In a specific embodiment of the kit, the means for detecting the presence or absence of nucleic acid variants in the SPTLC2 gene comprises a multiplex assay.

The means in step (b) of said kit, for determining, from the nucleic acid variants in the SPTLC2 gene detected with the means of step (a), whether the subject is at risk of, or has, a sensory neuropathy disease include a table, a chart, or similar, generally referred to as "a predisposition risk algorithm," indicating the SPTLC2 nucleic acid variants or haplotypes that confer a risk for or the existence of a sensory neuropathy disease. As used herein, the term "chart" refers to graphical presentation, visual aid, diagram, plan, graph, sheet, map or the like including the relevant information. The determination of the risk can be performed manually or with the use of a computer.

The kit of the present invention may include, in addition to the means or reagent for detecting the presence or absence of a nucleic acid variant, a means for detection other risk factors, e.g., nucleic acid variants in a gene, for a sensory neuropathy disease. In a preferred embodiment, the kit additionally includes a means, preferably probes, for detecting the genotype of or a nucleic acid variant in at least one of the genes selected from the group consisting of:SPTLC1, RAB7A, WNK1/HSN2, IKBKAP, FAM134B, NTRK1, NGFβ, CCT5 or SCN9A.

The following examples are intended to promote a further understanding of the present invention. While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

EXAMPLES

Example 1

Mutations in SPTLC2 are Associated with HSAN-I

The coding sequence and intron-exon boundaries of SPTLC2 (chromosome location 14q24.3) were analyzed in 78 patients with HSAN, previously screened and found negative for mutations in the other known HSAN genes (SPTLC1,RAB7A, the complete coding region of WNK1/HSN2, FAM134B, NTRK1, NGFB and CCT5) (Rotthier et al. 2009; Kurth et al. 2009). We identified three heterozygous missense mutations in four index patients, for whom clinical and electrophysiological information is summarized in Table 1 and Table 2. The mutations were absent in 300 European control individuals.

Figure 2:
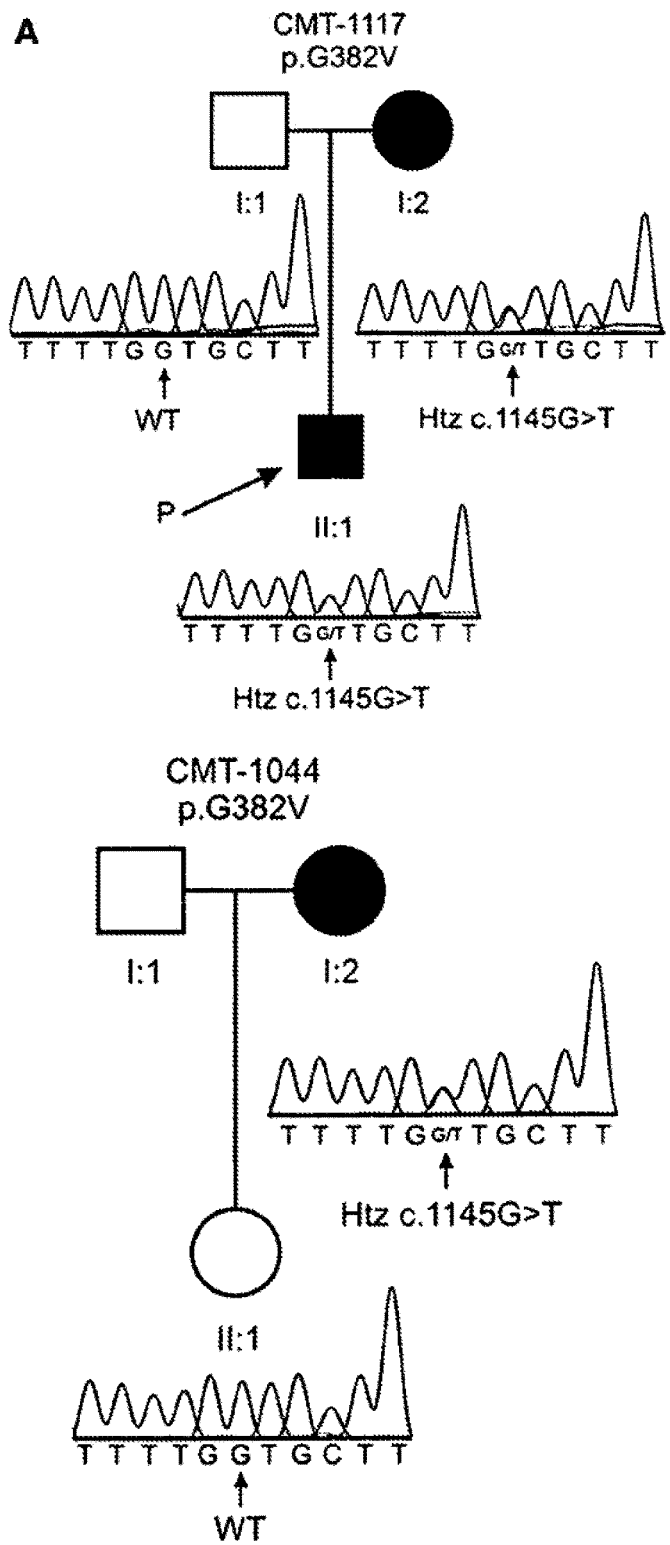
FIG. 2. Missense mutations in SPTLC2 are associated with HSAN-I. (A) Sequence trace files of the G382V mutation in families CMT-1117 (proband indicated by arrow) and CMT-1044. (B) Isolated patient CMT-747.I:1 with the V359M mutation. (C) Patient CMT-635.II:1 carrying a de novo I504F mutation.

A c.1145G>T sequence variation (p.G382V) was found in two families (CMT-1044 and CMT-1117; FIG. 2a). The proband of family CMT-1117 presented with progressive distal sensory loss and distal muscle weakness in the lower limbs at the age of 38 years. The clinical presentation was similar in a member of family CMT-1044. In addition, this patient experienced dysesthesia in hands and feet and developed osteomyelitis of a thumb. Based on haplotype analysis, these families were found to be unrelated (data not shown).

A second heterozygous mutation (c.1075G>A; p.V359M) was discovered in an isolated patient (CMT-747.I:1; FIG. 2b). This patient was diagnosed with HSAN after developing distal sensory dysfunction with a foot ulceration necessitating amputation of a toe. No signs of motor or autonomic involvement were noted.

The third mutation (c.1510A>T; p.I504F) is a heterozygous de novo mutation found inpatient CMT-635.II:1 who presented with an atypical early onset sensorimotor neuropathy, complicated with ulcerations, osteomyelitis and anhidrosis (FIG. 2c). Paternity testing was done to confirm parenthood.

Nerve conduction studies were performed in all patients revealing predominantly axonal sensori-motor neuropathy; this diagnosis was confirmed by a sural nerve biopsy inpatient CMT-747.I:1 (Table 1 and Table 2).

No disease associated sequence variants were identified in the coding region or the intron-exon boundaries of SPTLC3 (chromosome location 20p12.1; GenBank accession number NM_018327).

Example 2

SPTLC2 Mutations are Associated with a Reduction in SPT Activity

All three mutations in SPTLC2 target highly conserved amino acids (FIG. 3a) rendering it likely that they are functionally important. We set out to investigate the effect of these mutations on SPT activity in stably transfected Flp-in HEK293 cells. The Flp-in system ensures the stable insertion of a single copy of the transgene at a specific genomic location. In this way, moderate and equal expression of the different transgenes is obtained. The cells were treated for 24 h with Fumonisin B1,a mycotoxin that blocks the de novo sphingolipid biosynthesis pathway downstream of SPT (Wang et al. 1991) (FIG. 1). Since condensation of palmitoyl-CoA and serine by SPT is the rate-limiting step in the biosynthesis pathway, the resulting accumulation of sphinganine (SA) reflects the canonical SPT activity (incorporation of L-serine). Stable expression of wild-type (wt) SPTLC2 resulted in an 8-fold increase in SA accumulation compared to control cells stably expressing GFP. This is in agreement with earlier reports, in which overexpression of wt SPTLC2 indeed leads to higher SPT activity (Hornemann et al. 2006). Stable expression of the G382V mutant on the other hand did not increase SA accumulation above basal levels. The V359M and I504F expressing cells showed an increase in SA accumulation but far less pronounced than wt SPTLC2 expressing cells (FIG. 4a). Thus, the three mutations result in a partial to complete loss of SPT activity.

The effect on canonical SPT activity was confirmed in an alternative radioactive-based in vitro assay. Total lipids were extracted from HEK293 cells stably expressing wt or mutant SPTLC2 and incubated with $^{14}$C-labeled L-serine, PLP and palmitoyl-CoA after which the incorporation of the radioactively labeled serine was measured (FIG. 4b). The results resembled those of the previous assay. Stable expression of wt SPTLC2 caused a significant increase in SPT activity, whereas the expression of G382V failed to raise SPT activity above basal levels. Expression of the V359M or I504F mutant elevated SPT activity, but not to the same extent as wt SPTLC2. The relative increase in SPT activity in V359M and I504F expressing cells was more pronounced than in the Fumonisin B1 block assay (FIG. 4a). This difference could be explained by the higher serine concentration used in the latter in vitro assay compared to the serine concentrations present in the cell culture medium during the former assay.

Example 3

SPTLC2 Mutants Differentially Affect in vivo SPT Activity in *S. cerevisiae*

Figure 5:
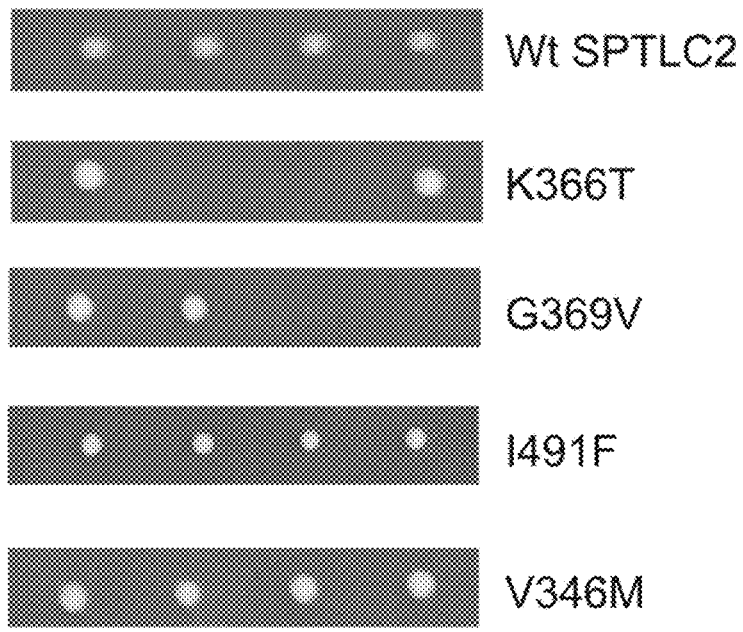
FIG. 5. Genetic complementation test in *S. cerevisiae* by tetrad dissection of a heterozygous LCB2/lcb2:: KanMX strain complemented with different YCplac111_LCB2 constructs. Wild-type LCB2 can complement LCB2 deficiency, as shown by the appearance of four equally sized colonies on YPD medium without phytosphingosine at 37° C. The V346M (corresponding to V359M in SPTLC2) and I491F (corresponding to I504F in SPTLC2) LCB2 mutants also rescue the absence of endogenous LCB2. However, yeast transformed with the G369V (corresponding to G382V in SPTLC2) or K366T (dominant negative) mutants yields only colonies when endogenous LCB2 is present, demonstrating the failure of these mutants to complement LCB2 deficiency.

To corroborate the loss of canonical SPT activity in vivo, we expressed the corresponding yeast mutants (FIG. 3A) in a heterozygous LCB2 deletion yeast strain (LCB2 is the *S. cerevisiae* orthologue of SPTLC2; the GenBank accession number for the LCB2 sequence is NM_001180370) and performed a tetrad analysis in order to obtain two haploid spores with and two without endogenous LCB2. As expected, all four spores grow at the permissive temperatures of 18° C., regardless of whether they expressed wt or mutant LCB2. At the restrictive temperature (37° C.), spores with (residual) SPT activity will be able to grow, while spores with no or non-functional LCB2 will depend on the external addition of phytosphingosine in order to generate phytosphingolipids and grow (Dunn et al. 2000). Wild-type LCB2 was able to complement the LCB2 deficiency, as apparent from the appearance of four equally sized colonies in the absence of phytosphingosine (FIG. 5). In contrast, but analogous to the dominant negative LCB2 K366T mutation (Gable et al. 2002), yeast spores expressing the G369V mutation (corresponding to G382V in SPTLC2) yielded only colonies when endogenous LCB2 was present, demonstrating the failure of this mutant to complement LCB2 deficiency. The residual activity conferred by the V346M and I491F mutants (corresponding to V359M and I504F respectively in SPTLC2) was sufficient to restore growth at 37° C.; this is in accordance with our biochemical data.

Example 4

Mutant SPT Shows Ambiguity Towards its Amino Acid Substrate

A recent report shows that SPTLC1 mutations in HSAN-I influence the substrate specificity of the SPT enzyme: mutant SPT is able to metabolize L-alanine and to a lesser extent glycine as alternative substrates. This results in the formation of the atypical and neurotoxic sphingoid base metabolites 1-deoxy-SA and 1-deoxymethyl-SA (Zitomer et al. 2009; Penno et al. 2010). The accumulation of these metabolites in the peripheral nerves was postulated to be the underlying cause of HSAN-I (Penno et al. 2010). To study whether SPTLC2 mutations likewise affect the enzymatic affinity of SPT and cause a similar accumulation of these alternative metabolites, the sphingoid base profile of HEK293 cells expressing the mutants was analyzed. In cells stably expressing wt SPTLC2, the amount of 1-deoxy-SA was similar to control cells (FIG. 6a), showing that an increase in SPT activity as such does not alter substrate specificity. Expression of the mutants on the other hand resulted in up to 20-fold higher 1-deoxy-SA levels compared to control cells, with highest levels in HEK cells stably expressing the G382V or I504F mutant enzyme. The generation of 1-deoxymethyl-SA levels in both HEK cells and lymphoblast cells was below detection limits.

To validate if the results obtained in the HEK cells reflect the situation in HSAN-I patients, 1-deoxy-SA levels in lymphoblast cell lines from two HSAN-I patients, carrying respectively the G382V and I504F mutation, were measured. In both cell lines, accumulation of 1-deoxy-SA was observed when compared to unaffected family members or unrelated healthy control individuals (FIG. 6b). This finding is in agreement with our in vitro results and more importantly, shows that the accumulation of 1-deoxy-SA could be physiologically relevant.

Materials and Methods to the Examples

Subjects

For this study, a group of 78 patients was selected with hereditary ulcero-mutilating and sensory neuropathies. The inclusion criteria were described previously in Rotthier et al. 2009. The cohort shows a wide variability of clinical features and different modes of inheritance, but all patients share a progressive distal sensory dysfunction. Prior to enrolment in this study, informed consent from all patients or their legal representatives was obtained by the treating physicians.

Mutation analysis

All DNA samples were amplified using the whole genome amplification kit "GenomiPhi V2 DNA Amplification Kit" (GE Healthcare). The coding regions and exon-intron boundaries up to 100 bp up- and downstream of the exons of SPTLC2 and SPTLC3 were PCR-amplified using oligonucleotide primers designed with the Primer3 and SNPbox software tools (Rozen and Skaletsky 2000; Weckx et al. 2004). Primer sequences are listed in Tables 3 and 4. Mutation screening was performed by direct DNA sequencing of purified PCR fragments using the BigDye® Terminator v3.1 Cycle Sequencing Kit (Applied Biosystems) and separated on an ABI3730x1 DNA Analyzer (Applied Biosystems). The resulting sequences were aligned and analyzed with the novoSNP (Weckx et al. 2005) and SeqMan™II programs. Sequence variants were confirmed by repeated PCR on original DNA samples and bidirectional sequencing.

Parenthood was tested using 15 highly informative short tandem repeats (STRs) distributed throughout the genome (ATA38A05, D1S1646, D1S1653, D1S1360, D2S2256, D3S3037, D4S2382, D4S3240, D7S509, D8S1759, D9S1118, D12S1056, D12S2082, D16S2619 and GATA152H04). STRs were PCR-amplified and PCR fragments were loaded on an ABI3730x1 DNA Analyzer. Genotypes were analyzed using Local Genotype Viewer.

Cloning

The SPTLC2cDNA (NM_004863.2) was amplified and cloned into the Gateway® entry vector pDONR221 (Invitrogen) using the primers

```
SPTLC2_attb1:
                                             (SEQ ID NO: 4)
5'-gggacaagtttgtacaaaaaagcaggctatgcggccggagcccggaggctgct-3';
and SPTLC2_attb2:
                                             (SEQ ID NO: 5)
5'-ggggaccactttgtacaagaaagctgggtccgtcttctgtttcttcatacgtc-3'.
```

The SPTLC2 mutations were introduced by site-directed mutagenesis, using the following primers:

```
SPTLC2_V359M_fw:
                                             (SEQ ID NO: 6)
5'-ccacaggccggggtatggtggagtac-3'

SPTLC2_V359M_rv:
                                             (SEQ ID NO: 7)
5'-gtactccaccataccccggcctgtgg-3'

SPTLC2_G382V_fw:
                                             (SEQ ID NO: 8)
5'-gaacgttcacaaagagttttgttgcttctggaggatatattgg-3'

SPTLC2_G382V_rv:
                                             (SEQ ID NO: 9)
5'-ccaatatatcctccagaagcaacaaaactctttgtgaacgttc-3'

SPTLC2_I504F_fw:
                                             (SEQ ID NO: 10)
5'-ttcctgccaccccaattttttgagtccagagcc-3'

SPTLC2_I504F_rv:
                                             (SEQ ID NO: 11)
5'-ggctctggactcaaaaattggggtggcaggaa-3'.
```

The constructs were recombined in the destination vectorpEF5/FRT/V5-DEST (Invitrogen), fusing the cDNA with a C-terminal V5-tag. All constructs were validated by sequencing. Stable cell lines were generated using the Flp-in host cell line HEK293 following manufacturer's instructions (Invitrogen).

The yeast LCB2 gene together with its own promotor (700 bp upstream of start codon) and own terminator (450 bp downstream of stopcodon) was cloned into the YCplac111 plasmid vector, harboring a LEU2 gene. Mutations and a HA-tag were introduced with site-directed mutagenesis using the following primers:

```
LCB2_HA_fw:
                                             (SEQ ID NO: 12)
5'-gccactacctgagcccgttgtcagcgtagtctgggacgtcgtatgggtaagcgtagtctggga cgtcgtatgggtaagcgtagtctgggacgtcgtatgggtagacacccctccttattacatttc-3'

LCB2_HA_rv:
                                             (SEQ ID NO: 13)
5'-gaaatgtaataaggagggtgtctacccatacgacgtcccagactacgcttacccatacgacgt cccagactacgcttacccatacgacgtcccagactacgctgacaacgggctcaggtagtggc-3'

LCB2_V346M_fw:
                                             (SEQ ID NO: 14)
5'-gcccaactggtcgcggtatgtgtgaaatatttggcg-3'

LCB2_V346M_rv:
                                             (SEQ ID NO: 15)
5'-cgccaaatatttcacacataccgcgaccagttgggc-3'

LCB2_G369V_fw:
                                             (SEQ ID NO: 16)
5'-gtactttcactaagtcgtttgttgctgctggtggttacattg-3'

LCB2_G369V_rv:
                                             (SEQ ID NO: 17)
5'-caatgtaaccaccagcagcaacaaacgacttagtgaaagtac-3'

LCB2_I491F_fw:
                                             (SEQ ID NO: 18)
5'-cttatcctgctactccgctgtttgaatcaagagtaagattctg-3'

LCB2_I491F_rv:
                                             (SEQ ID NO: 19)
5'-cagaatcttactatgattcaaacagcggagtagcaggataag-3'

LCB2_K366T_fw:
                                             (SEQ ID NO: 20)
5'-ctaatgggtactttcactacttcgtaggtgctgctggtg-3'

LCB2_K366T_rv:
                                             (SEQ ID NO: 21)
5'-caccagcagcaccaaacgaagtagtgaaagtacccattag-3'
```

Cell Culture Material and Conditions

HEK293 Flp-in cells were cultivated at 37° C. and 5% $CO_2$ in DMEM supplemented with 10% fetal bovine serum, L-glutamine and penicillin/streptomycin. Lymphoblastoid cell lines were cultured at 37° C. and 5% $CO_2$ in RPMI supplemented with 10% fetal bovine serum, L-glutamine, sodium pyruvate and penicillin/streptomycin. All cell culture media and supplements were from Invitrogen.

Lymphoblastoid Cell Lines

Total blood samples were mixed with 15 ml of FicolPaque and centrifuged for 10 min. After washing, lymphocytes were transformed with Epstein-Barr virus and incubated at 37° C. for 2 h. After centrifugation, the pellet was resuspended in 4 ml RPMI complete medium+1% phytohaemagglutinin. Cells were seeded in a 24-well plate and incubated at 37° C. and 5% $CO_2$ for a minimum of 3 days. Cells were split and supplemented with fresh medium as needed.

Yeast Complementation Assay

The YCplac111 constructs containing wt or mutant LCB2 were transformed (Gietz et al. 2007) in a heterozygous LCB2 deletion strain (BY4743), in which LCB2 has been replaced by a kanamycin resistance gene, and sporulated. The resulting tetrads were dissected to obtain haploid spores which lack endogenous expression of LCB2 and grown on YPD medium with phytosphingosine (15 µM; Avanti Polar Lipids) and 0.1% tergitol at 26° C. After two days, replica plating to different growth media was performed, namely YPD medium at 18° C. and 37° C. (yeast SPT mutants have a thermo-sensitive growth phenotype [Dunn et al. 2000]), synthetic minimal medium without leucine (allowing for selection of transformed spores) and YPD medium with geneticin (selection of LCB2-deficient spores). For each construct, at least six tetrads were analyzed. Unless specified otherwise, media and supplements were from Sigma.

RNA Isolation and mRNA Analysis

Total mRNA was purified using the RNeasy mini kit (Qiagen). DNA inactivation was performed using the Turbo DNA free kit (Ambion) and cDNA synthesis was done with Superscript III first strand synthesis system for RT-PCR (Invitrogen). Expression of SPTLC2 (endogenous and construct) was analyzed using the following primer combinations:

```
SPTLC2_Fw:
                                             (SEQ ID NO: 22)
5'-gagtccagagccaggttttg-3';
and SPTLC2_3'UTR_Rv:
                                             (SEQ ID NO: 23)
5'-ctgagggagcaccaaaaag-3'
(for endogenous SPTLC2 expression);
or
```

-continued

V5_Rv:
(SEQ ID NO: 24)
5'-gagagggttagggataggcttac-3'
(for SPTLC2 construct).

Real time qPCR (RT-qPCR) reactions were performed in triplicate with 10 ng cDNA in SYBR Green I mix (Applied Biosystems) and run on ABI Prism 7900 HT Sequence Detection System (Applied Biosystems). Primers were validated for specificity and amplification efficiency. RT-qPCR data were normalized according to the method described by Vandesompele et al. 2002. The relative expression levels were used to normalize the data of the Fumonisin B1 block assay, the in vitro SPT activity assay and the 1-deoxy-SA quantification.

Fumonisin B1 Block Assay

This assay was performed as described in Penno et al. 2010. Briefly, Fumonisin B1 (Sigma) was added to the media of exponentially growing cells in a final concentration of 10 μg/ml. As a negative control, the SPT inhibitor myriocin (10 μg/ml, Sigma) was added together with Fumonisin B1. 24 hours after Fumonisin B1 addition, cells were washed twice with PBS, harvested and counted (Coulter® Z2, Beckman Coulter). Next, the cells were subjected to lipid extraction under basic conditions (see below). Sphingoid bases were quantified by LC-MS. Synthetic C 17 sphingosine (Avanti Polar Lipids) was added to each sample as an internal extraction standard.

In Vitro Radioactive-Based SPT Activity Assay

SPT activity was measured using the radioactivity-based assay described by Rütti et al. 2009. In brief, 400 μg total cell lysate, 50 mM HEPES (pH 8.0), 0.5 mM L-serine, 0.05 mM Palmitoyl-CoA, 20 μM Pyridoxal-5'-phosphate, 0.2% sucrose monolaureate (all from Sigma) and 0.1 μCi L-[U-14C] serine (Amersham) were mixed and incubated at 37° C. In the control reaction, SPT activity was specifically blocked by the addition of myriocin (40 μM, Sigma). After 60 min, the reaction was stopped and lipids were extracted according to the method of Riley et al. 1999 (see below).

Lipid Extraction and Hydrolysis

Total lipids were extracted from cells or plasma and extracted according to the method of Riley et al. 1999. For acid hydrolysis, the dried lipids were resuspended in 200 μl methanolic HCl (1N HCl/10M water in methanol) and kept at 65° C. for 12-15 hours. The solution was neutralized by the addition of 40 μl KOH (5M) and subsequently subjected to base hydrolysis, which was performed as follows: 0.5 ml extraction buffer (4 vol. 0.125M KOH in methanol+1 vol. chloroform) was added to the solution. Subsequently, 0.5 ml chloroform, 0.5 ml alkaline water and 100 μl 2M ammonia were added in this order. Liquid phases were separated by centrifugation (12,000 g, 5 min). The upper phase was aspirated and the lower phase washed twice with alkaline water. Finally, the lipids were dried by evaporation of the chloroform phase under N2 and subjected to liquid chromatography-mass spectrometry (LC-MS) analysis.

Extracted lipids were solubilized in 56.7% methanol-33.3% ethanol-10% water and derivatized with ortho-phtaladehyde. The lipids were separated on a C18 column (Uptispere 120 Å, 5 μm, 125×2 mm, Interchim, France) fluorescence detector (HP1046A, Hewlet Packard) followed by detection on a MS detector (LCMS-2010A, Shimadzu). APCI (atmospheric pressure chemical ionisation) was used for ionization. Non-natural C17 sphingosine (Avanti Polar Lipids) was used as internal standard. Retention times were as follow: $C_{17}SO$ (int.STD): 6 min; sphingosine: 7.5 min; 1-deoxysphingosine: 9 min; 1-deoxymethylsphingosine: 10.5 min; sphinganine: 10.5 min, 1-deoxymethylsphinganine: 13 min; 1-deoxysphinganine: 13.5 min. MS data were analyzed using LCMS solution (Shimadzu) and MS Processor v.11 (ACD Labs).

Statistics

The two-tailed unpaired Student's t-test was used for statistical analysis. Error bars (standard deviation) and p-values (Student t-test) were calculated based on three independent experiments.

TABLE 1

| Patient | Origin | Mutation | Familial history | Onset | Presenting symptoms | Disease duration | Ulcerations | Osteomyellis |
|---|---|---|---|---|---|---|---|---|
| CMT-747.I:1 | Austria | c.1075G > A p.V359M | IC | 52 y | Ulceration and ampulation great toe R | 27 y | + (loes) | + |
| CMT-1044.I:2 | Germany | c.1145G > T p.G382V | D | 37 y | Dysesthesia and sensory loss distal UL and LL | 35 y | – | + (thumb R) |
| CMT-1117.II:1 | Austria | c.1145G > T p.G382V | D | 38 y | Sensory loss in feet | 8 y | – | – |
| CMT-1117.I:2 | Austria | c.1145G > T p.G382V | D | ? | Asymptomatic | ? | – | – |
| CMT-535.II:1 | Czech Republic | c.1510A > T p.I504F | IC (de novo) | 5 y | Gait difficulties, foot deformities | 9 y | + (LL) | + |

| Patient | Amputations | Sensory dysfunction | Autonomic dysfunction | Distal weakness | NCS | Additional |
|---|---|---|---|---|---|---|
| CMT-747.I:1 | + | + (distal LL) | – | – | Axonal/ intermediate sensorimotor | Sural nerve biopsy: axonal neuropathy in particular of unmyelinated fibers |
| CMT-1044.I:2 | – | + severe distally panmodal with dysesthesia | – | + UL (0-3/5) and LL (0/5) | Axonal/ intermediate sensorimotor | Scoliosis, focal epilepsy, Brisk Reflexes UL; Claw hand R > L |

TABLE 1-continued

|  |  |  |  |  |  |  |
|---|---|---|---|---|---|---|
| CMT-1117.II:1 | − | + distally for touch and vibration | − | + LL (2/5) | Axonal sensorimotor | — |
| CMT-1117.I:2 | − | + distally LL for vibration | − | + LL (5-/5) | Axonal sensorimotor | Type 2 diabetes (onset 71 y) |
| CMT-535.II:1 | − | + | + | + (LL) | Intermediate sensorimotor | — |

TABLE 2

| Patient | Age | | Median motor | | Ulnar Motor | | Peroneal motor | | Tibial motor | | Median sensory | | Ulnar sensory | | Sural sensory | |
|---|---|---|---|---|---|---|---|---|---|---|---|---|---|---|---|---|
| | | | Amp | CV | Amp | CV | Amp | CV | Amp | CV | Amp | CV | Amp | CV | Amp | CV |
| Normal values ≥ | | | 4.0 | 49.0 | 4.0 | 49.0 | 3.0 | 41.0 | 3.0 | 41.0 | 7.0 | 46.0 | 2.0 | 47.0 | 1.0 | 44.0 |
| CMT-747.I:1 | 79 y | R | 9.7 | 44.3 | — | — | 0.1 | 35.7 | — | — | A | A | — | — | — | — |
| | | L | 8.4 | 51.0 | — | — | 0.1 | 23.3 | — | — | 0.9 | 35.2 | — | — | — | — |
| CMT-1044.I:2 | 72 y | R | 0.1 | 34.0 | 0.5 | 37.0 | A | A | A | A | A | A | A | A | A | A |
| CMT-1117.II:1 | 44 y | R | 6.2 | 55.0 | — | — | A | A | A | A | A | A | 0.4 | 38.0 | A | A |
| CMT-1117.I:2 | 72 y | R | 9.9 | 47.0 | 5.6 | 51.0 | 3.0 | 42.0 | — | — | — | — | — | — | 2.7 | 33.0 |
| CMT-635.II:1 | 14 y | R | 3.8 | 25.0 | 2.9 | 50.0 | A | A | A | A | A | A | A | A | A | A |
| | | L | 2.0 | 29 | 2.1 | 53 | A | A | A | A | — | — | — | — | — | — |

TABLE 3

Exon primers used for PCR and direct sequencing of SPTLC2.

| | Forward primer (5'-3') | SEQ ID NOs | Reverse primer (5'-3') | SEQ ID NOs |
|---|---|---|---|---|
| Exon 1 | gcagccatttccggtttc | 25 | ggattgcccagcggatgg | 26 |
| Exon 2 | ttacaggtgtgagccagtgc | 27 | tgtgcaaaaatactaagatttc | 28 |
| Exon 3 | cacaatcttgcacgtaatgaaa | 29 | cctcagctgctactcctattttg | 30 |
| Exon 4 | tctgcttccttttgtgtcacc | 31 | tcagaaaaacaaagcattcttca | 32 |
| Exon 5 | agtctgaaaaggacacaacaca | 33 | gctcactctgactgcttttcaa | 34 |
| Exon 6 | tgatcactgtgctgttgtgc | 35 | aagactggaccggaagaacat | 36 |
| Exon 7 | tgaggcatggtttctgaatg | 37 | tgctgactctgtttccaggt | 38 |
| Exon 8 | acttcagcctggacaatgga | 39 | gagcctaaaccagaggcaaa | 40 |
| Exon 9 | gaccatgttggttgaccttgt | 41 | gtccatggaaaccacacacc | 42 |
| Exon 10 | aaatattttatggtgaaatggaaaa | 43 | tggcatatgtaccaaatgaagg | 44 |
| Exon 11 | gcctgcatcaccaaagagtt | 45 | cactgtcaccccctctgtct | 46 |
| Exon 12 | cctgccgaaggataatcttg | 47 | gcaaaggaaggattagaagca | 48 |

TABLE 4

Exon primers used for PCR and direct sequencing of SPTLC3.

| | Forward primer (5'-3') | SEQ ID NOs | Reverse primer (5'-3') | SEQ ID NOs |
|---|---|---|---|---|
| Exon 1 | caaacggtgcagagacc | 49 | aacccttcataagatgaactcta | 50 |
| Exon 2 | taacaggagaatgctaacctt | 51 | cactttagagaggagtaggc | 52 |

TABLE 4-continued

Exon primers used for PCR and direct sequencing of SPTLC3.

| | Forward primer (5'-3') | SEQ ID NOs | Reverse primer (5'-3') | SEQ ID NOs |
|---|---|---|---|---|
| Exon 3 | agataaccttctacctctgttctaa | 53 | ttgtcatctagtggccat | 54 |
| Exon 4 | gaatcgtgcataatcctgg | 55 | agagacagacacaaggaat | 56 |
| Exon 5 | aatcttggccttgttgaaa | 57 | tctaacaaggacctactcaga | 58 |
| Exon 6 | ctgtccccacaagttgtttt | 59 | gtcaccttgaagagcagaa | 60 |
| Exon 7 | tttaggtctgagtgtgaacata | 61 | tctgtttagctaggaaaggtga | 62 |
| Exon 8 | ggagggtatttgttagtta | 63 | ggtgtggtgaactgaattg | 64 |
| Exon 9 | agggatgggactagatgta | 65 | gggagattaatgaggcagaa | 66 |
| Exon 10 | atgcttgccaagttgac | 67 | cataatctaacgcctgtgc | 68 |
| Exon 11 | catattcctttttgtcag | 69 | taaataacccaagagaaac | 70 |
| Exon 12 | gctattaatctgggctctg | 71 | ggagaaatccatttatattccttg | 72 |

REFERENCES

Auer-Grumbach M, De Jonghe P, Verhoeven K, Timmerman V, Wagner K, Hartung H P, et al. Autosomal dominant inherited neuropathies with prominent sensory loss and mutilations: a review. Arch Neurol 2003; 60: 329-34.

Auer-Grumbach M. Hereditary sensory neuropathies. Drugs Today 2004; 40: 385-94.

Ausubel F M, Brent R, Kingston R E, Moore D D, Seidman J G, Smith J A and Struhl K. Series Editor: Virginia Benson Chanda. Current Protocols in Molecular Biology 2003, John Wiley & Sons.

Bejaoui K, Wu C, Scheffler M D, Haan G, Ashby P, Wu L, et al. SPTLC1 is mutated in hereditary sensory neuropathy, type 1. Nat Genet 2001; 27: 261-2.

Bouhouche A, Benomar A, Bouslam N, Chkili T, Yahyaoui M. Mutation in the epsilon subunit of the cytosolic chaperonin-containing t-complex peptide-1 (Cct5) gene causes autosomal recessive mutilating sensory neuropathy with spastic paraplegia. J Med Genet 2006a; 43: 441-3.

Bouhouche A, Benomar A, Bouslam N, Ouazzani R, Chkili T, Yahyaoui M. Autosomal recessive mutilating sensory neuropathy with spastic paraplegia maps to chromosome 5p15.31-14.1. Eur J Hum Genet 2006b; 14: 249-52.

Cox, J. J., Reimann, F., Nicholas, A. K., Thornton, G., Roberts, E., Springell, K., Karbani, G., Jafri, H., Mannan, J., Raashid, Y., Al-Gazali, L., Hamamy, H., Valente, E. M., Gorman, S., Williams, R., McHale, D. P., Wood, J. N., Gribble, F. M., Woods, C. G. An SCN9A channelopathy causes congenital inability to experience pain. Nature 444: 894-898, 2006.

Dawkins J L, Hulme D J, Brahmbhatt S B, Auer-Grumbach M, Nicholson G A. Mutations in SPTLC1, encoding serine palmitoyltransferase, long chain base subunit-1, cause hereditary sensory neuropathy type I. Nat Genet 2001; 27: 309-12.

Dawkins, J. L., Brahmbhatt, S. B., Auer-Grumbach, M., Wagner, K., Hartung, H. P., Verhoeven, K., Timmerman V, De Jonghe P, Kennerson, M. L., LeGuern, E. et al. (2002). Exclusion of serine palmitoyltransferase subunit 2 (SPTLC2) as a common cause for hereditary sensory neuropathy. Neuromusc. Disord. 12, 656-658.

Dunn, T. M., Gable, K., Monaghan, E., and Bacikova, D. (2000). Selection of yeast mutants in sphingolipid metabolism. Methods Enzymol. 312, 317-330.

Dyck P J. Neuronal atrophy and degeneration predominantly affecting peripheral sensory and autonomic neurons. In: Dyck P J, Thomas P K, Griffin J W, Low P A, Poduslo J F, editors. Peripheral neuropathy. 3rd edn., Philadelphia: W.B. Saunders; 1993. p. 1065-93.

Einarsdottir E, Carlsson A, Minde J, Toolanen G, Svensson O, Solders G, et al. A mutation in the nerve growth factor beta gene (NGFB) causes loss of pain perception. Hum Mol Genet 2004; 13: 799-805.

Gable, K., Han, G., Monaghan, E., Bacikova, D., Natarajan, M., Williams, R., and Dunn, T. M. (2002). Mutations in the yeast LCB1 and LCB2 genes, including those corresponding to the hereditary sensory neuropathy type I mutations, dominantly inactivate serine palmitoyltransferase. J. Biol. Chem. 277,10194-10200.

Gietz, R. D. and Schiestl, R. H. (2007). High-efficiency yeast transformation using the LiAc/SS carrier DNA/PEG method. Nat. Protoc. 2, 31-34.

Gut LG. (2001) Automation in genotyping of single nucleotide polymorphisms. Hum.

Hornemann, T., Wei, Y., and von Eckardstein, A. (2007). Is the mammalian serine palmitoyltransferase a high-molecular-mass complex? Biochem. J. 405, 157-164.

Indo Y, Tsuruta M, Hayashida Y, Karim M A, Ohta K, Kawano T, et al. Mutations in the TRKA/NGF receptor gene inpatients with congenital insensitivity to pain with anhidrosis. Nat Genet 1996; 13: 485-8.

Kok C, Kennerson M L, Spring P J, Ing A J, Pollard J D, Nicholson G A. A locus for hereditary sensory neuropathy with cough and gastroesophageal reflux on chromosome 3p22-p24.Am J Hum Genet 2003; 73: 632-7.

Kurth, I., Pamminger, T., Hennings, J. C., Soehendra, D., Huebner, A. K., Rotthier, A., Baets, J., Senderek, J., Topaloglu, H., Farrell, S. A. et al. (2009). Mutations in FAM134B, encoding a newly identified Golgi protein, cause severe sensory and autonomic neuropathy. Nat. Genet. 41, 1179-1181.

Lafreniere R G, MacDonald M L, Dube M P, MacFarlane J, O'Driscoll M, Brais B, et al. Identification of a novel gene (HSN2) causing hereditary sensory and autonomic neuropathy type II through the Study of Canadian Genetic Isolates. Am J Hum Genet 2004; 74: 1064-73.

Meggouh F, Bienfait H M, Weterman M A, de Visser M, Baas F. Charcot-Marie-Tooth disease due to a de novo mutation of the RAB7 gene. Neurology 2006; 67: 1476-8.

Nollau P, Wagener C. (1997) Methods for detection of point mutations: performance and quality assessment. IFCC Scientific Division, Committee on Molecular Biology Techniques. Clin Chem., 43(7): 1114-28.

Penno, A., Reilly, M. M., Houlden, H., Laura, M., Rentsch, K., Niederkofler, V., Stoeckli, E. T., Nicholson, G., Eichler, F., Brown, R. H., Jr. et al. (2010). Hereditary sensory neuropathy type 1 is caused by the accumulation of two neurotoxic sphingolipids. J. Biol. Chem. 285, 11178-11187.

Riley, R. T., Norred, W. P., Wang, E., and Merrill, A. H. (1999). Alteration in sphingolipid metabolism: Bioassays for fumonisin- and ISP-I-like activity in tissues, cells and other matrices. Natural Toxins 7, 407-414.

Rotthier, A., Baets, J., De Vriendt, E., Jacobs, A., Auer-Grumbach, M., Levy, N., Bonello-Palot, N., Kilic, S. S., Weis, J., Nascimento, A. et al. (2009). Genes for hereditary sensory and autonomic neuropathies: a genotype-phenotype correlation. Brain 132, 2699-2711.

Rozen, S. and Skaletsky, H. (2000). Primer3 on the WWW for general users and for biologist programmers. Methods Mol. Biol. 132, 365-386.

Rutti, M. F., Richard, S., Penno, A., von Eckardstein, A., and Hornemann, T. (2009). An improved method to determine serine palmitoyltransferase activity. J. Lipid Res. 50, 1237-1244.

Sambrook J., Fritsch E. and Maniatis T. (1989) Molecular cloning: a laboratory manual. Cold Spring Harbor Laboratory Press, Cold Spring Harbor, N.Y., USA.

Slaugenhaupt S A, Blumenfeld A, Gill S P, Leyne M, Mull J, Cuajungco M P, et al. Tissue-specific expression of a splicing mutation in the IKBKAP gene causes familial dysautonomia. Am J Hum Genet 2001; 68: 598-605.

Syvanen A. C. (2001) Accessing genetic variation: genotyping single nucleotide polymorphisms. Nat. Rev. Genet. 2: 930-942.

Vandesompele, J., de Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol. 3, 1-12

Verhoeven K, De Jonghe P, Coen K, Verpoorten N, Auer-Grumbach M, Kwon J M, et al. Mutations in the small GTP-ase late endosomal protein RAB7 cause Charcot-Marie-Tooth type 2B neuropathy. Am J Hum Genet 2003; 72: 722-7.

Verhoeven K, Timmerman V, Mauko B, Pieber T R, De Jonghe P, Auer-Grumbach M. Recent advances in hereditary sensory and autonomic neuropathies. Curr Opin Neurol 2006; 19: 474-80.

Verpoorten N, Claeys K G, Deprez L, Jacobs A, Van Gerwen V, Lagae L, et al. Novel frameshift and splice site mutations in the neurotrophic tyrosine kinase receptor type 1 gene (NTRK1) associated with hereditary sensory neuropathy type IV. NeuromusculDisord 2006b; 16: 19-25.

Verpoorten N, De Jonghe P, Timmerman V. Disease mechanisms in hereditary sensory and autonomic neuropathies. Neurobiol Dis 2006a; 21: 247-55.

Wang, E., Norred, W. P., Bacon, C. W., Riley, R. T., and Merrill, A. H., Jr. (1991). Inhibition of sphingolipid biosynthesis by fumonisins. Implications for diseases associated with *Fusarium moniliforme*. J. Biol. Chem. 266, 14486-14490.

Weckx, S., De Rijk, P., Van Broeckhoven, C., and Del Favero, J. (2004). SNPbox: web-based high-throughput primer design from gene to genome. Nucleic Acids Research 32, W170-172.

Weckx, S., Del Favero, J., Rademakers, R., Claes, L., Cruts, M., De Jonghe, P., Van Broeckhoven, C., and De Rijk, P. (2005). novoSNP, a novel computational tool for sequence variation discovery. Genome Res. 15, 436-442.

Zitomer, N. C., Mitchell, T., Voss, K. A., Bondy, G. S., Pruett, S. T., Garnier-Amblard, E. C., Liebeskind, L. S., Park, H., Wang, E., Sullards, M. C. et al. (2009). Ceramide synthase inhibition by fumonisin B1 causes accumulation of 1-deoxysphinganine: a novel category of bioactive 1-deoxysphingoid bases and 1-deoxydihydroceramides biosynthesized by mammalian cell lines and animals. J. Biol. Chem. 284, 4786-4795.

Staud R, Price D D, Janicke D, Andrade E, Hadjipanayis A G, Eaton W T, Kaplan L, Wallace M R. Two novel mutations of SCN9A (Nav1.7) are associated with partialcongenital insensitivity to pain. Eur J Pain. 2010 Aug 6.

Cox J J, Sheynin J, Shorer Z, Reimann F, Nicholas A K, Zubovic L, Baralle M, Wraige E, Manor E, Levy J, Woods C G, Parvari R. Congenital insensitivity to pain:novel SCN9A missense and in-frame deletion mutations. Hum Mutat. 2010Sep; 31(9):E1670-86.

Kurban M, Wajid M, Shimomura Y, Christiano A M. A nonsense mutation in the SCN9A gene in congenital insensitivity to pain. Dermatology. 2010; 221(2):179-83.

What is claimed is:

1. A method of detecting a mutation in a SPTLC2 gene, the method comprising:
   (a) obtaining a sample from a subject;
   (b) contacting a SPTLC2 nucleic acid in a sample from the subject with a detectably labelled oligonucleotide that specifically hybridizes to a SPTLC2 nucleic acid comprising a variant at a position corresponding to a position selected from the group consisting of position 1145, 1075 and 1510 relative to the ATG start codon beginning at position 189 of SEQ ID KO:2, wherein the detectably labelled oligonucleotide comprises i) a nucleotide sequence comprising a variant in a SPTLC2 gene selected from the group consisting of: c.1075G>A, c.1145G>T, and c.1510 A>T, or ii) the complementary strand of the nucleotide sequence of i), and wherein the oligonucleotide hybridizes to the variant SPTLC2 sequence but not the wildtype SPTLC2 sequence; and
   (c) detecting hybridization of the oligonucleotide with the SPTLC2 nucleic acid under hybridization conditions, and wherein the oligonucleotide will specifically hybridize to the sequence comprising the variant but not to the wildtype SPTLC2 sequence, and wherein detecting hybridization is indicative of a mutation in a SPTLC2 gene.

2. The method according to claim 1, further comprising detecting the presence or absence of a nucleic acid variant in at least one other gene in the sample from the subject.

3. The method according to claim 2, wherein the other gene is selected from the group consisting of SPTLC1, RAB7A, WNK1/HSN2, IKBKAP, FAM134B, NTRK1, NGFβ, and CCT5.

4. The method according to claim 1, wherein the method further comprises use of at least one of the following methods: sequencing, PCR, primer extension, multiplex ligation-dependent probe amplification (MLPA), oligonucleotide ligation assay (OLA), restriction site analysis or high-resolution melting (HRM) analysis for mutation scanning.

5. The method of claim 1, wherein the variant is c.1075G>A.

6. The method of claim 1, wherein the variant is c.1145G>T.

7. The method of claim 1, wherein the variant is c.1510A>T.

8. The method of claim 1, wherein the detectably labeled oligonucleotide is labelled with a fluorescent, chemiluminescent, enzymatic, radioactive, or chemical label.

* * * * *

SEQUENCE LISTING

```
<160> NUMBER OF SEQ ID NOS: 88

<210> SEQ ID NO 1
<211> LENGTH: 109841
<212> TYPE: DNA
<213> ORGANISM: Homo sapiens

<400> SEQUENCE: 1
cttggccgag accggtcctc tgcggagagg gccccgccct ctgtgaaggc ccgcccggga      60 attgcggcg gcgctgcagc catttccggt ttcggggagg tgggtggggt gcggagcggg     120
acttggagca gccgccgccg ctgccaccgc ctacagagcc tgccttgcgc ctggtgctgc     180
```

```
caggaagatg cggccggagc ccggaggctg ctgctgccgc cgcacggtgc gggcgaatgg      240
ctgcgtggcg aacggggaag tacgaacgg gtacgtgagg agcagcgctg cagccgcagc      300
cgcagccgcc gccggccagg tacgaggggc ccgcgcggcg gggccggggt ggcggtgtgg      360
actggcggag gggcggccgg gcggggcgag gtctccgggc catccgctgg gcaatccgcg      420
gggcgggcgc cgttcgcagg tgtgggcggc agtgtccggc cgctggcccg acctccacga      480
gcctggaggc tcaaggacgg ctcggggact ccccacctct ccgcgcctgg aggtcttact      540
cccggagctc tgggttctgc tcagagctcc gggtactttt ctctgcccca ttctgccaga      600
agtgtgtgct gtccccaggg gaagcgatga gggccccttc ggactccagt gggagccgcc      660
caagggctcc ggagggtccc ttctcaaacc cctgaggtta ttgcttcctt ttaaagtcct      720
gcagtcgtcc aaagaaaacc acccatgggg tccttaagaa gcaaagaaaa ttaggcggtg      780
gtgtcagatg gaaacacacc cagcctctcc caaccacatt ctggactacc acgttcagtc      840
cccaaccagg acattggtcc atagatctgg cagggaatcc aagctggtcc ctcgaaagca      900
tcattctctt aactctgccg gtggtgagac tctaccccag gctccaggtt ggattaggtg      960
gccccttcga ccctttcctg aacacgagtg ctatcacaca aggggattgt ttagcctggt     1020
ggtgacttgc gatgactcta tactaattaa ccatgctgaa tcatcaacca agttcaggca     1080
gttctaaaat attttgaaaa gttctaaatt caagacaatg cttattatca accttacagt     1140
ggtctggact gacagatatt ctgttgaaat gtgtttttaa agatgagctg gttaaaaaga     1200
tgcaagatcg gtgttcctgg aagagagtgt tgcgataatt ttgcagttga ctttaatacg     1260
tttaagtctt gtacagatat taaggaacgc ttagaaagta ctctgtttcc ctttagcggg     1320
agtgtgactg ttgcagtttg ataggatggt gatcttaatt tggctttaac ataactactc     1380
cccagatgag tagttatgat ggataggtct gttactgttt gctgcgaagc agaaaataaa     1440
gcattttccc aggtcatgtt gagatattga gactgagttg aggggaaaaa taagtaaagc     1500
agacttgacc tcccctgaag ttgtaaggtg tcaaagcgaa gtaatacaca gatcaaaaga     1560
tttgttttca cttttaaaga aataattgtg tgagggagga agtgataaca gtcagctcat     1620
tataagcagt ggaatagttt gtcgttttcc tagcaatgta aacgacttat aagacaaaat     1680
tgttgtggta tagaatgtaa tagggaaatt taacgggtag gagttagaaa atacatttgc     1740
aggtgaattt cattgaggta tgatttttt ttttgttttg ttttgttt ttttttcag         1800 acagttttgc tcttgtcacc caggctggag tgcaatggcg cgatctcggc tcactgcagc     1860
ctccaccccc tgggttcaag cgattctcct gccccagcct cccgagtagc tgggattaca     1920
ggcgcccgtc atcacgcccg gctaaatttt gtatttttat tagagatggg gtttcaccat     1980
gttggccagg ttggtctcga actcctgacc tcaggtgatt ggcctgcctt ggcctccaaa     2040
agtgctggga ttacaggcgc accaggccga ggtatgattt ttttgtttt tttggttttt     2100 tttgagatgg agtctcgctc tgtcgcccag gctggagtgc agtggcgcga tctcggctca     2160
ctgcaagctc tacctcccag gttcacgcca ttctcctgcc tcagcctccc aagtagctgg     2220
gcctacaggc acccgccacc acgcccggct aattttttgt attttagta gatacggggt     2280 ttcactgtgt tagccaggat ggtcttgatt tcctgacctc gtgatccgcc tgcctcggcc     2340
tcccagagtg ctgggattac gggtgtgagc cactgcacct ggccggtatg attttttaaa     2400
atgaaaaagg aagtcaagag aaaggtgttc acacttcagc gttgctttgt gttcaaatgc     2460
ttctttcaat ccctatgagt tatgttcaga tttagtagga aatcaaggac ctttctccca     2520
taatctctaa caatttagca tttatagaat gatatttctt cagagcttgc caactaataa     2580
```

```
ggtgaagaaa tatcaaggta ctaacatgac attttaaaat ctgtatgaat aacatttggt    2640
tgacttttgg ggacatgttt tgtaaaagtt tcactcaagg cacattggtg gcatttggaa    2700
gaacggtctg ttggaatgct gtgagggctg cagtatccct tctagaaaac tacttctcac    2760
cagtattttt aatacagact tcagatctgg agctttctac actctcagat ggaggaatat    2820
tgtctgtgaa tattttctt tcttatacaa agagagatc ttggtaacta catgagagca     2880
atacaatatc ttaacatttt ttaaaagttg ttttcatttt taattaaagc gatgtgcttg    2940
tgctccaacc tctacctatc tttccctct ttctgggggg gaaatgttgc caactgtgcc    3000
atcaaaaata cgcatacagc tgtgtgtcat gcttttacta aaatatgaat ttagagtata    3060
acattgttga gatgtaaatt ctttcctca catctcccac catgtctttt aatgaacagg     3120
agagaagtca gaaacgtcta ggatcacttt acactctcaa gagtatgttt ctgtgcttga    3180
agagatgaat gaatgtgtat agtaaaagaa caactcttgg atttgggttt agaatttgat    3240
gagctagatc tgtgttaag gagttatgaa acaatcacac attgctgttt agtgatgaca     3300
gtagacacac agttttcaca atagtaacag ttgaacaata gagcagtaat ttttcctctc    3360
tgctattcag atgagtggga ggagcacaaa cctttatttg aggtaaggtg tggcaatttg    3420
cccgagggaa acttttacat tagcattgga aagaaccttt gggagtttat ttaattcagt    3480
cctttatctc tttgtaggag tttattaaaa tcagtcttga tagaaaattc tgtactgttt    3540
ttaaagatct ccaggggatt tgcagcaagt ttttctctat agcaaattgg attattattc    3600
catgatctta attaccaaat ttcttcctgt ggatttaaca tttgatgaaa taaatgccat    3660
gttttggttg cacctgaaat atagtagttt gtttgtgtgt ttgttttaa aacttcacgt      3720 taacagctct ttttaaaaga gcttccattt ctttatagaa gttttgagat ttaggttttc     3780
cttttacttt cctgagttag ttaataagtg tgaaagaaaa aaagttatct accttttgaga   3840 cagtttttgac cctaactttt ttccctttgg gtgtagtttt aatgagatat tagaaggatg    3900
agagctctct ggcttacaga ataaaaaatt ctatctcaag gaattggggc aaaagttgtg    3960
ttcttatgtt aaataataag caaagtagaa agaacaaagt gttagtcttg cttcttagga    4020
ggaggcaaat aaataactaa taaagctggt ttactaaata gctactagct tttgtttcca    4080
ctgagggaga aacagtaact gggggtttat atgtgatagt taaggaaaag gagacgatag    4140
ttatgaggct agaacagtag aaatagttag aatagtcata tatctattta gatttagcag    4200
atcctgataa gatacctcag atacctgaag gcttttcaga ataatgtaa tttacaactt     4260 ggaggacaag attttcattt cagttttcac tctaagggga agcatatctt gattcttaca    4320
tagctgcatc tgaagaattc cagagttatt tgagatactc aggaattttc tttaacagga    4380
attcttggga aatgtgtaag cagctatgtt cttaagatag tattttagaa ctaggatgtt    4440
cagaaaagtc agacttgccc acttttagg gtttgcccat gtgccataga aatttgcacc      4500
gctttgagca agacagttaa ttggttgatt taattagatt cagttttgg aagaagaag      4560 cagtgtttat tggtagaata ggcaattcag agggatgggt agaggcactg tttgcattct    4620
gagtgggtgt gccatacttg attaaataaa tggtttgtgg actcaaagtc agttcccttc    4680
tgggtagttt ctgagaagct tctgtaatat aattcacaat ttgtgaccga taaaaaagta    4740
agtcctttgc tcttgaccca tttactgtta gaaaattat cttaagtttg tctttaagac     4800
tactttttat tgcaaagctt gaggcagcta ttcttccttt tttaaaaaaa taatttttac    4860
ttctcattat agaaataata catgtttaat gtgggatcat aaaacattga gataatctct    4920
```

```
gcgttaggtt ttttttttttt tgagacggag tctcactctg tcgcccaggc tggagtgcag    4980
tggcgccatc tcagttcact gcagcctcca cctcccgggt tcaagcgatt ctccagcctc    5040
agcctcctga gtagctggga ttacaggcat gcgccaccac gcctggctga ttttttgcatt   5100
tgtagtagag acaaggtttc acagtgttgg ccaggctggt ctcgaactcc tgacctcagg    5160
tgatccacct gcctccgcct cccaaagtgc tgggattaca ggcgtgagcc accacgccta    5220
gccggaggtt tgttttttaa tgtggtctat tgtaaatcca tctgctactt tccgttaatt    5280
tcttttcttt ctttttttttt ttttttttgg cgagataggg tctcgctcca gcctggcctg   5340
cagtagcaca gtcatagctt actgcggcct caacttctcg ggctcaagcg atcctcccat    5400
ctcagcctcc caagtagctg gtccacagg  tgtgcaccac tacagtgggc taatttttttt   5460
ttttgagaca gagtcttgct ctgtcaccca ggctggagtg cagtggcgcg atcttggctc    5520
actgcaagct ctacttccca ggttcacacc attctcctgc ctcagcctcc cgagtagctg    5580
ggactacagg tgctcaccaa cacacccggc taattttttt tttttttttg tattttttagt   5640
agagacaggg tttccccatg ttagccagga tggtctcgct ctcctgacct tgtaatccgc    5700
ctgcctcagt ctcccaaagt gctggaatta caggcttgag ccaccatgcc tggccttttt    5760
tttttttttt ttttgtagag atgggtctta ctatgttccc caggctagtc tcttttttac    5820
ttaaacaaac aaacaaaaat aaataaaaat atatatatat aaagagagag ggagacagag    5880
agagagggag acagagtctc actatgttgc ccaggctgat ctcaaactgt tgggtacaat    5940
cgatcctcct gccttggcct cctgaagtgc tgagattata ggtgtgagcc accgcaccca    6000
gccacccagg ctggtctcag actcctgacc acaagcatcc tcctgcttca gcctaccaaa    6060
gtgctgggat tacagccact gtagcagact attttgtgat aatttctaag tacagtgaaa    6120
tatgcggttg tactgatact atgggtgtga tccagtctta ctccaaaaaa taggtattaa    6180
gggctgggca cagtggctca tacctgtaat cccagcacta agggaagcca aggtgtaagg    6240
attgcttgag cccaggagtt caagatcagc ctgggcaacg tggcgagacc ccatctctat    6300
ttaattaaaa aataataagg tatatgacca ggtaccgtgg ctcacgcctg taatcccagc    6360
actttgggaa gccgagatgg gcggatcact tgaggtcagg agtttgagac cagcctggcc    6420
aacatggtga acccccgtct ctactaaaaa tgtaaaaatt agccgggtgt ggtggtgtgt    6480
gcctataatc ccagctactc tgggagtctg aggtagtaga atcgcttgaa cccaggaggt    6540
ggaagttgca gtgagccaag atggtgccac tgcacttcag cttgggcgac agtgagactc    6600
tgtctcaaca aaacaaaaca aaacaaaacc tcagttagat accatttcac accactagga    6660
ttgctaaaat aataaaccag gtattaagtg ttcatgagga tatagagaaa ttagaatcct    6720
gatacattgc tggtgggatt ataaaatgat gcagccactt taggaaacag ttaaacatag    6780
agttagcatg tggcccagta attctactcc caagaaaaat gaaacatatg ttcctgcaga    6840
aacttgtata ttaattataa tagcagcatt gttgattgat tgattgattg attcagggtg    6900
ttactgttac ccaggctggc aggacatggc tcaccgcagc ctccacctcc tgggctcaat    6960
caatcctccc acctcagcct cccaagtatc tgggactgca ggcatatgcc accatgagtg    7020
gcaaaatttt ttttttttttg agacagagtc tcactccgtt gcccaggctg ggtgcagtg   7080
tggctcactg caacctccac cccactggtt caagcagttc tcctgcctcc gccttccgag    7140
tagctgggac tacaggcaca tgccaccacg cccagctaat ttttttatatt tttagtagag    7200
atggggtttc accatgttgg tcaggctggt ctcgactcc  tgacctaagt gatccatccg    7260
cttcggactt ccaaagtgct ggaattacag gcgtgaacca ctgtgtctag ccccacgtta    7320
```

```
tttataatag ccaaaaagta gaaacaatcc aaatgtctat caactgatga gtagataaaa    7380
tatggtatat ccatataaaa ggatattatt cagcaatact actgaaggaa tgcagtacta    7440
atacatgcag gagaatacta cattgtttat ggccatgtgt ttatatagtg aaagtattta    7500
aaaatacagg ggaatgataa acaccaaatt cccaattctt ctgaggagga aaggaaatat    7560
agcatttccc caggacagac ttcttaaaag gattggagaa ctacttaaac atgtcagatc    7620
ttgacactgt cctgatggcc tcctgtcact aataacagaa tacaaaatgg ggtttacaag    7680
gcccaccatg aactttccca tccctctctg acttcatatc ctgccaggtc actgctttct    7740
agccaatccg ggctttctga tgttccccaa acacattgcc atcaagcacc cctccctggg    7800
gccttattat tattattatt attattatta ttattattat tattattttg agatggagcc    7860
tcaatctgtc acccaggctg gagtgcagtg atgtgatctc ggctcactgc aacctccgcc    7920
tccaagttca aatgattctc ctgtctcagc ctcccaaagt gctggaatta caggcgtgac    7980
ctaccacgcc tggggtccct ggggctttag cctttacagt tacctcagcc tggaaagctt    8040
tttcacagag ttctcttccc tactccaagt ccatctgctt acaccttacc tccaccctgt    8100
ttaaaatgct cttttttccac gattttattc tgattgtagc agtgtgatct gatacagtat    8160
atctatttgc ttatctgttg tctgcctctc tcacaggagt gtatttctag tgctcagatc    8220
atgcctagct catagcaggg actcaataag tattgaatga ataactttaa tgttttattt    8280
aatggaaaaa agatctaaag catataagct aaatcttaag ttttgataaa gctagatgtt    8340
gaatacagtt ttatttctat ttttttgatg ataattactg tgtcatattt catacatact    8400
ctgctggttg acaaaaacta gctccctaaa ataatgttac agacataagt aagaaatgga    8460
ttgtggtgac acataagctg ttaaagaaac ccgtagccta attttatagtg tatcaggttt    8520
gcaagtggtt taaaacaata gcggtttact gaatgttctt actagcgtga ggggagagct    8580
tgtgagaagt aggaagaggc cagagaaggt cctggggtct ggcacactct gatatgcttc    8640
atcacctctc cctaagctct ccctacaggg cagtggggcc agtggtgact tttgcggcac    8700
cctctccatt gtcttaccaa gggcttcagc tgtgagacgc cggttggtgc tacaaggaag    8760
gggaaacgtg tcagctcttt cctctgctct tttctcacat tgatttcaaa tgccaagaag    8820
ctgggctgag aaaccgggct tgtgatcctg gttgtactgc agtccaccat gtgctggaga    8880
gctctgcagg ttgtgctaaa gggtagtgtc tttattgcct cctgtataag cttgacttt     8940
acataggcaa gcaggttatt tccaggacaa ctaaattagt tggtgcgaaa cctcatttcc    9000
tagaaaccca ttttcttagt agaggaaacc catataacca tttgtctcca tgtaagtgta    9060
gctaataaca tgaataacaa aaatagctaa ttatttaaat agcaaaaata agtatggaag    9120
atgaatttgc agtaaaattc taatattaag ccactgatta tttaaaaaca atcagattaa    9180
gttgtagtac ctctgaaata attaaaggaa aatttgattc ttagaaaatc tcaattcatt    9240
ggaaagccat ggaattaata aaataaaaaa agaaaatctc aggcaatata aactaaggaa    9300
tggcaaatgg aaaatgtatt gattggtgga aaagtaattg cggttttgga cattgaaagt    9360
aattactttt gccattactt ttaatggcgg aaaccattta atggcaatta cttttgcacc    9420
aacctataaa taattggact ctagttccaa cttttgatatt tagctttccc atgactgttg    9480
acaaattgct taatctactt tccttgattt tgtcagtcaa atgaggagga agagacagct    9540
tgagaaacat ttgtaagaga aatgcttatt actttgtatg tgttttttcgt cttacatatt    9600
aaatataaat tcctttaggt gatattcttt aaaatgattt ccttacttcc ttttatattt    9660
```

```
acatccattt tctcttaaaa aaacaaacaa acaaaatact gcacaattct tgaagacaag   9720
gattacctct tacctcttat ttgtttcatg aaatatagag tacaattttt ttttttttg    9780
agatgggtct tgttctatca cccaggctgg agtgcagtgg cgccatcatg gctcactgca   9840
gcttcaacct tctgggctca ggagatcctc ctatctcagc ctccccagta gctgggacta   9900
cattcatgca ccaccacatc cggctaactt ttgaaaatgt tgtgtagaga tagggtttca   9960
ctatgttgtc caggctggtt ttaaactcct gggtccaagc aatcctcccg ccttggcctc   10020
ccaaagtgtt gggattacag gcgtgagctc ctgtgcccag cctagagtac agttcttgac   10080
atatagatag aaattaagta tttgtagaat gagtggaaaa aaaaatgaaa tgattatgtt   10140
gattttgagt ttctcggtgg aatagggctt tggattccta gaagagactt taatgttgaa   10200
aaattatttt tgtagttttg aaaatgttaa aaaattgaac atgagaaatc tccacttctc   10260
tgggcatgtg aaattaaagg gagggatgat caagttgtga gagattccct aggccagcag   10320
tgctgatgca agaaggtgaa catgtagact gctgtattct gtacacacac acacacacac   10380
acacacacac acagtcccct ccctcctggg aaagcaaaag ttgttgttgt ttttgagac    10440
agagtctcgc tctgttgccc aggctggagt gcagtggcac gcggttttgg ctcactgcaa   10500
cctttgcctc ctgggttcaa gcggctctcc tgcctcagcc tccccagtag ctgggattat   10560
gggcgtgcgc caccatgcct ggcaaatttt tgtattttca gtagagagag gtttcacca    10620
tgttggtcag gctggtctcg aagtcctgac ctcatgatca gcctgcctcg gcctcccaaa   10680
atgctggaac tacagacgtg agccactgcg ccaggcagca gaagtttttg acgatttcta   10740
gacaatgtgt gtaaagacct ttagagtcta agttaatgt ttgcattttg cagtcttagg    10800
cagatacaat gaggtataaa acacctctat ccaaacaact gagttggact gggctgaaga   10860
tttaagtcct tcagttcggt gtagtatccc aagagtggga tccgttgtat gtttgttaca   10920
ggccactccc tctagcttta tctgctaagc actgtgagat tgtgcttaat ttcactttgg   10980
ttttctagtt caggcctcca gcctggaggt gaatgtcctg tgtagaaaac tggccataaa   11040
tttagggctg ttatgaaatt tagtctgtca tgccaaccca tatagctgtc ataagttctg   11100
ctggtttttc tttctcttga tggagttctg cctatggcaa gccccagtta tcatcactca   11160
cgctaaagct ctacaagtac cacaagtaga gagaggaaat ggctggcact ttcagctcac   11220
ctagagaggc ctcttctccc tctggaattt taattctgct agtcctcttt gctatgcata   11280
gaagacagct cttcaatctt taaagccatt tatttatttg aataatctat ttagttttat   11340
ctagttgtta ctgtgaaagc actagcttgc ctctctctat taaagctaac ctggaagtct   11400
cattatttt tgaattttg ttgccacaaa catgacataa gaataagttt gttctgggcc      11460
aggcatggtg gcttatgcct gcaattccag cactttggaa ggccaaactg ggaggattcc   11520
ttgaggccag gagttcaaga ccagcctggg caacataggg aaacctcatc taaaaaaaaa   11580
aaaaaattaa ccaggtatgg tggcgggcac ttgtatagtc tcagctactc tggaggctga   11640
agtgagagga ttacatgagc ccaggagttt gaggttacag tgagctatgg ttacgccact   11700
ctactccagc ttgggcagca acagagtgag accctgtctc tttaaaataa ataaataggc   11760
caaatgttta aagtagaaag tcaaagtggc cagccattcc actacaagat aaccagtgtt   11820
ttcagtttga tttatagctt tccagattag catgtgtgtg catgactttg tcattttacc   11880
ttttttttt ttttttttt gagaaagagt cttgcttttt tgcccaggcc ggaatgtggt     11940
tgcaggatct tgactcaccg caacctccgc ctcccaggtt caagcaattc tcctgcctca   12000
gcctcccgag tagctgggat tacaggcatg caccaccacg cccggctaat tttgtatttt   12060
```

```
tagtagaaat ggggtttctc catgttggtc aggctggtct caaactcctg acctcaggtg    12120
atccgcccgc cttggcctcc caaagtgcta gtattacagg tgtgagccac cgcatctggc    12180
cgggaaatat ttttaaaaa ttcttgaag cccttaaagt ttacaggctc tgctaacatg     12240 ataaatacccc aataaaaata tagaaaagaa attctaagag attttaatat agaatcatta   12300
tctgttaact gttttagttg agagcaacag aaactgagtc tggttaaact aagcaaagag   12360
tgatttattg gaaggatgat aggtatacaa aaatgggatg ggggatgaaa ttgaacaagt   12420
ctcagaaagg caggaattgg cacagctctt gggacctcag tggcaggagt ttgtgaaccc   12480
tttcttcagg acattggaga cccactgccc ttcagactct ctccccattg acatttttaaa   12540 tccccataaa agagggttgt tggatttctt tcggcagagg tgtctgtgct gcatcaatca   12600
gttatggtcc aggaaatata gtcacaacaa agcatacacg tgaccaccag gggcgcatcc   12660
ctgcatatca gggagtattc ccagagaagg gaagttgaca caaaccggat tgcctctcca   12720
gtggtgtgca ccacaaaacc agactggagc acgtggtggg ggcagagtgg agggaatggt   12780
attacaggct cagaacgtgt cagcagtgga ggagaactca gatgaagatg cagaatttgt   12840
ggcagagctg cacttgtact ccagtcttca ggctcttgca tctcttacac cgtgatgctt   12900
atctagagat ggaaaagtgt tacagcggag gcttgggtgg ccagtgtgat aactcctggg   12960
cagacatcag tgcccagtgt gtacaggatg ccactgaact gaaatggaaa tgttccactc   13020
catatatgct tgaagatctc cttttgggg ttttcaatag caaaatggta atgtcaaaat    13080
ataaatgtgt ttcacagcta gttttggaaa cattttttcat tccattccac atgagatact   13140
tactgacaaa aactaaggaa tttatgctgc ctacacgaaa aactatggac ttctactttt   13200
cagaatttcc ctgctgaaaa aaggagacac ttctggacat acacattcag agcacagtat   13260
agcctatgtg atttgtgtaa agctccaaac tgttctctct agtatgtgtg atatgcagta   13320
gggagaggcc agtacatttc agtaaaattg caaggacagt ttcagcagaa ctgatttttaa   13380 ggagcaacag aaacatagca cttgaaaatg aatagggttc gtttaatgga caaagcatga   13440
taacagttct ttgattgctg aagaataatg ggtggttcac attagacatt aagttttttaa   13500 aaataaagtt ccaaaccatt caccagctgg gcaggttctg ttatcctgct gtagcatgca   13560
gctggaatgt gcttatttgc ttaaggaaat tatgcttttg tgattttgta ttcatatcag   13620
aaatgtgtgc ttctgtttcc taataattac ttcactgtta ttggattata acatagttac   13680
tccctgtcct ttcatgggat tcttgaaacc tttattcagg atcatttctt ctgagtcagt   13740
ttacagtgca ataaaaactg tttattttta attatttta aaaaattttc ctgaaactta    13800
agagacagaa ggcaacatat aatccagggt tttcttttgc tatagaggat atcattagga   13860
cgtttgacaa aatctgaata aacttgtaga ctaggctggg cacagtggct catgcctgta   13920
atcccagcag tttgagagac caaggcagga ggatagcttg agcccaggag tttgagacca   13980
gcctgggcaa tgtagtgaaa tcccatctct acaataaatc agtaaatatt tattgtatta   14040
atcttatgtt atcttatgtt aatctcttat tgtgctgtgg tcccagcttc ctgggaggct   14100
gaggccggag gatcacttaa gcctgaaagg tagaggctgc agtaagccat gatcacacca   14160
ctgcactcca tcctgggtgg cagagtgaga tgctgtcaat agaaaaaaaa aaaaaaaga   14220 aacaaacctt ttcaacctcc ttaaaattct ctcgtgcccc acaggaagct cttggactaa   14280
agcacagaaa gtcattacta attctatctg gaagccagaa aataaggtgg agccaaagat   14340
gactccaaac ttgggagact gggtagactg gatggtgatg ctgttgacca aaataggtaa   14400
```

```
tagaagagga gtatcaggtt ttaactgaga gggagggtta ggatggtgag aagaagttca    14460
gctttagact tgttgagttt gaggtgccca tgaagtctaa gtggagctat gtagaaggca    14520
ggtggaaatg cgaatgtgga gttctggaaa ggaatttggg attgcagtgt agacttgagc    14580
ttacttgtag catctgaggt ctagctgaga actcctaagt agatgagaat tcactagaga    14640
ggctatagat aggcaagttt aaagagaagg gtagagacac ggagaagggg gttggggagc    14700
agccaaagca ggcgtccccg cagttgactt gccaccaagg gaatgtgggt gaatgaccaa    14760
ggcaggcgtc cccatggaga tcagacacca aaggaacgtg ggtgaataat cagagaggca    14820
tccctgcaat gattaaacac caagggaagg ctgccttccc gagtccgtga ccggcaccgg    14880
agttttgggt ccacggataa aatgtgtctc ctttgtctct atcagaaaat gaaaggaatt    14940
gaaattaaga gaagggagag attgaagggt ggcgccaaga ttgaaaggag aaagaggttg    15000
agggatagtg agagaggttg gagaaaagag taaaagagg ccgcttaccc gatttaaaat     15060
cggtgagatg ttccttgggc tggttggtct gaggacctga ggttgtaggt agatctcttc    15120
acgaagtgag gatgaggaca ggggactggt ctcccgaagg agtcccgctg accctggtct    15180
ttggcaccaa atgtttcacg tgtgcatgtg aagagacccc cccaaacagg ctttgtgtga    15240
gcaacaaggc tgtttatttc acctgggtgc tagtgggctg agtccaaaaa aggagtcagc    15300
aaagggcggg aattatcatt agttcttata ggttttggga taggcggtgg agttaggagc    15360
aatgttttgc aggcagcggg tggatctcac aaagtacatt gtcaagggtg gggagaatta    15420
taaagaacct tcttaagggt gggggagatt acaaagtaca ttgatcggtt agggtggggc    15480
agaaacaaat cacaatgatg gaatgtcatc agttaaggct atttttcattt cttttgtgga   15540 tcttcagttg cttcaggcca gctagatgta tacgtgcagg tcactgggga tatgatggct    15600
tagcttgggc tcagaggcct gacaatatat actcgtaaaa aacaagaaaa gaaaaatcaa    15660
agcagtttag aaggttataa acaaaaaata tgccatcttg tcccacccta ctccttacca    15720
cattttcttg tgtctccttc gagacaattt tagtcttatg gaaacatatg tattacacat    15780
atggcttatc ttttattata ctttcccatt attgctttgg ttaggagtgc cttttcagct    15840
gcttaataaa catggttgac agcccacagg catgtggaca aaatggccca ttagattgat    15900
tttttttcct tctcttgttc tgtaatgtgt tttatgatgg tgtgcttata gtcttgtcgg    15960
aaaaaaattt cttcctttgc attttattt tctttacat tttcttaaac agtaatatta     16020
ctgttcaagc aaacatttct tgatattcct aaatctttcc ttgattaata atgctaatat    16080
agtgtcacat tcttgtttgc ttaatgtgaa cagactgtga acagactgat acgaaatgtt    16140
attaagtgtt aactatttat taagacttca taaatactac cctgggtgct agacgtgcaa    16200
taatgagcaa aacagacctg gtgttttttcc tcatggatta ttacctatgt ataagagagt   16260
aataccatta ttgtttgaat catgtgaaag ataagattta gcatcagttc ttaaaggtga    16320
agtgattttg ttctctcaga gtttaaagac ttttcacctt ggagaggctc gcgtgtcagt    16380
tggcgtgccc atctgcctcc ctgtatcatc agtcactctg ttttgacaga agccacattc    16440
caaagtcact tcttttcaca ggttctgaag gtggaaaaaa agaaacccca gccacttcct    16500
agttgaacct aaattcttta aaatacattt aattttgaat aaggctttgg taaaatcaca    16560
cagttcttca taatggttta gcatcctcct tcctagagag tccagcctac agtatgaatt    16620
gacctgatcc tgcctgtgtg ggtgtgcctg aaatcaaggc ggatatcttt aaaagagacc    16680
cacccatagc attcctgacc tgtaaactcg ctgcatgttg gattgagact gcggtggggg    16740
ggctctgtaa tttccaggct ttttaatgat gtgtacagtt gagagtaaat agtttaaata    16800
```

```
atttcatagt tagggagagt tcagcactgg tattaaacag agttcttaag gcaaaatatt    16860
ttcagataca gttcttaaag agatgatcag aatgttaatt tttcttgtct tttaaattgc    16920
ttttcatttt gctttgccca gcttaataac ttttttatat tgttatgttg ttaatttta    16980 aacaattttc tgccttaaga tattggctca attttaggta ttctgttcta aacacattac    17040
agtcttactc ccatttaaaa gtttaagtat taaatattga caccaaactt tttctgctgt    17100
gtggaagaga ttgatgaaga cccaaatgag tttgtgaata gttttcagaa gttatttaga    17160
tcatcaagtt gaatcagtac caacagattc catccatctt ccatgcctat ctgaatgcct    17220
gtcctttgtc acatacaact gtgtcttt cc gaactattcc agtctgtaac actgaagcag    17280 cttt ccaaaa ctaacattac ggggatagga tattctaaaa tatctttacc ccttggatat    17340
gtataacaat tgattgtata gttatgtaaa ttttattaat ttgttttat ttgtttatat    17400 cgtatctctg atcagattgc ctgagagggc aagaaaggat cttttagttc tttgggacct    17460
tttgtaatgc ttaattgacg atatgcccct ggtaaatttt gttaaccat cctcactgca    17520 gttgttccaa agttaagatt aaagttaaca cacaaacttg tctagcagat atcttctata    17580
aagcaagatt tccattaaaa ttgaccaaga agcaaaagt tttcatctat gagatcaaaa    17640
gtaaagtagc ttggttttg tgtattaaaa tccaagtatc ccaaaggtta aaacaaggga    17700
taatcttacg atgtttggga atgaatactt aagatgaagg gggacagaaa aattcatgtc    17760
agttactaac aattttccc cttgttttgg gtttcacttt cttttttactt ttatataatg    17820 ctgggccaca ctttttttt tttttctgt atcacctagg ctgtagggaa gtggcatgat    17880
catggctcac tgccatctcg accttctggg ctcaggtgat cctcccacct atctcctgag    17940
gacctgggac tacaggcatg tgccaccatg tccagctagt gttttgttt tttgttttg    18000 tagaggcaag atttgccat gtgcccaggc tggtctcaaa ctcctgggct caagttatct    18060
gcccaccttg gcctcccaaa gtgctaggat tacaggcatg cgccactgca cccagcctgg    18120
accacactta tataaacatc ttagtttttt gcatgattta cttgtgttat cactaccaac    18180
aaaggttaat ttgaactacg tgtttctgca ggggcctact gctgataatt atttggaata    18240
ctatggctgg gtggctttaa gaatgtgtgg tagtaaaaca tttacaaata ttttacattc    18300
taataaagct gaatttactt ttgaactttt gatctcttca tctgtaggcc aatatagtac    18360 tttttttggga caggctttct ctttgttgat ttatattttt tgctttttt attagaacaa    18420 aagaaattat gctagcattt tagaatctat ttaagaaaat caaataatga taaaaatcag    18480
tgttaggtgg tgttcttatg cagtccttct tgctccccctt cttttactgt tcatctgaag    18540
ggcatataat ttataagtta tttctattga aaacaagtag ccctgcttat ctcttagtgt    18600
tagatttgac tgttgcttac aaaattcttt tttttttt ttttgagatg gggtttcgct    18660
cttatttccc aggctggagt gcaatggctt gatctcggct ccccacaact tccatctcca    18720
aggttcaagc aattctcctg cctcagcctc ctgaatagct gagattatag gcatgcgcca    18780
ccacacccac ctagttttgt attttagta gagatgggtt ttctccatgt gatcaggctg    18840
ggcttgaact cccaacctca ggtgattcgt ccgcctcggc ctcccaaagt gctgggatta    18900
taggcgtgag ccaccgtgcc tggcctaaaa ttcttttttt ttttttctt gtttccagtg    18960 aggttggaac ttagaaaatt cctttttttt tttgacacgg agtcttgctc tgtcacccag    19020
gcaggagtgc agtggcgtga tcttggctta ctgcagcctc cacttcccag attcaagcaa    19080
ctctcctccc tcagcctccc aagtagctgg gattagaggt gtgcaccacc aatcctggct    19140
```

```
aatatttgca ttttttagtag agacaggttt caccatgttg accaggctgg tcttgaactc   19200
ctgacctcaa gtgatctgcc cgcctcagcc tcccaaagtg ctgggattac aggtgtgagc   19260
cagtgcgccc ggcggaactt agaaaattct taaggtataa ttcagcaaat ctctaaggac   19320
ctagatttta ggtaggaatg tttttcttgc catgatggaa ataaacattt ttaacctctc   19380
ttttagatcc atcatgttac acaaaatgga ggactatata aaagaccgtt taatgaagct   19440
tttgaagaaa caccaatgct ggttgctgtg ctcacgtatg tggggtatgg cgtactcacc   19500
ctctttggat atcttcgaga tttcttgagg tattggagaa ttgaaaagtg tcaccatgca   19560
acagaaagag aagaacaaaa ggtaactgtt agagagtttt tgattctgta aatagaagcc   19620
ttttatggaa atcttagtat ttttgcacaa aagcttttc tcagaaattt gggtacacat   19680
taaaattaaa ctattccaga tgcagttaaa tgaaaacatt ctacaaagaa agctgaaaaa   19740
taacaaggtt aaagatatca aagcattcat catgggttta atcaagaaga acctaaggag   19800
gtgggcggca ctatccctgt tttatggatt agaaatcaaa aagtcacaag ttaaacaacg   19860
tttcccaaga tgccaggtgt cagagctgct gtgtggacag aggactgtga agtgaaaaag   19920
ccttgctctt tctgttcata ccagcatgct gaatcccagg ttgtgtttac cattttctga   19980
aaaggttgta ttctttggaa ttaataatgt gttttctcat agatacatta tacatagttg   20040
ggtgattcac acatcagctc ctctccccag acaaacaagc tgtaatacag aatgtggcca   20100
accgattcta tttacggtaa acaacactct tgttttagga atggcaaaca tatgagcatg   20160
gttgtctggg gaagagggct tcttcattca cttcactttt ctctgcatgt tcctttgtac   20220
ctctgaaggg ttttttgttt gttgtttgt ttgtttattt tttgagacag agtctcgctt   20280
tgtcaaccca ggctggagtg cagtggtgcg atctcggctc actgcaagct ctgcctcctg   20340
ggttcacacc attcttctgc ctcagcctcc caagtagctg ggactacagg cacctgccac   20400
cacgcccggc taattttttt tttttttttg agacaagtct tgctctgtcg cccaggctgg   20460
agtgcagtgg ctcggtctcg gctcactgca agctccgcct cccgggttca ccattctc    20520 tggcctcagc ctccccagta tctgggacta caggtgcctg ccaccgtgcc cggctaattt   20580
tttttgtgtt tttagtagag acggggtttt actgtgttag ccaggatggt ctcaatctcc   20640
tgaccttgtg atccacccac ctcggcctcc caaagtgctg ggattacagg tgtgaaccac   20700
tgtgcctggc cagtttttt gtttttttta cttgttattg acttgaagct cacttctgga   20760
gttgtataca ttacatatgt gttacctagt ctccataaat aaataaaatg agggttaaag   20820
atgcctaatt ttactaaaaa taaaacaaac ctgtgtgttc ttggcatgtc ccacatggca   20880
aaaggttgtc ttttagccca ggcaaatgta ccagattaga gaaggactta agacattaga   20940
gtttttttgt ggttcctgtg cgtccgagga aaagaggcag gtgtggggtg agcaaagtca   21000
acgctgagac gagccagtga acattgattg tagaagaaac aattattcag gtaatggata   21060
gtggtcatgt gcaaatggga agagtatatc acgaaaacat tgtcagttac taggaagaca   21120
aaaccagtca gtagatacat ggattcaaaa gtggctcctg ggagaactca agattaggca   21180
tcctttctct ctcatctcaa ccatcttgta ctccatccga gccccagcac aagttggcca   21240
tcctactcat tgcccctgcaa gttaatttca caaagaaggt aaataagttt ttgaatgca   21300 aagccctgca ttcagaagtt ggtccagtaa ccctaagtaa ttttatctt ttaaaaccca   21360 aacacatttt taacattttt tattttatta tcattatttt ttagacaaga gtctcgctca   21420
gtcacccagg ctggagtaca gtggtgtgat ctcggctcac tgcaacctcc gcctcccggg   21480
tccaagcaat tctcatgcct cagcttccca agtagcaggg agtacaggca tgtgctacca   21540
```

```
ctcccgagat aattttgtat ttttagtaga aacgaggttt caccatgttg gccaggctgt    21600
tctcaaactc cttgacctca aacgatccac ctgcctcggc ctcccaaagt gctgggatta    21660
cagatgcgag ccactgtgcc tggcccacat ttttaatacg ttttgatccc ccttctcccc    21720
ctgagcatgt ccactcagag tgcatctaca gtacgttgat tttgtatagc cctcagtgac    21780
agcttaccat acccttccta ggttgtacag tattgtagtt acttgttcac aggcctgtat    21840
cctcctacta gactgagttg atggcagtta tgaccgatgg tagctgaagt tttatttaaa    21900
tattcaaact aaaaactctt tatctgcagg gacctctcct agtgtagatg catagtcgaa    21960
acttgataat tgacgtgtat tgctggtggt gagggaagtg ctgattgtgg tgcagacagc    22020
acattcctgg atgaggggat agtataggca aaggcatgaa gaatgtttgg gagaatctgg    22080
aatgtagaca aagagaaat tgtgttttga aaatcaaagt aagaagtttg gtaggcaatg    22140
aggagtattg ttttgtttt tgttttaaa tagagacagc gtctcgccat gttgcccagg    22200
ctggtctcaa actcctgtgc tcaagcgatc ctcctgcctt ggcctcccaa agtgttggga    22260
ttataggagt gagccaccat gaccccaagg gcagttttg atcaggggat ttttcataca    22320
gcttgtgcag ctggtgctca aagtgtgatg aatgaatgaa accaacaaga tgtatctgaa    22380
ttactttgtg agtacattat cttttggaact tgtttcatgt ttacagaaag taaattggtg    22440
gtttaagtgt tgggagctgc ctgtgtatcc tttgtgtgaa agaattagaa cacacagatt    22500
ttattcttaa gtagtttcta atttttgttga ggaaacaaac atttgaaagt tatgggcctt    22560
tgcaaaacca ttatacaagt aaataatact tagattatat gaagatatag aacaaaaaaa    22620
gtatctgagt agcatagggt taatcaggaa acaattcttg gaggaagtaa tacaaggaaa    22680
tgggaggctg aggagagcat ttgcctctgc agtttatgga gaggatttta ttaaattatt    22740
caaattcatt tcaatagaat attcccagta gataacatta gcatttaaaa cagccaactt    22800
ctgccatttt cttacaaaaa ttcagctttt agagggaaag gaaagtcat tcctttcctg    22860 tgatagatca tgtttgtttt ctaatgttgg attagagatg gggaaagagg gaggcaaatt    22920
aagtgttaaa ctggaaggag gtgagggaaa gtggttgctt gggatcataa aatgcaaaca    22980
taatgttgct acttcctcat ttcactgaga gagtggtatt cataaccaca tcctggtttt    23040
cttcctcatt tcattataaa agagagccca gtttaactgt gttaattctt tgatgtaagg    23100
aaataccgta tgttgctttg aatacaacta aatcacatga tcataccaat aaagatgagt    23160
taccatgagt ttgttctatt ttatatacat tgcataaaat tcttggaatt ctttaccct    23220 taatcctctg ttattcgtgg tgttttggat gagaatgttg ttttttctcaa tctatggatt    23280 atttctttgt gatgtgaggt gaagctagta gttcagaaac acgtacgtga cagatacagc    23340
aaaagcttga attaataaag atgttctagg ctgaggcagg aggatcactc aaggccagga    23400
gtttgagacc agctgacaca acataatgaa acctcatctc tacaaaatga aaaatttaa    23460 ttcagaaaaa aatattctaa tatttagata ggaaatagct aggaacgtaa ggagtaaatt    23520
atggtaggta gttaccacac actgacaaaa ttttaaacta acattttgcc tccacagctt    23580
gttcatgatc agatatttaa aaacgggagg accaaatacc acattctcac ttatttttta    23640 attttttaa tttttttttt ttttgagatg gagtctcact ctgtcgccca ggctggagta    23700
cagtggcgtg atctcggctc actgcaatct ccgcctccac ggttcaagtg attctcttgc    23760
ctcagcctcc caagtagctg gaattacagt catgcaccac cacgcccagc taatttttg    23820 tatttttagt agatacaagg tttcaccatg ttggccagcc tggtctcaaa ctcctgacct    23880
```

```
cagcctgcct tggcctccca aagtgctggg attacaggag tgagccaccg tgcctagcct    23940
gttctcactt ataagtggga gctaaatgat gagaacatat ggatacaaag aggaaaatga    24000
cacttgtggt gggtaggaag agggagagga ttagaaaaaa taacccattg ggtgctaggc    24060
ttagtacctg ggtgacaaaa taatctgtac aacaagccat tgtgatgcga gtttacctgc    24120
acaacctgca cacgtacccc tgaacctaaa ataaagtta caaaaataa gtagattaaa      24180 aatgggaggg ataggatacg gcgaagggac attatatgtt tatatcccaa taggcttatt    24240
ttcaagatac aaaagaaaga aagaaattca aatacattac taggaattcc cagagggatt    24300
ttattcttgg cctccttcaa aaagtagcgt acagccgggt gcgatggctc acacctataa    24360
tcccagcact ttgggaggcc gaggtgggtg gatcacctga ggtcaggagt tcaagaccag    24420
cctggccaac gtgatgaaac cccatctcta ctaaaaatac aaaaattagc caggcgtggt    24480
ggtgggcacc tgtaatccca gctacttggg aggctgaggc aggagaatgg cttgaacctg    24540
ggaggcggaa gttgcagtaa gctgagatct tgtcacagca ctccagcctg ggcaatagag    24600
actgtctcaa aataaaaaaa aaaagtagc gtactaagaa tattctggta cctgtcattt     24660
tggtgcatta agctaggga ttgattgttt ggtttgtctt ctttaattct gtgtatgatt     24720
ctacatttaa aaagaacaca actggctggg cacggcggct cacgtctata atcctagcac    24780
tttgggaggc caaggcgggc ggatcacctg aagtcaggag ttgagaccag cctgaccaac    24840
atggtgaaac ccggtctcta ctaaaaatac aagaattatc tggggcgtgg tggcacatgc    24900
ctgtaatccc tgctacttgg gaggctgagg cacgagaatc acttgaacca gagaggtgga    24960
ggttgcagtg agccaagatc acaccattgc actccagcct gggcaacaag agagaaactc    25020
cgtctaaaaa taaatacata catacataca tacatacata catacataca tacagaagag    25080
cactacttag ctcccccaga atcatctgaa cctgggaggt ggaagttgca gtgagctaag    25140
attgcaccac tgcactccac cctggacaat ggagcgagat tgtctaaaaa aaataagaag    25200
aataaaaaat aaagagcact gtatttcatt gttttgtgtt agttgctggg cacaggacag    25260
cagtagtctt tttaaataat tgacatatca taaaggttac ctatttaaag tgtacgatac    25320
aatggttttt agtatatcta cagagttgtg cagccagcac cacaattaa ttttgtaatg     25380 tttttctctt ctgaaaaaga aaccatgaac cattagcagt cactccttcc tcatccaccc    25440
tccccaccct cggcagccac taatctactt tctgtctctg tagatttact attcgggact    25500
tttcatataa atggatgttt catgtaaatg ggatcataca gtgtatgttc ttctgtgtct    25560
ggctcctttc acttggcgta atgtatttga agttcatgtt gtagcatgta tcggtacttc    25620
attgcttcct attgctgaat aatatttcat catatggagc agtcatctct acttactata    25680
gggatttctc actggtaaaa aactatactc aaaataaacc tttcaaagaa gctttgtgta    25740
gtaggtttac cactgtatct gtttggacta gtggcagtag gtttacctct gtatccgttt    25800
ggactagtgc cagtgttagg tttgcaagag tttccctgtt acctgttttc cctgttttc     25860 atgccaggaa agcttttcct tcaaatagtc ccatggctag ttccctcact tccatttat     25920 cctctgttct acccagggca ccccagctaa tttgcagcat gtctcccct ttccttttg      25980 cttttgtttc tgttggtatt tgtcactgtc taacatactt tatttatttt tatttttatt    26040 tattttatt ttcttgagac agtgtcttgc tctgttgccc aggctggagt gcaatggcgc     26100
gatctcggct tactgcaact tctgtctccc aggttcaagc aattctcctg cctcagcctc    26160
cagagtggct gggactacag gcatgtgcaa ccacacctaa ttttgtgtt tttagtagag     26220 acagggcttt gccatgttgg ccaggctggt cttgaactcc tgggctcatg tttatctatc    26280
```

```
tgcccacctc ggcctcccaa agtgctggga ttacaggcgt gagccactga gcctggacta    26340
gcaaactttg tattttatat gtttatctct tccaccagaa tacaaattcc aagagggcaa    26400
ggattattac cttttgttt actactctgt actatagagt gcttggcaca tattagacgc    26460
tcggtaaatg tttaagatac aaggccagag gccaggcgtg ttagctcaca cctgtaattt    26520
caagcacttt gggaggctga ggtgggaaga tagcttgagc gcaggagttt gagaccaacc    26580
tgagcaatgt aacaagaccc tgtctcaaca agaaaattaa aaaattagct gggtgtggtg    26640
gcctacaccc atagtcttag ctacttggga gactgaggtg ggaggatcac ttgtacctag    26700
gagttcaagg ctgctgtgag ctgtgattga gccactgcac tctagcctgg gtgacagagt    26760
gaaaccttgt cttttttttt tttttttttg agacagggtc ttgctctatc atccaggctg    26820
gagtgcaatc gcatgatctc agctcactgc agtctctgcc ttctgggttc aagtgattct    26880
catgcctcag cctcctgagt agctgggact gcaggcgtgc accaccacgc ccagctaatt    26940
ttttgtattt gtgtgtgtgt gtgtgtgtgt gtgtgtggag acggactctc gctctgtcgc    27000
ccaggatgga gtgcaatggc gcaatcttgg cttactgcaa cctctgcctc ccgggcttaa    27060
gcgattcttc tgcctcagtc tcccaagtag ctgggattac aggcatctgc cataacacct    27120
ggctaatttt tgtatttttta gtagagacag ggtttcacca tgttggccag gctggtcttg    27180
aactcctaac cttaggtaat ctgcccacct cgacctccca agtactggg attacaggca    27240 tgagccaccg tgcctggcca ttatctctaa aaaaaaaaa aaagtttaa gatatgaatg    27300 gtattgtgag tggtggtaac agtaacaatg taaagtatt tgaagtattt gtagtcgagg    27360
taggtgtgta cgtacacaca tgcacacaca aacatacaaa tgactgtttt agatgtagga    27420
aaaaccagtg ttttttttatc ttgaaatctc attctgcgct ttcatggaca gcatagaaac    27480
agcaaggaag tggcttcctg ttttaacat taaaaacagg aaaggacaga cggtggtatg    27540
acctatatga acagtaagga aagtcgttaa ttaaccatgg ttgaaaggtt taaaagttgt    27600
agtctgaaaa cctttcattg agtatttcac ctactttct tcattaagta gagataaaaa    27660
cagaattatt ggtttataaa atacttttag aatttataat gctttccttt tcccttttc    27720 ttttctttct ttgtgtgttt tttttttttt tttttttttt tttttttttt gagacaaggt    27780
cttactctgt cacccaggct gaagtgcagt ggcacaatct cagctcactg cagcctcgac    27840
ctccctgtgc tcaggtgatc ctcccacctc agcctccgga gttgctggaa ctacaggcac    27900
gtaccaccat gccctgctaa ttttgtgtt ttgttgtaga gactgggttt gcccccagg    27960 ctgatcttga acttctgggc ttaagtgatc cgcctgcctc agcctcctaa agtgctggga    28020
ttataggcat gagccactgt gcctgggcca gatttttttt ttttcttttc agagacagga    28080
tcttgctctg ttgcccaggg ttgagtgcag tggcacaatc tcagctcgct gcaacctttg    28140
cctcccacgc tccagtgatt ctcccacctc agcttcttga gtagctggga ctagaggcgc    28200
acgctaccac aactggctaa ttttgttt ttttttttg tagagacagg gtttcgcctt    28260
gttgcccagg ttgatcttga actcctgagc tcaagcgatc cacctgcctt ggcctcccaa    28320
aatcctggga ttataggcat ccaccactgc gtccaactat aatgaatttt aactgtgtga    28380
tgactccatt ttcaacactt cctcaggtgg aattatttg ggatttaaaa attcttaatt    28440
taagttttga aacaactttg tcatgtttca gttacttcta aatctatctc ataaggctat    28500
ttccttcttt agtagaaaat acattttcca gctgggtgtg gtggctcata ccaataatcc    28560
cagcagtttg ggagactgag gcaggaggat tgtttgaggt taggagttta gactggcgtg    28620
```

```
ggcaacagag agagatcttg tctctacaaa aaatttaaaa attagccaag catggtggtg    28680
tgcacctgta tgtagtcctg gctacttgag aggctgaggt ggggagatag cttgagtcca    28740
agaatttgag gctgcagtga gctatgatca tgccacttct ctccagcctg ggttacagag    28800
tgagacactg tttctaacaa taacaacaac aacaacaaca aatgttgccc aaataaaaat    28860
tcaaaacgtt atagattttt tttttactat cttgtctttg atatgcaata ttatgtttat    28920
aatgaaatgt cttgaaatct tttagtagta ctatcatacc agcaaacagc attagttatt    28980
attattatta ttattattat tattattttg agacagagtt ttgctcttgt cgcccaggct    29040
ggagtgcagt ggtgcgatct cggttcactg caacctccac ctcccaggtt caagagatca    29100
gccttccgag tagctgggat tacaggtgcc tgccaccaca cccggttaat ttttttgtatt    29160
tatagtagag acgggtttcg ccatgttggc caggctggtc tcgaactcct gacctcaggt    29220
gatccacctg cctcagcctc ccaaagtgct gggattacag gcatgagcca ctgtgtctgg    29280
ccttccttca ttttaataat aatggatatt gaggcttttt tcatttcttg tcagtgatga    29340
ataaaactac tataaatgtt ctgatatatg catttcctgc atgtaaatat gagtttctcc    29400
agggttggaa ttattgagtt atagagttat agagtatgca tgtcttcagt ttcactagat    29460
agtgccaaat tgttttccaa agttattgta ctggtttgta cacctaccgg ctgtgtttga    29520
gaattctttt tttttttgaga ctgagtctcg ttctgtcacc caggctggag gagtgcagtg    29580
gcgtgatctc agctcactgc aagctccgcc tcctgggttc acgccattct ctgcctcag    29640
cctcccgagt agctgggact acaggcgccc gctaccacgc ccagctaatt ttgttttgt    29700
atttttagta cagacgggtt tcactgtgtt agccaggatg gtcttgatct cctgacctcg    29760
tgatctgcct gcctcggcct cccaaagtgc tgggattaca ggtgtgagcc actgcgcccg    29820
gccaagaatt gttccacatc tctttactaa cactcagtat tgccagaatt taaaatttt    29880
gccagttcaa ttggtatata tgtactagtg tctcattgtg gttttaattt gcaattctct    29940
attgcccagt gaagctgaac agcttttat atgtttaatg accattggaa gtgctgattt    30000
catgaagtct ctgttcaaat cttttgtccg ttttttctact gggtttgtgt attttctaa    30060
gtggttttta ggaaatattt atgtatccta caagtatttt cgtctacca tccctctttt    30120
gtggcttgtc tttcgcttag catagtgttt tcaagattca tgtaccattg tagcaagtaa    30180
cagtacttca ttcctatatc actgtatact attctgttat gtggatatac cacattttgt    30240
taccaccttt tggctgttgt gaatagtgct tctatgaaca ttcacataca agtacttgtt    30300
cgagtatctg tttccaattg gtacgtacct aagaatggaa ttgctgggtc acatggaaag    30360
tctatattta cctttaaaaa aattattttt tggctgggtg tgatggctca cacctgtaat    30420
cccaacactt tgggaggcca aggtgggtgg atcgcttgag gtcaggagtt tgacaccagc    30480
ctggtcaaca tggtgaaacc ccgtctctac tgaaaataca aaaattagcg ggatatggtg    30540
gtgcacacct gtaatcccaa ctacttgaga ggctgaggta cgagaattgc ttgaacccag    30600
gaggcgaatg ttgcagtgag tctagattgc gtcactgcac tccagcctgg gtaacagagc    30660
aagactccat ctcaaaaaaa aaaaaaaga aaaagaaaa aatttatcac gttcatcgtt    30720
gtcaaagtct acatgtacct tgagaaaacc aacacactt tccacctttgg ctgtgccatt    30780
ttgcatgtcc accaggaatg tattaaggtt tttctgagtc ttatagtttt atattttacg    30840
tttagggcta tgctccttt gagttaattg tataaggtat gaggtttagg tcgggtcatt    30900
ttttttggcca gtggatgtcc tagtgagaaa gtttttaaaa taagtatggc atttaaaagt    30960
aatctgtgaa ggtctaaata ctttatagtt ttgtagattt aaattttct cccacgtttt    31020
```

```
cctttactta gcaagttttg aataaaagta aagctgaaat aaatttgttc cttaaagact   31080
gctagagttg gtttacttgt cccagttttt tttccctgca ctggatgcat aggtcaaggg   31140
tcgaacttta aatcatcctg accttgagaa gacactgaga cagttctaag catgttttcc   31200
aagcttttta tcctaacatc aaagcagtga ttgtttgcct caaatgctca tgtttgagag   31260 aaatttgtc ttttgttata tcgagattgg tgccccagac tctaaaataa gtaaagtta    31320 ttaaattaga actgacattg agaattctta atggaattag tagtaacact accactaata   31380
gtgttagttt ggaataatac tagtctcagt tttggctttg tcactgcatt gttatgtgac   31440
ttggacaaag aatttaaatt ttattcagtg actctgtaaa atacatctaa taagttatta   31500
aacatctatt tctcaacaat aattataatg accacgttgt tgaaatcgtc acattattgg   31560
tagagttacc aaaaacactg taggtcattc aagccaacag agaattaggc atttatggct   31620
ttgtggaggg gcgagagcag tgaggttagg gcctccctcc cctaactggg cagctacccc   31680
aaactaggaa actgctcctg ccgtgagtac tctgagtgct ggcatcacaa ctgtcgcact   31740
gccagaggct ggtgaatagg cagtggcaca tagaatcgcg ctggtgccga cccagcactg   31800
aggtctgcag gggcttgcct cctacgctgg tgcaaagcgt ggccctgcc atccagctgt     31860 tgtatgtgct tctcactggc agaccctaca tcacatccgc aacccgatca caagggtgtc   31920
caggaaatac agttttagc cttccatctc ctaagtgtgt gtgtgtgtgt ctgtgtgtct    31980
tgtagggggt ttgttatgtg tgtgttggtc atatgcagaa cataggaaaa gaatgggaag   32040
gacaatagca cagtggtctt gaagtgcttt gaacgctatc aaagtatttc agattgattt   32100
agtagcatca ccaaataaga ggcagtgtgg cattggggtt gggagcacag agtaaagtta   32160
gaaggcctgg atcatcagtt cctggctctg cctctggctg ctttcctaag tgggaaagcc   32220
atttagcctt tctgaaagtg taagaaatat cttccttaag agtgtgcaga gtatgtatat   32280
ttacatactt acatatataa gtatataaat atgtgtgcat gtaaagcact tggcaagtgc   32340
ctggtatgtc ataaatactc agtagatggg cactcttgct gctgttgtga ttattcatca   32400
tctttatcat catcatgtaa acatatttga ctatctgtgt tggaccagaa tgatgcttaa   32460
caaagggaca gttgttagaa agtggacttc aaaaagtgat agcatccagc tttgcccect   32520 gtgttcttaa tgcctgtata ggtgctacaa taggtggtac ttatgtatat tatattaaac   32580
aatatgggat attttctaga aggcttacct taaataggct taaccagtaa aggatattta   32640
ttggcttctt attgagatgt ccctagacta cttttgataa ggtcttcatt gatctctaag   32700
cagcaaatcc aagagtttga gttgttctct tgagttgaga aggctcttaa gtgaggagta   32760
tttcaagccc agtgatccag catttagtcg cgagtaggta ttgttttccc tctccttaca   32820
tgtgctagga tatgggattt gtgaggatct tcaggaagaa tgtttatgag tatatccttaa  32880 aggctgcttg gacttgactt taccattgtc actcccttat cagttaggta ttcgctcctt   32940
ctctggacaa acactctttt atagtactta ttatattgta tttatttgtg tgtttctcca   33000
ctacactaag agttcttagg gagtgtagag gttgttctta ctcattttta ttcccagtgc   33060
ccagtttagt gcctggaagg tactgctcag taaatgttca ataactgagt attaggtcaa   33120
tgatgatgag tattacataa gccttaacta aagtcacttc acagtgacca aactgaggag   33180
gaggaagaga gtggtggaga tgggggaatg agggtcggaa tagtggggct atcactcttt   33240
gcggagagaa ctgtcttgtt ctttaacgta tcctgaaagt ctggcataca acccagtatg   33300
tatcgagtac tcactaagat atatttgaat gaatgaatga aaagattacc cccctagttt   33360
```

```
aactgtggtc ttagagtgtt taaagttaac ctgatatttt tggaaataca ctcccattgc   33420
ctagaactgg aactgcaagt agtgacccct cccctccttt ttttcatggc taagctgcag   33480
ggagtttggt ttgctgccct tctcatcttt tttaaaatta ttatttttat ttatttattt   33540
atttatttat ttatttattt atttattgag acagcttttc actctattgc ccaggctaaa   33600
gtgcagtggt ccgatcttgg ctcactacag ccccaacctt ctgagctcaa gtgatctgtc   33660
cacctcagcc tcccacgttg ctgggactgc aggcacatgc caccacacct ggctaatttt   33720
tgtatttttt gtagtgacag agtttcacta cattgcccag gctggtctca aactcctggg   33780
ctcaagcgat ccacccgcct tgagcccaaa gtgctgggat tacggcgtga gccactgcgc   33840
ccagccatgc ctatcaaatc tttctgctga acctactgac tgagatcaga gctactaccc   33900
tggagcttag ctaaggagta aaggggagct gagatttcgg ccgtaagtcc ctctctccta   33960
ccattctatg ccacccgctt tggtcccta acatccctgg ttgtgacagc ttctcctcct   34020
ttaccctgtg ctactgtgac ttaatcactt gttaaggaga gatggaaatg cctgaccatg   34080
gcaggcacaa ttctttgttc aggaaattgg aacccattgc ttccttccta atcccagaca   34140
gctgtgcctc tggttttctt tgtttagccc aaggctgagg ggtgaagctc tacttcattc   34200
tggcctgcag tctttttttct atcttggggt ttgataatcc ctctggtatt tggagcagac   34260
tctaaggttt ttctgtttta tatagtaaaa caaaaaatat tgcttttgtt gctaataaaa   34320
atttgtctgt aaggaaatat ttctcttaat attggagtta atactttgaa cattaatgtg   34380
cagtgtttag aaagattata aagaaatgag attggccggg cgccatagct catgcctgta   34440
atctcagcac tttgggaggc tgaggcaggc agatcctttg aggtcaggag ttcaagacca   34500
gcctgaccaa catggtgaaa cactgtctct gctaaaaaat acaaaaatta gccaggtgtg   34560
gtggcgggca cttgtaatct cagctacttg ggaggctgag acaggagaat cacttgaacc   34620
taggaggcgg aggttgcagt gagccgagat cacaccattg cactccagcc tgggtgacag   34680
agtgagactc tgtctcaaaa aaaaatttt ttttttaatt aaaaaaaaga aatgagataa   34740
tcagtactgt catttccttc attagaagcg ttagtactgt tacccttttt tacatgaatg   34800
aaaaggatta aagactactt tttgtttttt cctttgggaa ataaatgcat ggataataac   34860
agccaaataa aaagttttaa ttagaattgg atatctctat tcctattttc attcaaccag   34920
tatacttgtt ggaaggctat caaaatggac atgccattta aatgaaaaat ttccaattgt   34980
gatagacatg ttatttatga atattttctg tcctgaggaa aattaactat tagaaccagt   35040
tgtaaaagag atggtggctg ggcatggtgg ctcacacctt taatcccagc actttgggag   35100
gccgaggtgg gtggatcgcc tgaggtcagg agtttgagag caacctggcc aacatagtga   35160
aaccccgtct ttaataaaaa tacaaaaaat tagctgggca tggtggcaga gtcctgtaat   35220
cccagctact tgggaggctg aggcaggaga gtcgcttgaa cctgggaggc agaggttgca   35280
gtgaggcgag atcacaccat tacactccag cctgggcaac aagagtgaaa ctctgcctca   35340
aaaaaaaaaa aaaaaaaaa agagagatgg tatcaggtac tgcaaattct tagagtagct   35400
tctgactttg ctcagcccta tttataagat ttatctactg ggaggctcat tcaataggca   35460
cttgagagtc cggtgtcata gaaagttgtt aattttagag ttgtatgcag ccttctttag   35520
caatgaaaat cttttacaga ataaggctta agcttttca atgttttga ctgatttagt   35580 taacagctta atttatattg gcaccaagcc cagatctaat ggttataaac tcagtagttg   35640
gctgatacag taaaaactgt agtttcgttt tcttgttgtt tggtttaccc tttcattca   35700 agagtttaag tagatctcat atggtctggt cacatgtgtt ctgagtagtg gtcataccac   35760
```

```
accaggcata gcatttctgc tccgctgtga cttgattttt tacagactta agtttttagta    35820
caacttaatc tctcagagga agggttaagt tcctgagcat aggaattcat tttgggaatg    35880
tattttcttt tctttctttt taaaaattta tttgtagaga cagagtccca ctatgttgcc    35940
caggctggtc ttgaactcct gggctcaagt gatcttcccg ccttagcctc ccaagtgttg    36000
ggactacagg catgaaccac tgtgtcctgc cttcttttct ttttgagaca ggttctcgct    36060
ctgttgcaca gactggagtg cagtggtgta gtcatagctt actgtcactt cagattcctg    36120
gccacaagcg atccttccac cttagcttcc cgaagtgttg gggttacagg catgaaccat    36180
tgtacctggc ctctttttt tttttttttt ttctttttta aaaaattcct ttctaaaggg    36240
aaaagaacct aaggtgggtg gcttcctata accattttt tttttttttg atatggagtc    36300
tcattctgtt gcccaggctg gagtgcagtg accacggccc actgcaacct ctgcctccca    36360
ggttcaagcg attctgctgc ctcaagcctc ccgagtagct ggaattacag gcacccgcca    36420
ccatgcccag ctaattttg tattttagt ggcgatgggg ttcgccatgt tggccaggct    36480
ggtcttgaac tcctgagact tcaagtgatc ttcccaccca cccacctcgg cctcccaaag    36540
tgctgggatt acaggtgtga gctaccacac ccggccccta tatcctattt tatagtgttt    36600
cttgtttatt attttctctt tggatttgtt tcattttgat ccttgaaaat atgcaaagga    36660
tggaatctta attttggaat tgttttcttt ggttgaaatt ggaattatgt ggttttatg    36720
gcatttcccc taatctatta atgtgggagg aggcttgtgg ggagggaaga gccgtctttt    36780
tgagattatt agggagggaa accatttaat gacagaattg tatgactaca ttttattttt    36840
atgaggacta ctttgttaat ttacattctt gtgctctaca ttcatgaagt cagttatttg    36900
aaaccatgta atatatgtca actattaaag ttaagtgact tttatctgat aagagttgtg    36960
ttaaaataat catagagaat tgatgccttt ccagatgttt tcctgataca tcagggtttt    37020
ttttgttgtt gttttgctg ttatccagct tggagtacag tggtgccatc atagctcact    37080
gcagccccaa tctactgggc acaagggatc tccctgcctc agcctcccga gtagctggga    37140
ctacaggtgc actgcacctg gctaatttt aaaatgtttt tgttgagaca gagtctcgct    37200
atgttgccca ggcttgtccc gaactcctga gctcaagcag tcctcctgca ttggctttct    37260
aaagtcctgg gattacagac gtgagccacc aagcctgtcc tgatttagca gttaattaaa    37320
tataagtggc ctctcattct caggtgctct tacagtatga aaatgaagt tgtaaagttt    37380
gtttttaaag taactcagtg gaatgataga cagtggagac ttggaagggt gagggagtga    37440
gggtggatga tgagaaatta cttaatgggt accatgtgtg ttatttgaat gactgatacc    37500
gtaaaatccc tgacttgtcc attacacaat cttgcacgta atgaaattgc ccttataccc    37560
cataaattta cataaataaa agatcatgtc atctgttaaa aaattttta ataaagtaac    37620
tcagttaaat ttatggtatg tcaccatttc ttggcaggac tttgtgtcat tgtatcaaga    37680
ttttgaaaac ttttatacaa ggaatctgta catgaggata agagacaact ggaatcggcc    37740
aatctgtagt gtgcctggag ccagggtgga catcatggag agacagtctc atgattataa    37800
ctggtccttc aagtgagtct tggttgggaa attatttgac aacaattaca aaagggtttc    37860
ttcatttgag aaaatatgtt attataaatt gagtattctc tcaaaatagg agtagcagct    37920
gaggatacaa tatgattggt ttccttacat attcttcatt gttgagcttt ttaagatata    37980
tctttctatt acatttgata ctgtgttgga ttatagttca gaagaaaatt tggcttattt    38040
attttttgag atggagtttc gctctgtcac ccaggctgga gtgcagtggc gtgatctcag    38100
```

```
ctcactgcaa cctccgcctc ccaggttcaa gcaattctca tgcctcagcc tcccgagtag    38160
ctgggactac aggcatgcac cgccacaccc agctaatttt tgtatttgtt ttagtagaga    38220
tggggtttca ccatgttggc caggctggtc tcgaatgcct gacctcaagt gatctgtccc    38280
cctcagcctc ccaaagtgct gggattacag gcatgagtca ccgcgcccag cctggcttct    38340
ttatttttaa aaataactcc tattgataag aaacagtata caaaagttta gtctgtttta    38400
tttttggtct tgactttaaa aaaaaaaaaa aagaaaagct atcctttcca ttatgccact    38460
tatcagaatc aagtatccaa atttatttct ggatattttg atttctcaaa tgatttaagg    38520
atgatatgta gagtgttttt acttacatgg attgaatagt ttggaaaact ttttgtattt    38580
ttaacattgt atttgtttgt tgtttactt attcattat ttgagtcaga gtctcgcttt      38640
gttgcccagg ctggagtgca gtgtcacaat cttagcccac tgcaacctcc acctcccaag    38700
ttcaagtgat tctcccacct tagcctctct ggtagctggg actacagaga tgcaccacca    38760
tgctcagcta cttttgtat ttttagtaga gatgaggttt caccatgttg gccaggctgg     38820
tctcgaactc ctgccctcaa gtgatctgcc caccttggcc tcccaaagtg tcagagtctt    38880
gctctgtcac ccaggctgga gtgcagtggc accatcttgg cttactgcaa gctctgcctc    38940
ctgggttcac gccattctcc tgcctcagcc tcccgagtag ctgggactac aggctcctgc    39000
caccacaccc ggctaatttt tgtgttttt tagtagagac agggtttcac tgtgttagtc       39060
aggatggtct caatctcctg accttgtgat ccacccaccg cggcctccca aagtgctggg    39120
attacaggcg tgagccaccg tgcccggcct acagcttgcc ttcttagctt ggtcaaatat    39180
cagtgacacc ccttctcatg tgtatattca cagcaagttt attatttgta gtgactacat    39240
tgtattttac agtatacatg tgccatggtg tgacatgttg ggctgtgtta ataatctcaa    39300
aatctcaggg aattaaaaca gtaacagttt atccttatcg atacttcatg ttcatcctag    39360
gttggtgggg cccttgaacc attttgtcct tagttagggg cccaggctgc ctcagcttcc    39420
attgtatgaa atgtcactgg tctctgtatc tgaagaacag atgtggcaaa ttgtgcagtg    39480
gctctcaaag gatcctcatg tgtatatatt ctcatgtgcg ggagttactg agtatgtata    39540
tcttttaatg gataagtact gccaaactgc cctccaaaaa acaaacctga tattcttatg    39600
tacagtgtcc tgtaagataa ggtgattgtc ctggccaaca ctggatatca ttagttttaa    39660 aatcttatc actattaata aatgaaaatt gattatttta acttctattt ccataattgg     39720
tagtgtgttt gagattttt taatatagac tttgttctct ctgcttcctt ttgtgtcacc     39780
agttcattta atattacatg taagtacttt tttgctcatg agtttcattg ttttatgcta    39840
ttgatgcaca ggtatacagg gaatataata aagggtgtta taaacatggg ttcctacaac    39900
tatcttggat ttgcacggaa tactggatca tgtcaagaag cagccgccaa agtccttgag    39960
gagtatggag ctggagtgtg cagtactcgg caggaaattg gtaagtgaaa gctgtatttg    40020
gccagctgct gtttttgaca ttgttttagt caggggcaaa taatagtaat attgacctag    40080
agtattaaat atctacactt tgtcatgtca tttagataag gtgaagaatg ctttgttttt    40140
ctgaagtgtg atggatgatt tcaatgcttt caacacattt tgagatgtgt ttatcttttcc   40200 caatgtgtta tacatataga atgtccctcg aaaaatcctg ccagtgtttg tttcatttat    40260
aactttaatg ttgatttcat tggcttttgc aaatgttagt ggttaagagt gccacttatt    40320
aggatgttgg gcatatgaga gttaatctgc tttcatactg gtacatgggg gctaataata    40380
attcctgcct tatagagctc ttttaagaat tacgtaagct aatccatgta gagtacttgg    40440
aacatagtag acaataaata taaactcttt ttattattgt tttaagtttg taaaatataa    40500
```

```
aagagtaata actttatata aagagattca atttatttta attcagcgga agatttcaga   40560
ttgttccaat ttgattcaga gaactgacaa ccctggaagt tatgaaaact ttccaaatac   40620
ttattactgt aagcacagta gattaaaaga acagttcatt gttagttatt tctcagggtt   40680
ctagggattg gcaagcacag ttgggtgctt cttacccaag gttcctctca cggttgcact   40740
cagtggtggc tgtatggctg gagacatgaa gccttcttca ttcgcatgtt tcacctaggc   40800
tgcggtggct ggagctctgt gtggcctctc catgtttcta gcttgggttt cttcatacca   40860
tggtggtctt ggagagttgt tcatcatgca tggctgcagg cctctagagc aagcatgcaa   40920
agatacctga ctgaagccag gcacggaggc tcatgcctat aatcccagca ctttgtgagg   40980
ccaagatagg aagatcagct gaggccagga gttcgagacc agtctgagca acatggtgag   41040
acctgttctc taaaaaaata aagataaagt agccgaacgt ggtggcgcat gcttgtgatc   41100
ctagccattc aggaggctga ggccagagca tccctcgagc caaggagttt gaggctgcag   41160
tgagctatga tcgtgctact gcaccctagc ccatgacaga gtgagacact gtgtcaaaaa   41220
acaaaaacaa ggatacccag ttgaaagttg gaaggctttt tatgccctag ctgtacaggt   41280
cccaaagtat catttatgcc tcttctattg gccaaagcgt cgctaaggtc agcccagatt   41340
caagggttgt ggggattgcc ctcctccacc tccaaatggg aagaataaca aagaatttgc   41400
atccatattt aatcttccat agcaactctg tcagctcacg aaatttaaaa caacatgaag   41460
acagggaaaa aaataaaatt gtgcagattt ttatatctat ttatttagat agctagatac   41520
atggatatat agatagattg atgcatagat ggatgcaggg tctctgttgc ccaggctgga   41580
gtgcggtggt gcagtcagct cacttcagcc tcaaacttcg gtactccagc catcctccca   41640
cctcagcctc ctaagtagtt aggactatag gtgcacgcca ccatgcccag ctgattttt   41700 aatgtgattt ttgtagagat ggggatctct ttcaagaggc tatgttgccc agggtgttct   41760
tgaaatcctg gcctcaagtg attctcctaa ctcagccttc cagaacactg ggattatagg   41820
tgtgagtcac catgcctggc cccaccatct aattttaaat attttcattc ctcctaaaag   41880
aaatgctata ctcagtagca ttcattggat actgtttccc ttcccctac aagtccttgg   41940 caaccagtag tctacttttt gtctttatag atttgcctat tttggacatt aaatataaaa   42000
ggaattgtat aacatttggt cttttctgtc tggcttcctt cactagcaca atattttcaa   42060
attcatccat gttgtagcct gtaacagcac tccattcttt tctatgactg aataataatc   42120
ctttgtgtga gggtgccacg tcttgtttat ccacttatca cttgatggtc atttgggttg   42180
tttctacttt ttggctattg tcagcagtgc tgctgtgaac gtgggtgtac aagtttttgt   42240
atgatatatt tttgtttctc ttgggtttat acttactagt ggaattgcta ggtcgtatgg   42300
taactctgtg tttgactttt tgaggaattg ctaaactgtt ttccaaagag accgtactgt   42360
tttacaatct ctccatcgat gtatgagggt tcctattcat ttttatatca tcttccagtc   42420
atcttgtttg tagcccaact ttaacccttg attactttgc tacctgttcc ctctggtttt   42480
taagcttctc tagggttcca tacagtgaat ttacttggtt ttcaaaggat tccactctat   42540
aagggcatag atatgacctt cttctaactc tgtcattttc cagttgtatt agtttcctgt   42600
ggctgctgta acaaaatatc agaacagagt gacttaaaac aacaaaaatg tctagtctca   42660
taattctgtg ggttataagt ttggggtcta ggtgtcagca gggccatgct gtctgatgct   42720
ctggagaaac cttcctagct tctggtgtcg acagcaatcc atgacgttcc ctggcttata   42780
gcacatcact ccaccacacg gctgtcttcc tgtgtgtcaa acattgtcgt cttctggccg   42840
```

-continued

```
ggcacagtgg ctcatgcctg tcatctcagc actttgggag gccaaggcgg gcagatcact   42900
tgaggtcagg agttcaagac cagcctagcc aacatggtga aaccctgtct ttactggaaa   42960
tacaaacatt agctgggcgt gatggaaggt gcacgcctgt aatcccagcc actcgggagg   43020
ctgaggcacg agaatctctt gaacctgtga ggcagaagtt gcagtgagcc gagatcacac   43080
cactgcactc cacctgggca acagagtgag actctgtctc aagaaaaaca aaaaacagc    43140 attgtcttct gtattccttc tgtgcatgtc tatcactgtg tccaaatttc ccttttctat   43200
aaagacatta gcatccccct aatggcctca ttttatttat ttatttattt atttatttat   43260 ttattttaa atctttgta aaatttttt attgatacat aacatttgta catttgtgtg      43320
gggtacatgt gatgtgttgt tacatgtata gaatgtgtat agaatcaagt caaggtattt   43380
agggtactcg tcaccccaag catttattat ttctatatgt tgggatcatc aagtcctctc   43440
gtctagctat ttgaaatata caatacattg ttttaacta tagtcaccct actctgctat    43500
caaacattag aacttattc ttctaactct atatttgtac ccatttacca gcttttcttc    43560 atctccccg ctcccctac ctcatctcaa cacacatcct tccagtattg ttttactcgc     43620
tacctccatg agattaaatt tagtgaggaa ggcatgttaa aagctgacat aggccaaaag   43680
cgaggcctct tacaccaagc aattagccaa gttgtgaatg caaaaaaagt tctcgaagaa   43740
aattaaaagt gctactccag tgaacccaca aattataaga aagtgaaaca gccttttatt   43800
gctggtagag agaagttttt agtggtctgg ataaaagatc aaagcagcca caacattccc   43860
ttaaacccaa atctaatcca gaagaagatc ctaatcgctt caattctatc aaggctgaaa   43920
gaggtaagga agctgcagaa gaaaagctta agcctagcag aagttcattc atgaagctta   43980
aggaaagaag ccatccccac aacataaaag tgcaaggtga agcagtgaat gctgataact   44040
tcagcaagtt atccagaaga tctagctaaa ataattgatg aaggtggcta caataaatca   44100
cagattttca atgtagatga aacagcttta aattgaaaga agacaccatc taaaactttc   44160
acagctagac acaagtcaat gcctggtttc aaagcttcaa aagacaggtt gaccctactt   44220
ttaggtgcta atttaagtt gaaccaatg aatgacctca ttttaatttg attacctctg      44280
gaaagttcca gtttccaaag aaggtcacat tcttctggga atgaggacgt caaaatatct   44340
tttttggtgg gacacaatgg aacccgtagc atcatccttc tgtatatttt ccattttcat   44400
taattgtgtt cagaattaca gatgtccact aattaataaa aaattgagct tttagctttt   44460
atttcttggt tatccagttg ttttgtgatg attttcaaga ggaagatggg agtagaacat   44520
ttttatttcc ccctgccttt aaaacagagt ttctaactgg cactccagaa atgacaagcc   44580
ttgtgatcta atcctgtggt taaggagca ttgtgcagtg gcgacatata gtaaggatac     44640
attatgcctt tatggcattt gatattttat aaagtgctcg gctggatgcg gtggctcacg   44700
cctgtaatcc caacactttg ggaggccaag gtgggtggat ctcttgaggt caggagtttg   44760
agaccagcct ggccagcatg gtgaaaacctg tctctactaa aaatacaaaa tagtcaggcg   44820
tggtggtccg cacctgtaat cccggctact tgggaggctg aagcaggaga attgcttgaa   44880
cccaggaggt ggaggttgca gtgagctgag attgcgccac tgcactccag cctgggcgac   44940
agtgcgagac tctctctctc aaaaaaagaa aaaagctca aacgtattat ctcttttgat    45000
cctcacaaca atgtcatgag gtagataggg caaattatta ttgctattta gaagtattta   45060
gcccagagag ttcctaaggg ctttgattaa gcaagcctta aggacacatg gcatccaagt   45120
ttagcattct tctttcccgc atcttttctc tctgtaatgt catttagtcc ttaaagattt   45180
gagtaccaat ataaaattgc ggtacaaatt taccagtcag ttcacagtga gggaagaacc   45240
```

```
tttttttttt ttttttttga gtcagagtct cgctctgttg cctaggctgg agtgcagtgg   45300
tgcgatctca gctcactgca acctctgcct cccaggttca agcgattctc ctgcctcagc   45360
ccccgagtag ctgggattac aggcacacgc caccatgcct ggctaatttt tgtattttga   45420
gtagagacaa ggtttcacca tgttgccagg ctggtctcaa actcctgacc ttaggtgatc   45480
cgccctcctt ggcctcccaa agtgctggaa ttacaggcgt gagccactgc accctgccag   45540
gaagaaacgt ttttacctat cttttgctgt ataacaaacc atctcaaaac ttagtggttt   45600
aaaacagcaa cagatttatt tgctcatgat tctgcaattt agggagggcc tgatgttatc   45660
ttagctccat gtggtattgg ataggcaatt atgactgtgt acagggtatc caagatgtct   45720
taactcacgt ttgacacttc agctgggtgg caggaagggc taagggctgg ctgggcatct   45780
ctgtttctct ttctctctgt ctccccctct ccttacgtct ttctctcctc cttccatagt   45840
ctcttatccc tcagttccca tcccccgcc catgttctgt ttttgcaaca ggccagttag    45900
attgttttac atagcagctg acttcaaaag tgtaaaagca gattttgcta ggcctcctaa   45960
ggcctagacc tggaactagt atgcacaaac aggaatggga gaattttttc gcagccccct   46020
ttggggaaat tccactgcag gtgctgaatc agattttatt caactattgt gttctttatg   46080
agcacatatt actcttcaca atattatgaa gaatattact cttcataata ttgactcctt   46140
catagatctt agtctgaaaa ggacacaaca catatactat gatttctttt aataaagtga   46200
tgagtaattc ttaaattcag gattttgtga tactgacttt attaacttct tcacacagga   46260
aacctggaca agcatgaaga actagaggag cttgtagcaa ggttcttagg agtagaagct   46320
gctatggcgt atggcatggg atttgcaacg aattcaatga acattcctgc tcttgttggc   46380
aaagtaagat actctgtcat ttatgaaaac tccctcatgt atatcttctt ttgttttgaa   46440
aagcagtcag agtgagctaa aagctgttat aaactttagg ctaaacatag tttagccaaa   46500
gatatttcta ccacaaattg ttttttcttt ttttttttt ttttgagatg gagtcttgtt    46560
ctttcgccca ggctggagtg cagtggcacc atctcagctc actgcagcct ctgtctcttg   46620
gattcaagcg attctcctgc ctcagcctcc caagtagctg ggactacagc tgtgtgccac   46680
cacgcctggc taattttttg tattttttagc agaggcgggg tttcaccatg ttggccagcc   46740
tgggcaacat agtgaggcct cgtctcaatt tgattttatt ttttaaatta aaaacaattt   46800
gtggccaggc gcagtggctc acacctgtaa tcccagtgct tgggaggct gaggcaggtg    46860 gatcacctga ggtcaggagt ttgagaccag cctgtgttta tatatttata tacatatata   46920
taatattgta tattatatat atatataaca tatatgtatg ttacatatta tatatattac   46980
atattacata ttatatatat aatatatata tccccaagtg ggtagtgtgt gtgagagggc   47040
acaatctgta tgtaaatgta aattatattt cagcagattg gtactctcat cctgaaaggc   47100
cccttgaggt tatttattct catgtttaac atgacactta ggaatggtat attgaaaacg   47160
tggtggatta actcaagcag gagaattgag ttttgttttt ttggttgttt atatggtcac   47220
acttagctgt gtgactgtga gcatgtcaaa taatctttct gatcctccaa gtttcttttg   47280
taaaatgagg tggttgagct agattaactc taaagtcctt tttagttatg cagtgtatgg   47340
gtctgtaagg tacagatggg acaaatagaa acaaacagc aagataggag atttaaaccc    47400
acctgtgttg ataaacatta aatataaatg gtttgtacat tccaatgaga agacaaagat   47460
tgtcggataa aattaagtag gtttcctaat gtaaaatagc aacctatttt aaatatgaag   47520
acacagaggt taaaggaaa aggatagaaa aaaaatacag catgcaaata ataatcagaa    47580
```

```
gaaatgtgaa gtgcctgtat taatataaac aaagatttca gagcaagaaa tatttctggt    47640
gataaagaac attgtgtaat gattaaggaa ttaattcatc aagaggttat aattttaaat    47700
gtgtaggtgc ttatcccatt tatgcctaat gttccattat tggaacgcta agcatgtggg    47760
agttatttat atcctactgc tcaaggtcat cgccagggtc tgattttgca attcaaaaaa    47820
ttgtaacctc tggcataaat gggttattaa cagagcgtca aagtacgtga agcagaaatt    47880
gatgaaacta aaagaagtag acaaatgaaa aattgtaatt agagacatta accctctct    47940 ctttttttt tttttttttg agacagagtc tcgctctctt gcccaggctg gagtgcagtg    48000
gtgtgatttc ggctcactgc aagctctgcc tcccgggttc acgccattct cctgcctcag    48060
cctcttgagt agctgggact acaggcgccc accaccacac ctggctaata ttttgtattt    48120
ttagtacaga cggggtttca ccgtgttagc caagatggtc ttgatctcct gacctcatga    48180
tctgcctgcc tcggcctccc aaagtgctgg gattacaggc gtgagccact gtgcctgcc    48240 ctaaccctc tctcttaatt aacagaagaa tgaaacagaa aatcagtaat gatatagaat    48300
gtttggaaaa cactgtcaac cagttgacct aattgagagt catgaaacac ttcactcaac    48360
aacagcaaaa catttactac caaagaccat attctaggcc attaagccag ttttggtaaa    48420
tttgaaagta ttaaaattat tcaaagtatg ttctgtgatc acagtggaat ttaaattaga    48480
aattgataac acaaagatat ctggaaaacc tttgaatatt tgaaaattaa acaatatatt    48540
tctaaataac ccatgggcca aagaagaaaa aacaggggaa aataaacata ttttgaacta    48600
aatggaaatg taacctatta tagtttgttg gatgaagcta aagcaatgct cagatggaaa    48660
tgtatagcat taaacgttta tacaggttga gcattcctaa tcccaaaatc tgaaatctaa    48720
aatgtttcaa actcgtaaat attttgagtg tcatcatgac agctcaaaga aaatgcttag    48780
gggtgctaaa ccagtaaata taatgcaaat aatccaaaat ccataaaaat ctgaactctg    48840
aaacacatct ggtcccaagc attttgaata aggaatattc aacctgtatt agaaaaaaag    48900
taaagcagcc agactccatc ttaaaaaaaa aaagtaaagc ttgtagctta aaaaattaga    48960
aaaagaaaaa caaattaaac ccaaactaag cagaaggaag aatataatga tgataaatgc    49020
aaaaattaat gaattagaaa atagacaata ggaaaattag tgaaaccaaa gctgattctt    49080
tgagaaaatg aatatagttg ataaatctgt ggccagaatg gtcaggataa aagagataa    49140 ggtgcatatt accagtaaca ggaatgagag aggggggacat cactcacgt cctatggaca    49200 ttaaaggata ataagggagt attaagaaca acttcatgcc aaaatattca acaacttaga    49260
taaaatacac aaaattcctt gtaagacata aatgtatggt tctttgactt cacgttataa    49320
tacgttgctg tcctgcattt tgaagtacaa gcctgagatt cttatttgtt agaattttta    49380
acactagagg attagaaaat ctcatcttgc tcttctctct gtatgcttac aagctctatc    49440
agaggattat ctagaattag acgttttcta cacagacctg gaagatacaa ccataaggat    49500
ttatattcca gggccgggcg cagtggctca cgcctgtaat cccagcactt tgggaggctg    49560
agacgggtgg agatcgagac catcctggct aacaggatga aaccttgtct ctactaaaaa    49620
tacaacaaat tagccgggcg tggtggcggg tgcctgtagt cccagctact ctggaggctg    49680
aggcaggaga atggcgtgaa cccgggaggc ggagctggca gtgagccgag atcgggccac    49740
tgcactccag cctgggggac agagcgagac tccgtctcaa aaaaaaaga tttatattcc    49800 aaatcaaact ataattgaaa tattattaaa tattgtttaa tctgttaaag acagtaactt    49860 atccagttt aatgatcctt tgaatctgat actgaatttc catgtgaggt ggttaattgc    49920
tcagtttgat ggcagggtgg ggcagtatat tgattaagag cataggttct ggaagcagac    49980
```

```
acttgtctta tttaataatt attttgtggc cgggcgcggt ggctcacgcc tgtaatccca   50040
ggactttggg aggccgaggc gggtggaaca cgaggtcagg agatcgagac catcctggct   50100
aacacggtga aacccgtct ctactaaaaa tataaaaatt aggcgtagtg gcaggcgcct    50160
gtggtcccag ctactcggga ggctgaggca ggagaatggc gtgaacccgg gaggcggagc   50220
ttgcagtgag ccgagattgc gccgatgcac tccagcctgg gcaataatta gtattgctat   50280
tattattttg ttactgtgct gtgaccttg agcaagattc taaactcctg aacaagagtg    50340
tcctcatatg taaagtggga gtgataatag tgtctgctac atagaattat tgtgaggatt   50400
aatagtaata atgcttttaa atcttttaac atgatacctg aaacattaag cgcttagatg   50460
ttaactgcta gtatgaatac ctttttatttt tgaaccaaag atttaataaa gcttaagaat  50520
aagttctaag ggaaaaagac agattgatac attgaaatgc tgaataaggc tgtcaaaaa   50580
aggctgtcta aaaagagttc cttttttgcca gaaaaaaga acataatgct tttgcaggtt   50640
tgccagaaaa atatttagct ggaaagagaa gaaaataaaa ttttgtgcgg aggggaaggg   50700
aagggagggt tcttttttaag atagagttga atgccaagag tggtaagtaa agaatttgac  50760
ttgctgaaga gaaatctgac ttctctttat tttctccccc agtttcgctt tttcaatttt   50820
aacactttttt tgaaacttta atttagactt acaaaaagag ttacaaaaga gtacagagag  50880
ttcctgtata ccattcattc agcttcccctt tatgttaaca tcttgcataa cagtggaact  50940
gtttcttaca gctaagaaat taactgtgac acaatactat aactaaagta caggacgtat   51000
ttggttttca ccagttttttc cgcttcagga tccaggtgag gatccacatt gtctttagct  51060
gttgtagctc ctcagtctcc tccaatctgg gatagttcct gtttttcttt gtctttcatg   51120
accttaatac ttctgaaggg tactggtccc ttatttttgta gaatgtctcc aatttgggtc   51180
tgtctgttgt gttgttatgg tttgattgag tccgtgcgtt attgagaaag ctaccacaga   51240
agtgatacca ttctcagtga atcatgcgag agactatgtg gttttgatac atattactga   51300
tgatgtaaat cttaatcgct tgtctcaggt gtcagcgggg attttctact accaacttac   51360
tgcttttctc tttgtaatca ccatatattg tggcagagat actttgggac tgtatatagc   51420
attttggatt aaactttcac ccactaactt tagtatgcat ctgtgatctt gcctgtggca   51480
gttattacct tggtgttctt ttttttttttt tttttttttt ttttgagatg gagttttgct   51540
cttgttgccc tggctggagt gcagtggcgc catctcagct cattgcaacc tctgcttcct   51600
gggttcaagc aattctcctg cctcagcctc ctgagtagct gggattacag gcacccacca   51660
ccatgcccgg ctaattttttt gtatttctta gtagagatgg ggtttcacca cgttggccag   51720
gctggtctca aactcctgac ctcaggtgat ccagccacct cagcctccca aagtgctggg   51780
attacaggcg tgagccaccg cacccggctt accttggtgt tctaatggtg attttctat    51840
ttttctcatt ctttctatac ttactaatta gaattttttgt gtaaggaaga gttcttgctt  51900
ctcccttatt tatttctgtc gttgtgggtt tgtgaatatt tttattattt ggcttataat   51960
tcaacacaat tgcttctttt ttgttgctcg agttttagtt ttggccattg ggagctgctt   52020
caggtgggta cctgtgtcct ttgaatatat aataacttt tttttttttaa gcattcttat   52080
actttctggc atgataaaat gctccaggat catcttatat tttccctatc ccagtttttgg  52140
aattaaccag ttctccaaga agtgctggtt ctttttttttg gagaatgata tttagaaacc   52200
aaggtctggg aactaggtgt gtttattgct gaaggagtat cactgcttct cacctctcag   52260
tgactagagc tagaaaatgt atgtatatat gcgaactcat gcatacacac acatctgtgt   52320
```

```
gtgtgtgtgt gtgtgtgtgt gtgtgtgtgt gtgtgtgtgt gtgtgtatgc atgcataaag    52380
atttgaaagc caggagtcta ttgatactgc cggctctagt cttctccttt tccttattct    52440
ccttcttctc cttctcctcc ttctcctcct cttcctcctt ttcctcctct tcctcctctt    52500
cctcctcctc ctccttttt tttttttttt ccccccagac agagtctccc tctgttgccc    52560
aggctggagt gcagcagcac aatttcggct cactgcctca ctgcctcagc cttttgtgta    52620
gcagagattt gaggcgcctg ccaccacgcc cagctaattt ttttgtgttt tcttttagt    52680 agagatgggg ttttgccatg ttggccaggc tggtctcgaa ctcctgacct caagtgatcc    52740
acccaccttg gcctcccaaa ttgccaggat tacaggcatg agccaccatg cctggccact    52800
tcatttttaa tctgtacatt tttaaccagg tagcttttt atcttaataa atactatgtg    52860
cataataaaa atttcaaaca caactactgt tacaagtttc ttaagtattc ctttaagaat    52920
attctgtaat aaataagcat gtatatatat agttgaccct tgaacaacat ggtttgaacc    52980
atgcaggtcc acttacacgt ggattttttt caaccaaata tggagcagaa atacagtttt    53040
cagccaggca cagtgtctca cacctgtaat cttggcactt cgggacgctg aggcgggtgg    53100
atcacctgag gtcaggggtt caagaccagc ctggccaaca tggtgaaacc ccatctctac    53160
taaaaataca aatattagct gggcctggtg gtgggctcct gtaatcccag ctagctggga    53220
cgctgaggca ggagaatcgc ttgaatctgg gaggcagagg ttgcaagtga accaagatcg    53280
caccactgca ctccagcaac aagagcaaga ctccatctca cacacacaca tacacacaat    53340
atagtattca tggaacacaa aacccaagta tatggagggc ctgcaggtcc cacagggcca    53400
actgcaggac atgagcatgg atggatttgg ataaatgtga gggtgaggca gttctggaac    53460
caagtcctcc tgtagactga gggatgactg tgtgtctttg tatcttctct cttcttttta    53520
ttctcgtggg agcatgctat atactttctg cacccttttc atctaattgg atattatgag    53580 gctattttg acagagaaaa acctttttct gagttgagat ctgacaggtt gaagggcccc    53640
ctgagagatg gaagagtaag aactgcagtg aaaaaaaaaa ccaaaccgag atcttcaacc    53700
ttttcttagt tgccttagca gaaactgatg tttgtgtgtt aaagcaaagc ttgtttgggg    53760
atttttaaga caaaactgaa gcctacagtc catgctatgt ggggaaaaag ttaataagta    53820
ggatcttccc tggactctgg atatgagtag tagtgagaga atgcaccatt tccacagaca    53880
tgaccccatc agctgccatt tcccacagat aaacagaaca tgatactaaa actacatgga    53940
attctctcac gtaaagaaac caaaacgttt tagagacgga tgtgtcatgt tttagataca    54000
aataaagacc tgttgccata tatctgagta tttacatcag tcatgggact gaagatatta    54060
aattaaaagg ctagaatttt gcatctactt ttaaggtgtc tttacaaaaa acaaatgatc    54120
gtgtacacct ttttcctctt cttaaaattg atcactgtgc tgttgtgcac aatttcctta    54180
ataagataca gctattagtg tttgtggcat tttgtgattt gtgtaactaa cccttcccc     54240 tccagcttct tacctttctg ttcctgtgat gttgcagggt tgcctgattc tgagtgatga    54300
actgaatcat gcatcactgg ttctgggagc cagactgtca ggagcaacca ttagaatctt    54360
caaacacaac agtgagtttg ctgaagaatt cactgctggc cttggttttg ctattctttc    54420
gatccatggt gggagttaac attagttata ttagcacttg aaagtataaa tgaagacaaa    54480
gtagcaacat ttaaaatgtt cttccggtcc agtctttaa aattagaggt tgatggaagc    54540
ctcttgtaca aatataatac tatccttta tttgaccatg aagttttcca tcccatttcc    54600
ttgtttacag atccgttact caaatacatt tactcgatga ctatagtgta tcttgccata    54660
agactaacag tatttaagtg aataaatcaa gatctctgac tggttaacga agagacttaa    54720
```

```
tagataagcc agtccttaca atatagtgga caggtgctga agtacagcta tgaatagatg   54780
ctgtgggagc acagaggagg gtggccctga gccagacctt tcctccctca gtggaaatat   54840
ctttgtgtat tattaaaatg attatttaga ataaaaatgc gtaactttca tagttaaaac   54900
acacacatag gcagaaaagg tgaccaaact gtatgttaat agcatctttt cccaaaatgt   54960
gtacaggcac agacaaaagt ttggaagaat gtataccaaa atgttaggtg tgtacccgtg   55020
gatggaagga tcatagatga taacatcatt tttgttttg ttttgtttt tgtcttgtct   55080
aaaatgtttt acagtgagaa atgagatctt attaaatatc actatgtaac ctgttatttt   55140
ctttttttt tttttgaggc tagagtctcg ctctgtcacc caggctggag tgcagtggct   55200
caatcttggc tcactgcaac ctctgcctcc cgagttcaag cgattctcct gcctcagcct   55260
cccgagtagc tgggattaca ggagcgcgcc accacctg actaattttt agtattttta   55320
gtagggacgg agtttcactg tgttggccag actggtcttg aactcccgac ttcagttgat   55380
cctcccgcct tggcctccca aagtgctggg attacaggtg tgagccatca tgcctggcct   55440
cttttacaa tacacggtga ttgttgtttg tcattacatg taactctatc tcattcttaa   55500
ataccagtgt ggcagttagt gcctgggtgt gccctcattt aattgccccc tcaattggac   55560
atcggggctg tttctaaatt tttctactgg gaacagcact acagttacag ttttgtacca   55620
tcatctggtt agtgccttag gataaatttc tagcagtctc agaatgcatg gttaaaagag   55680
tatacatttt taatactttt ccaaattgcc tctaagcatt atatgaactt ttttttttc   55740
actttttattt taggttcagg ggtacatgta caggtttgtt atataggtaa attgcatgtc   55800
tcgggggttt gtgtacagat tatttcgcca cccaggtaat cagcatagta cctgataggt   55860
aggtagtttt tcgaacctta ccctcctcaa cctccctgc ctcactctca agtagacccc   55920
agtgtctgtt gttcccttag tcgtgtctgt atgtactcag tgtttagctc ccacttacaa   55980
gtgagaatat gtggtatttg gttttctgtt cctgtattag tttgcttagg gtaatggctt   56040
ctagctgcat ccatgttgct gcaaaggaca tgatctcatt ctttcttatg gctacatagt   56100
attccatggt gtatatgtac atatatatat atatattttt attttatttt ttgagacaga   56160
gtcttgctct gtctcccagg ctggcatgca ttggcatgaa ctcagctcac tgcaacctct   56220
acctccccag ctcaaccgat cctcccatct cagccaccct agtagctggg actacagatg   56280
tgttccacca cgcccggcca agttttttgt ttttgttttt ttgtgttttc tttttgtatt   56340
ttttgtaaag atggggtttc accatgttgc ccaggctggt cttgaactcc tgggctcaag   56400
caatccaccc accttggcct cccagtactg ggattatagg cataagccac cacgcctggc   56460
ccacattttt ttaatccagt ctactgttga tggacattta gattgatcct atgtctttgc   56520
tgttgtgaat agtgctacaa tgaacataca catgcttgca tcttgtatga attttttcctc   56580
aacaacatga gattgactgt tcctactcac tggccaacat aggctatggt gaatcatttt   56640
aaatcttttcc aaatctaatg aggaaataat atgttagttt ttatttcatt gcttattaga   56700
tatagaacaa cttttttgcat ttttactgtt tttttaactc tacttgtaag ctaatgtgtt   56760
tgtatttctt tataaaattgg ccatttttcaa attgtttcta ttttttactg attataagag   56820
ccctttatat taattatctt ttcctttatg ttgcattatt ttattattat tttttgaga   56880
cagggtcttg ctgcatcacc caggctggag tgaagtagca gaaccacaac tcaccacagc   56940
cttgacctcc taggttcaaa tgattctcct gcctcagtct cctgagtagc taggactgta   57000
ggcatccacc accatgccgg actagtgttt tttattttt atagagacaa agtctcgctg   57060
```

```
tgttgcccag gttggtcttg aactcttagg ctgaaacgat cctgctgtct cagcctccca    57120
aaatgctggg attacaggag tgattcacca tgcccagact gcactatttt tatatttttg    57180
actttgtttt cagtgtcttc ctgtacagac tcatgaaaat gttttttgttg ccacacttac    57240 tgttttacga ctttcggatt ttacacaata ccctcctcat tctcagatca taatgttatt    57300
ctttcatgtt ttcttctggg agttttgcga tatatttttt atttaaattt atgtggaatt    57360
tgggggcata acattggaga gattgaattt ttttttctaa gtagataata tggttaagca    57420
ttctgctata ggtatttctt ttttttgaaa cagtcttgct ctgtcaccca ggctggaggg    57480
cagtggcgtg atcttggctc actgcaacct ccgtctcctg ggtttaagcg attctcatgt    57540
ctcagcctcc caagtagctg aattacaggt gcccaccac cacaaccggc taattttttt    57600 tgtatttttta gtagacag gttttgcca tgttggtcag tctggtctcg aactcctgac    57660
cttaagcgat tcacccgcct cggtctccca aagtgctaag attacaggcg tgagccacca    57720
cacctggctg atgcttcttt tatctaaaat tttgaccagt attatttttc tcctccttct    57780
atatataaac agagaaaact aaaataattc ctgtgttttt acttgtcttc agctgatcgc    57840
catacattgc tctctgccta agaactggag gctttgcagg acttggggag gccaaggagg    57900
gcagatcacc tgaggtcagg agttcaagac cagcctggcc aaaatggtga acccccacct    57960
ctactaaaaa tacaaaaatt agctggatgt ggtggcatgc acctgtaatc ccagctactc    58020
aggaggctga ggctggagaa tcacttgaat ccaggaggcg gaggtttcag tgagcagaga    58080
tcacgccact gcactcctgc cttggcgaca gagcaagact ctgtctcaaa aaaaaaaaaa    58140
caaaaaaact ggaggctttg agtcaggacg taatttactt ctgtagggaa catctcctga    58200
atcttgatta ggtcgtatgc agatttttttt cttagaaatt actgaatgtg taagcacagt    58260 cacaaccta gactatctta tttgtgtttg tgttctgtgt ttttattacc ttatctcttt    58320
ttctgtcaaa attgttttct gcaaagagca aaatcatgta cttttataac tccttcctcc    58380
agttacaagc aatacagaat acaaaatcag attttatgat agggccaggc gtggtgctca    58440
cgcctgtaat cccagcactt tgggaggccg aggcaggcgg atcacctgag gtcagaagtt    58500
caagacaagc ctggccaaca tggtgaaacc ccgtctctac aaaagtacaa aattagcctg    58560
gcgtgatggc gggtgctggt aatccgagct acttgggagg ctgaggcagg agaattgctt    58620
gaaccttgga ggtggaggcc tcagtgagga gagatcacac cattgcactc cagcttggat    58680
gacagaggga gactccatct caaaaaaaaa aaaagattt tatgatagga tgtctcccac    58740
ccctattaag tattccccag acttaatgtt gcttaaattt ggggggagttt tttttaagga    58800 cttcatttca gggcaggtat tttaagtatg aaatctgtag tgtggcaaca atggtcttca    58860
aagcatttgt ctttaacaag gaaattatga tcatcattaa tggcagtagc agccaagttg    58920
tttccaggcc cattaaccac cataagaacc aacagagcca caagaacttg gttgtttatg    58980
gacaactgat gaagtcaaac atggaacaat ttcaactgat tgtcaggctt gcttaacaca    59040
cagacttata catgccccag acgggtgtat ttttaaccca gtaccaaaat aaaactcttt    59100
aacaagcgtt tattgagtac gtcctgggtg aaaggaaatg gagcacgcac tgtgaagttt    59160
ttttacgcct tgcgtttgtt tttttaggag gagtatgtgt ctgtgatggt ttattcacac    59220
tctctcgctc tgtctttttt acgcatttat ttccgaatga ctcactggga ttagagatac    59280
agtttgattc tgtattttttc gataaacaca cagaagctaa cttaatggca gggtatttaa    59340
catgagacac tggtcatttt ataaggaagc taatgaactg agttagccac caccgtcctt    59400
tagtcaagtt tcgatggttt tgaacatttg ttacattttg gatttcaatt caaggtggca    59460
```

```
ataattcacc tattttgccc tgcttttttc tgcccaactc taattatgtc ctttgctatc   59520
tgaggcatgg tttctgaatg agaaatatat ctctgcattt ccggaataaa gttaggaaag   59580
aggaagatgc ggtataactg ttcttttttg tgctctgtag atatgcaaag cctagagaag   59640
ctattgaaag atgccattgt ttatggtcag cctcggacac gaaggccctg aagaaaatt   59700 ctcatccttg tggaaggaat atataggtaa tcctgcttta ttattcttac ctttgtgact   59760
tggccccatg aagtcataga atttttaac tgaagggaac attagtctat cccctctgg    59820 aaactaagga gacagtgttt ataagtcgct aaaatacctg gaaacagagt cagcattaga   59880
acagaagtct ttttgtctag ttcttcgtta ttctttccat aatactacat ggtcaccaaa   59940
tcccctttct atttgagtct tttatttttc tagtttgtag agggaaccta tatgtagggg   60000
caagaattgg aatatatatt ttaatatgtc aaaacaaatt acacaccatt taattttaat   60060
aaatatttta ttttaggctg agtgcagtgg ctcacgcctg taatcccaac actttgggag   60120
gcaaaagtgg gaggtcgctc gaggccagga atttgagacc agcttgggca acatagtgag   60180
accctgtctc tgtaaaaaat aaataaaaat taaaagaaa tattttatt tggttaacct     60240 ttacagctt tacacgtatt tttaccacct aattttttt gttctttgt gtcattttaa     60300 ttgcctgtgc aacgtgatgc aaagtctcat gttgcctgta attacaagct ttagaagaat   60360
ctgctgtgac cttaattatt tttgtcgtga attaagattg cttgtgtttg gtgcttgttt   60420 tttgttttt ggtggtttgg gtggcttttt ttttaagatg aatctcgct gtgtcaccca    60480 ggctggagtg cagtggcggg atgtcggctc actgcaacct ccgcttcccg gttctcctgc   60540
cttagcctcc cgagtagctg ggattacagg tgtgtgccac caagcccagc taattttgt    60600 attttagta gagacggggt ttcactgtgt tggccgggct ggtctcgaac tcctgacctc    60660
aagtgatccg cctacctcag cccaccaaag tgctgggatt acaggtgtga ccaccgcgc    60720 ccagccagtg cttgttttaa aagtccagtt ttctttcccc tagtcttttg ccttgccatg   60780
gcttcatcta cctttgtcag tttaagccac agatacagtt gtcagaccat ttaaaaccca   60840
ataaactcag ccgggcaggg tggcttattc ctgtaaccc agaactgtgg gaggccaagg    60900
cgggtgtatc acttgaggcc aggagttcga gactagcctg ggaacatga ggaaaccta    60960 tctctactaa aaatacaaac attatctggg cgtggtggtg gcgggcacct ctagtcccag   61020
ctacttggga ggctgaggca caagaatcgc ttgaacccag gagtcaggga ttgtagtaag   61080
ccgagattat gccactgcac ttcagcctgg acaatggagc aaaactctgt cccaagaaaa   61140 aaaaagaag cagtaaactc aataataatg aagtgccaaa ctcccaattt tgatttaaaa    61200
agtctcagtg tatatgtgta tatatatatt ttttcatgtt ttgccagcat ggagggatct   61260
attgttcgtc ttcctgaagt gattgccctc aagaagaaat acaaggcata cttgtatctg   61320
gatgaggctc acagcattgg cgccctgggc cccacaggcc ggggtgtggt ggagtacttt   61380
ggcctggatc ccgaggatgt ggatgttatg atgggaacgt tcacaaagag ttttggtgct   61440
tctggaggat atattggagg caagaaggta aacgagccat gagaatgagc gattagagat   61500
aaagtcactg gcaattagat ttggtacctc aggcctagca gatggggccc tgaactggga   61560
tgtccgcaaa tttgcctctg gtttaggctc ataataccag tgagtgactc taatgtctcc   61620
tcactgaact aaaggctggt tctgttcatt gtttgttgtt ttcttatttg agcttctttc   61680
taagctacat gctgatctga gatatagaat accctcttgt gtgaaagaac acacagtggt   61740
gctccctgcc cgccccagcc ttctgttggg tttgcattgt gctcacagtt tcaaaaacag   61800
```

```
tggggttgtc atgggagccc atgggaatag caggtcacct tgcccttgga cacaaatata   61860
tcatgagtga acatggagac aggaagcaaa aaagttgtgc cagctgtggg gtactacaaa   61920
gcattgtatt tttcaatttt taaactatga agttgccttt tctgggtctt tgtagtcaga   61980
aaaaaatcat acggtgaatt ttgatgcagg taagaatctg tggtgtggtc gaaatggtga   62040
accataaaga cagaggcctg ggtctgaata tttctcggct tactttgtta gacctcaggg   62100
aaaacattta acctcccagt ttccttgtca gtaaaatgga gataaatatg cccagcttgt   62160
aagattgtag taagggttta aaaagtaata tatgtccatg ctacaacgtg ggtgcacctt   62220
aaaaacatta tggtaagtga aaaaagtcac aaaaagtcac atattgcatg tttttaaaata  62280 tgtgatacct agaataagca tagaaacaga aagtagatta gtagttgccg gaggcggagg   62340
ggatagggaa atggaaagtg aatgctaatg ggtatgaggt ttcctttcag ggttatggaa   62400
atgttctaaa attagtggta aaagtggcac aactctggat atactaaaaa ccactgaatt   62460
gtgctttaaa acggtgaatt ctgtgtatgt ggcttatatc acaatgaagc tgttatttt    62520 aaacgttgat tgcaatgtta gggaaaaaat aatgtatgtc aggtatttgt atatggcaca   62580
gaggaggtgc tcataaatgt tcttaatttt gcttcaccac tcaatattcg gagtattaaa   62640
gaatggttat gctgggcaca gtagctcaca cctgtaatcc cagcactttg agaggctgaa   62700
gtgggaggat tacttgagcc caggagttca ataccagctg ggcaacatag tgagacttca   62760
tctctacaaa aaagtaaaaa aattagctgg gtgtggtggt ggcacatgcc tgtagtccca   62820
actatggggg aggctgagat gagaggattg cttgagcctg ggagatcaag gatgcagtga   62880
gccgtgatta caccactgca ttgcagcctg ggcaacagag caagacccta tcacagaaaa   62940
aaaggtcatt cttttaatac ttgattgcct gttagagaga actcattttc agtgactttt   63000
aatcagcttt gatagatttt tttttttttt ttttttgag accaagcctt actccattgc    63060
caggctggag ttcagtggca caatcttggc tcactgcaac ctccgcctcc tgggatcaag   63120
cgattctcct gcctcagcct cccaagtagc tgggactaca ggcacgtgcc accatgccca   63180 gctaatttt tgtattttta gtagagacag ggtttcaccg tgttggccag gatggtctcg    63240
atctcttgac ctcgtgatct gcccgcctcg gcctcccaaa gtactaggat tacaggtgtg   63300
agccactgca cctggccagg tttgatagat ttttatctca aatattacct ttttgttaat   63360
gggaccaggc tcactttgga gagttgtttt ttagtaagct ttgtggctgt gaaccaaagg    63420
atagaaaaat aatactctgg gagatcatta aagtacaata tatttgtgct tttggttttt    63480
ttagtacaat ttttaatatt tttgagataa aactgtttca tagccacatt tgtgtcccc    63540 taatttgttc tggtacataa gcttcttgtg tgtgcatttt aaagatttgg tgaaattaaa   63600
agatatcaga gaatagggat atacaattaa gttttttttga atccttgta aatgacagag    63660 ttttactttta ttcagtgaga tgtcattggc atttttaataa aataccttgt aagtttctat  63720
ttcacattta tatcatttta tacatttctg catatctgga ggaagttcta atgctcttaa   63780
agttgatgtt agagaactgt tatttagggg tagaaggatg ggctttatag gcacacagag   63840
ctgcagatga cattttctgt gatacttgga attaaatcat tatatctaaa aagcaatcca   63900
aacaccttgt ttaattcagc tgtgttcatt tattttttaac ttttttttttt tttttttttt   63960 taagacggag tctcactctg tcccccaggc tggagtgcaa tggcgcaatc tcagctcact   64020
gcaacctccg tctcctaggt tcaagcgatt ctcctgcctc agcctcccaa gtagctggga   64080
ttataggtgc ccgcctccac gcacagctga ttttgtatt tttagtagag atggggtttc      64140
accatgttgg tcaggccagt cttgaactcc tgacctcagt agatccaccc accttggcct   64200
```

```
cccaaactgc tgggattaca ggcatgagcc accatgcacg gccatatttc taactttaaa    64260
tgatacattc tccaaattta gagggggttgt tttaaaacta gtttttctct tatgttgttc    64320 catgttttaaa aaacaaaacc aaacctaaga actttgccat gtttctgacc cagttgttgc    64380
cagcggtatg cttcgaccat gttggttgac cttgtatctc agattagtgt ccctattcca    64440
gtgccattga agtgaggagt cctctagaac ttagaaggaa aggactgaca ttgccggtga    64500
atgcaagaat tgtctctact tatctgcctc tgtgaactcc ccaggagctg atagactacc    64560
tgcgaacaca ttctcatagt gcagtgtatg ccacgtcatt gtcacctcct gtagtggagc    64620
agatcatcac ctccatgaag tgcatcatgg ggcaggatgg caccagcctt ggtaagtctt    64680 tctttttcttg aaacattgca taagtccacc tagcagccaa acgtgctgtt tttcttgagc    64740
ttttttccta aaataaatag tcaggtttac taataggcag agctggctgg tgtgtggttt    64800
ccatggacac ttttttagtg tgtttgatac atatgccatg agaacgaccc tggctcactt    64860
tctatggaat tttcttgttt atagatggga ggctttactc ttactatcct acatacccctc    64920 ttaactcaga ggtaatatac cttcgaggtt tttcttgaat tacataattt tatgtgaagg    64980
tataattcac tgttagtgat gtttcattaa cagcatagtt aagagctgct gttttcataa    65040
attagtattc ctgatttaat gccttttttaa agagtttcta ctttcatata cggtagataa    65100
taaatgacat cctgaatcag tttatttttgt ctttgatggg atttgtagtc ccaactagat    65160
gccttgattt aaacatacta ctgtgaacag tgaagttcag tgttcacttt ctgacatttg    65220
acttttattc tgcaacacca gagggcagta ttgactgcag aacagtggta ctaaaagggg    65280
agcaactggg tgtctgtctt tactttaaaa aatatttttca ttgcatgtat gagacaataa    65340
tttcacttgt cgcttttttt ttttttttt ttttttgaga cggagtctca ctctgtcacc    65400
caggctggag tgcagtggtg tgatcttggc tcactgcaag ctctgcctcc cgggttcaca    65460
ccattctgcc tcagcctccc gagtagctgg gactacaggc gcccgccacc acgcccggct    65520 aattttttttg tatttttaat agagacggga tttcaccgca ttagccagga tggtctcgat    65580
ctcctgacct cgtgatccgc cctcctcggg ctcccaaagt gctgggatta caggcgtgag    65640
ccaccgtgcc cggcccagtt gttgcttttt taatgcttgt aaagtcagtt tggcatttgt    65700
aaaagatttc acattatcag ccatgagctc tccactctac agttatgtaa tactttattg    65760
taagattgat ttggcttgca tcgaataaag tggcacatct gattttggtt ggtttaagac    65820 tgttttctttt ctttctttttt ttttttttttct ggttttgtt tttgagacag agtcttgctc    65880
tgtctcccgg gctggagtgt agtggtgcga tctcagctca cagcaacctc cgcttcccag    65940
gttcacatga ttctcctgtt tcagcctccc aagtagctgg gaccacagga gtctgccacc    66000
acacctggcc atttttttttg tatttttttgt agagatgggg tttcaccatg ttgcccaggt    66060
tggtcttgaa ccctgggct caagcagtct gcctgccttg gccttccaac gtgctggaat    66120
tacagctgtg agccaccaca cccagctgac tgttttcttt tcttttcttt tccttttcctt    66180 ttctttcttt tgagatggag ttttgctctt gttgctcagg ctggagtgca atggcatgat    66240
cttggctcac cacaatctct gcctcccagg ttcaagcgat tctcctgcct cagccttccc    66300
gagtagctgg gattacaggc atgcgccacc acacccggct aattttgtat gtttagtaga    66360
gaccgggttt ctccgtgttg gtcaggctgg tctcgaactc ccgacctcag gtgacctgcc    66420
tgccttgact tccaaaaatg ctgggattac aggcgtaagc caccgcgccc agtcgactgt    66480
tttcttaaat cagaatttta ccttaacatt ttttctgatc tgtgctagat ccttgttatc    66540
```

```
tctaatgaga gattttttgga aatagtgaaa tgtgatcatt ttcagttttg tgaattaatt   66600
ccttgaagaa gttgttttat taatgttgca aacacatagt ggagcctgtg aatagctccc   66660
tgttaataac agctatatct cctctccttc tgatgtggtg ttagtggaaa ctgtgtgtga   66720
atctgagaga cagacatata tacacacata tatatacata cagctagcat ttctctaggt   66780
acttcacata ggcacactta ccttactgat tcagcacaca ggtttaggtg actaagaaat   66840
ggctaagagc tatcaaagtt aacattggat aatttatttg ccctgttcca gaacatggat   66900
ctgtgtgaca cattaccccc agataaatga cttatctgta ctaaatgatg aaatctgggc   66960
tgtgctagta gtgagaaaat gaaacatggt aattatatat aggctttgga tcagcacaag   67020
ttttctagtt tttgcctcta gccaccccca aagcttagtg atgtgacaca acagccatct   67080
gattatgctc acagatgcca caggtcaaga attcggtcag ggcacagcag ggatgacttg   67140
tctttgctct gttgtctggg gctggcctgg aagactcaag tgtctggaaa gactgagatg   67200
gttggtggtt gggatcatct ggaagctttt ccactcacat gtcacctggg ctggagtgac   67260
ttggagccag gctcagctga ggctgttgac cagagcacct tcatgcatgt atctttttcaa  67320 tgtggcttag gctcctcatg acatcgtgac tgtgtaccca gaaaggatgc ttcagagagc   67380
aagcattcca aagaacctgg cggaaacccc atgaccttt ctgacctgtt gttaacaagc    67440
aggtcactaa ggccatcccg gattgaaggg gtggggaact agattccacc tccccagtgg   67500
aggcatgtca aagaatttgt ggctggtttt ttttttttg agatgcagtc tcaaggagaa    67560
gtaccatgct ttttttaaaca accagatctt gggagaactc agagcgagaa ctcactcatt  67620
acccaaggat ggcagcaagc cattcacgag gatcctcccc atgatccaca cacctcccac   67680
caggccctac ctccgtcatt ggggatcaca ttccatcctg agatggacaa acatccaaac   67740
catgtcagtg aatatattac atttatcatt aaaactttgt tattgttgga ttccagtaa    67800 cattaagtac ctggtattga aagtaaggct taaacatgta tatgtggttg cttattgtta   67860
aatgttttca tcttttttgtg tgaagaaatg ttgctctttg gtgagagtac agagccttca   67920
gaaaagctgc agcatgtaag ggaaggtgag atccagtttc cacacgactt tgtgagcgct   67980 cctttccccct tcctcccaac ttttttccgca ttttcccctcc agtttctatc cttttcccaa  68040
ggaagaacag gacatatgac taggttgaca gatcttgaaa ggcaacttca ctaggatctc   68100
aggtgagata ataatgaatg ggaattgtgc tgccaggatg cctgtacctg gagtgggaat   68160
actgagcaca ggccagggag tagaaaaaat gaggcctagg aaattctgtt aaattccact   68220
agacatttga aattctaact tttacttttac acatcactaa tccgtgtcca ctaatggaaa   68280
tttagctgta gtatctacat acgaatcaag gcaaagtgtt tgaccaaatc aactaaaatt   68340
ttgcttttcc attttccaga gctgtgcttt gatgtatttt atttctgtcc aaaggtgtag   68400
ttaataataa catgcatagc acccagctta gtgtgtgaca tctaggatcc tttcagtaaa   68460
tttattgaat gactgaatga atgcacgcat gattggcaat accagaaaat cagtgggttc   68520
ttcaagtact ttattgtaac attgcttgaa tagttgaatg ttaagccaga atgaccaaat   68580
tatggaacca aattaactag ataggtacat tttaatagat acattttttaa ataatgtcag   68640 aacgctttat agagttttgt acttctttgt tttgaaagga actgggtcct tgcaggcagc   68700
tactgatgta ggagaaaaaa gactaccctg agcagattga ggtttaatta aaactaggtt   68760
tggctcattt gaattaattc cagtaataga cttgttaatt aggtgttaaa tgatcacctt   68820
gagaataccg gggaactgtc aaaaactaag agaactgaga cacttaaaaa aaaaaaaaa    68880 aaaaaaaaaa aagacattcc aggacaatgc agtggcacat gcctggagtc ccagctactc   68940
```

```
aggaggctga ggcacgagga tcgcttgagc ccaagagtcc tgggctgtag cacactgtgc   69000
cagagacgtg tctgcaccaa gttcagccat cagtatgatg acctcccaga agtaggggac   69060
caccaggttg cctaaggagg ggtgaattgg cccaggttgg aaacgaacag gttaaaactt   69120
cccctgctga tcagtagtgg gattacgcct gtgaatagcc actgcactcc agcctgggca   69180
acatagcgag accttgtctc tttaaaacaa aacaaaacaa aaaacattc caagattccc    69240 atgcagaagg gttagaagtg ttgaaaaaac acagccttgc tgggaggggg tcataaagag   69300
agactttcct gcctgtcttc agggctgaca gcttttaacc ctcccgtcaa gcaccatact   69360
tcctgagccc aagaacgttt gggtgttgac tttcttcttt gttgtgcttt aaagtaattt   69420
atttcactat tagaaattca tcgaaataaa aattaagttt tctggtaagc acagttttgt   69480
tcttacccac agtagagttt agcagtttat ctgatgctgg gaatcagact cgcttcctcc   69540
tgttttgtga ctttctgcct agaatgctgt tgtttggaaa aaaaaaaaa aatacttgtt    69600 tccgccgggt gcgatggctc acacctgtaa tcccagcact tgggaggcc gaggcaggcg    69660 gatcacctga ggtcgggaat tcaagaccag tctgaccaac atggagaaac cctgtctcta   69720
ataaaaatat gaaaattagc tgggtgtggt ggcgcatgcc tgtaatccca gcactttggg   69780
aggccaaggc aggcggatca cctgaggtcg ggaattcaag actagcctga ccaacatgga   69840
gaagccctgt ctctaataaa aatacgaaaa ttagctgggc gtggtggcgc atgcctgtaa   69900
tctcagctac ttgggaggct gaggcaggag aattgcttga acacaggagg ttgcggtgag   69960
ctgagatcgc gccattacac tccaacctgg gcaacaagag cgaaactcca tctccaaaaa   70020
aaaaaagtgt tttaccattt gttaaacact tatcaagcaa caagcaacta ctctctacat   70080
agtggtagat atgctgtgtg ggagatgcag agttgaacaa taggtgatct ttgcctttga   70140
aaaaacagtc cagtggtagg ggtaagattc ccgggaagaa ctagtctcag aggcacagat   70200
aaattcttcc tttgttcagc ttgtcttttc tcaatttcct cctccattct cttctacaac   70260
ctcctccttc actcactccc actcccctaa aaccttaaac ttccttaaac cagctaagtt   70320
tttgaagcaa actcatattt tagatttctt atataataac tttctatata atgaaatttt   70380
ttctgtggat actgtcactc tagtaaatta tcagcaatca aagcagcttc ttgattattt   70440
tttaaagcag cttcttgatt attgagcaca aaaggccttt taaccaatgg cttaagcctt   70500
ctgaaatcag caagcaatat gaccaccttt caggtggaga aatttgagct catgtatgga   70560
acaagttttc tcaatatctt gtctccaact agaatgtagc ttttctaact ccatctgctt   70620
ctacttctga ggttgcatga tgatagttag cattttatta aaacagacta ttttataatc   70680
tgtttctaat tttctgctaa ttttccaaag tttaattgtg agtaatcagc ccaacaaatg   70740
aaagctcttt tgggcatttg cctccctgtt ttctctccat ggatcagtag ccctttcccc   70800 accttttctgc ttcagaaatg gattctgaat actcaagagc ttttgcaaca tggtgtgtct   70860
attttttatt ccactgctat cttttttcttc caaatccaaa tgctattaaa agtttcttgc   70920
aacaagaaca ttctctcctt ttgtgcctcg tttcagagtt agtttgaagc tagcaattag   70980
gatgcccagt gtctattgtt tgttgaagaa taattctaac tttctaaacc ttcacataat   71040
tggaattgct tttctccccc cagaattatg tctgagggct ttattttttca tcaaatagac   71100 ttgatcctag ctgttcccca actttatagc agatacttaa tatgtataaa ccagtgacct   71160
gatagatgga atctgctcaa agtaagaacc tgatacccgg ccgggcacga tggctcacgc   71220
ctgtaatccc agcactttgg gaagctgagg cgggtggatc acctgaggtc aggagtttga   71280
```

```
gaccagcctg accaacatgg cgaaaccctg tctctactga aatacaaaaa aatttagcca    71340
ggcatggtgg cgcatgcctg caatcccagc tacttgggag gctgatggag gagaatggct    71400
tgaacctggg aggtggagat tgcagggagc cgagatcacg ccattgcact gcagcctggg    71460
agacaagagt gaaactccca tctcaaaaaa aaaaaagtg cccgataccc tactaagagc    71520
ttgccggatt tgaaagcttt ccaaaaagga attgattttt ttttaattgt cacctatagt    71580
ttttctaatt atctaaatat tttatttgta tctacctccc tgctatctac tttggcagta    71640
gagtgaggtg ttaaagaaaa aattattcct gtcacttgtg aaacatgata agacagactt    71700
ccttcaaggg ggccatggta ataagcatag ggatgactgc aatggggtct tccagtgggg    71760
gagagagggt gggctgcagt ctgactccaa taaggacaga tgaggattta cagccaagga    71820
acagggtggg agtgagtaga tagaaaaata ctaagaggaa acatcagggg taagggggat    71880
gcttgccttc agcattcttg ttgaaggtag gccagggtga taagatacca ggggtagtca    71940
tgtaggggat tttctctaat ctgacttagc aggattattg ctcaaactgg attctgcaag    72000
aatggagaag gaggcgcaac gtcaggactt tatcagaaag gactccaaga ggagcctgac    72060
tcaagtttgg tcaaggagag gagtctttgt caggttcaga atgacctcat taacatgaac    72120
tctttaagcc cctgttctca gactttgtcc atggaccacc tgcatcagag gtactttag    72180 tacagtggtt catccttgc ttacacacag gaaagcttaa aaaaatagtg ccagtgttag    72240
agaccttctg tagacccatt gagtatctca aggcgaggcc tccctgccat ggcatggtgt    72300
tatttaaaag caccccagat gcttctcatg taaggcccca tttcagaacc actgctgctt    72360
gttaaaaatg aagattctag tttgttccac ccaccctact gagtcttggt ggatgaggcc    72420
ctagaatatg cattgaaaag aaaaccttag gctggatatg gtaatcctga cattttggga    72480
tgtaatcgta acattttggg aggctgaagc tggaggatca cttgaggtca ggagtttgag    72540
accagtctgg gtgacatagt gtgagcctct gtctctacaa aaaattctaa aaattagcca    72600
agtgtggtgg tacacgtctg taatcctagc tacttgggag gccaaggcgg aggattgcac    72660
aaacccagct atgatcacac cactgcattc cagcttggat gagagaggga aaccctatct    72720
ctagaaaata aaaagagga ttgtcttttt gacaatcctc tttttttcct tttaactttt    72780
ttacctcagt accaaagcag ctctactgat tgatggtaat tgaaaaagga aaagaaactg    72840
gaagtcaaga tacaaatgag ggagatgttt ggcttgtaag acaggcattt gctggcagag    72900
ctaagttgcc attttggtt gtttctggaa ctctaaatgc ctgggatgct gacactccct    72960
tctgaacagc tgatgattct ggctgattga atcagtggca taggtggaga agttagaaac    73020
cagttaggtg cagcaggaaa acagaactaa gcattcagag atctgtggtc atggttccta    73080
aggctagttg gaattaatta ttttttgtttt acttttttg gggggggctg cttgtatttt    73140
tataacctat taatcctcaa attacttagt acataaccta caaatggcct tgcccactat    73200
aaagttgtta aaatgtttag tattaaccgt tttgtaaaac tctgattgtc ttattgtatt    73260
gccttctacc tctaaaactg ttaacttaaa tccaagccaa gcctttacca gagattacct    73320
ttatttgcta gctgtcttca tctgtgggta gatacattac tacagtgttt acgttcctta    73380
tctctttgtc tcagagtagc ctgtgatatg ttccagcccc aacagaggac agtagaatgg    73440
tccattaaga ctttctgagg ccaaggtggg cggatcactc gagatcaaga gttggagacc    73500
agcctggcca acatagtagt gaaaccgtgt ctctactaaa aatacaaaaa ttagccgggt    73560
gtggtggtgc acgcctgtag tcccagctac tcaggcggct gaggcaggaa aatcactgga    73620
acccgggagg tggaggttgc agtgagctga gatcgtgcca ctgcactcca gctcaggcaa    73680
```

```
cagagtgaga cttggtctca aaaacaaaca aacaaaagac tttctgtcct gcctgtgggt    73740
tggcacccgt taaaactcag ttccttgatt tttcacaggc acttggcctc ttttctgcct    73800
tttgtggagg gccctctgtt tctggctgtg cattagcaac cattcttta  aacttctgat    73860 tatattgaat cagcaacttt aagcttgccc ctgctgcttg tcatacatcc tgtggcagtc    73920
ctcaggaaat cctagttttt ggcattgaaa tgaattaaag gattaagcca caagagggtg    73980
ggggtgataa actgtgcttt taagaggaat ttactgtgca gtacttggtg ttagcaaaag    74040
cagttctagt tcttacaggg atataggaaa ccaaggggct gctttagaac agcatcccta    74100
ggatatgaag acgcagatct gtctgctttg atgttcttta gcttgacagt ggccccggct    74160
gagcactttg atatttgtcg ccagtctagc aaaatagggg ttgtgtcttg gagatggtaa    74220
acctagttcc cgttgctttg cttcagtgtt agaaaattac tgaactcttg cttcctggaa    74280
gtcccttata aatctccctt ttacaagact gttctctggg gcacgaaaat gcctttgctt    74340
ataaagagcc tgttgaaggt ccatttattt tccttttctt aacagaaaga ttttccagtg    74400
ccatttagtt aggacttacg ggaaacatgt tgttaaaatc aatctgtcct gttagctaat    74460 atttcttta  ttttcatttt gagcttttag ataagattct ttatctttct gtgagataat    74520
gtgaaaaaaa acacaaaaga aataaattca ataccagta  tactctggtt tttaaaaata    74580
tcttcactga cttttttttt ctttacatgc tctactctcc ctctcaccct acttccttct    74640
tcacttttca cttggtactt tcagatattc tttgtgggtt tttcttggtt tttttttttt    74700
tttccggaca cagagtctgt ctcactctgt gcccaggct  ggagtgcagt ggcacaatct    74760
tggctcactg caacctccgc ttcccaggtt caaaccattc tcatgcctca gcctcctgag    74820
tagctgggac tacaggcgcg tgccactatg cctggctact cttgtatttt ttagtagaga    74880
cggggtttct ccatgttggc caggctggtg tggaactcct gacctcaggt gatccacccg    74940
ccttggcctc ccaaagcact gggattacag tcttgagcca ctgcacctgg cctagatatt    75000
cttagatata ttcatgatgc atcccatcta gatgcttgtg atgagtatat aatttactga    75060
tctggaaagt gtgacaagag tttaaagtgt tatctgctgc cttctccccc cactttagag    75120
ctgttcaaag aaagtgacca ttgatcattt taaaagatga gcaaggaaa  gactgcttct    75180 tttttaaaaa agaaaatttg atgacctact gttagaacac atttccacat ggaccccccg    75240
cttctaaatg ggtgtatatc cagatcatcc agtctgtgtg cacagagtcc ttgcatttct    75300
aagttcaaaa tagtaattta aatgaaagta ggccatcata aggcattgct aggaagaggt    75360
tactcttgat agatgaatgt gctgcttttg gtaagaatta gtttgttatt tatatttaaa    75420
ttttgtaggc cgggcctggt ggcttaaacc tgtaatccta ccattttggg aggccaagac    75480
gggtggatca cttgagccca ggagttcaag accagcttgg gcaacatggt gaaaccctgt    75540
ctctacaaaa aaataaaata aaatacaaaa attcccagg  catggtggct tatgcctata    75600
gtcccagcta cttgaggtgc tgagacagga ggatcacttg agcctggcag gcggagattg    75660
cagtgagctg agatcacacc actccagcct gggtgacaga gtgagtccct gactcaaaat    75720
aaataaataa ataaataaat aaataaataa aatgttttgc aagcatacct tctgagtaca    75780
gttacacttt gccttattct tagattttac atgttacaca tattttggt  tctgtgaaca    75840 gattatatat ggcatatttg tagttctaaa ctacttctgc aactaaacat gcattatatc    75900
actcatttcc cctcagtgga actggtatat atggacttat gccataatta aatgttagca    75960
atgagagaga tctaccttta aaataataaa atgtgctggg tgcggtggct cacgcctgta    76020
```

```
atcccagcac tttgggagtc taaggtgggt gatcgcttga ggtcaggagt tcgagaccag    76080
cctggacaac atagcgaaac cccatctcta ctaaaaatac aaaaattagc caggtgtggt    76140
ggcggccgtc tgtagtccca gctactcggg aggctgaggc aagagaatca cttgaaccca    76200
ggaagcagag gttgcagtaa gccaagatca caccactgca ctccagcctg gcaactgag    76260 caagactccg tctcaaaaaa tttaaaaaat taaaaaataa aagtaaaaat aaataaaatg    76320
catttcaaaa tcaaatggag accatttctt gatgatctgg gctgctgtgc cttcctcttc    76380
ctgcatatgc acagctaatt gagaatgtgg tgttaaattt attagcagat aagaactctg    76440
tccattacat ttttttttgta tgtttcaggc cttttaaggc atattattcc tttattgctg    76500
tctgatcttc aaaacatatc cagaggacct tcttattact tttttttttt tttttttttt    76560
tgagacaaga gtttcgctct tgttgcccat gctggcaggc tggagtacaa tggcacaacc    76620
tctgcttacc gcaacctccg cctcccaggt tcgagcgatt ctcctgcctc agcttcccga    76680
gtagctggga ttataggcat gtgtcaccac acctggctca ttttgtattt ttagtagaga    76740
cagggtttct tcatgttggt caggctggtc tagaactccc gaccccaggt gatctgcctg    76800
cctcggcctc ccaaagtgct gggattatag gcatgagcca ccttgcctgg cttaattgtg    76860 ttttttttatt agttcaagcc acaataagaa gtttattcag tcagcaatct gttttttgact    76920 acttaaccac gtgccagcta caaaaaaata acatatagct tcaaaagcct cttaagcggc    76980
tgggcacagt ggctcacgcc tgtaatgcca gcactttgga aggccaagac tggcagatca    77040
cttgaggtta ggagtttgag accagcctgg ccaacatgac aaaacccccat ctctattaaa    77100 aatataaaaa ttagccagac ttggtggcag gcacctgtaa tcccagctac ttgagaggct    77160
gtggcaggag gatcacttga gcccaggagc cagaggttgc aatgaaccga gatcacacca    77220
ctgtactcca ggctgggcga cacaacgaga ccccatctcc aaaaaaaaa aaaaaaaaa    77280 aaagcctctt aagataaaat tttcattttt ttgaattctc agaataaaca acagtttctt    77340
agtgttagat tacaattatt tcttaatacc acttagatcc ttcttttttt aattaatttt    77400 ttctctttt ggtgtctgag tgggccttag agttagaaaa taactgtctc ctgttggctt    77460
gccttttctc ttttttcctca aggtcttttaa tatctcccta gaagataaaa aggatatatg    77520
cccatttgtt tctgtttttt cccaatttga tgatagaaga ataggcctta aaatattata    77580
ggtcttgtta taggtaaaat aacaaaaata gaaaataata taaatgatct tacatatgta    77640
aatataaaat aagtttttaa agaccgtttg tttaagcatt tcattaagtg ctttaatgga    77700
gtatcccatt ttcttaaaac agccttatct agtaggtagt tatcatcatc atcatcatcc    77760
ccattgccat tcccattttg cagatgaaga aaccaaactc agaggttaag tgacttggct    77820
gtagccatac agctactaga tgctcaagcc aggatacaaa cgtagatagt ctgacttcag    77880
aagtttatat accacaggct ggggatagtg gctcatgcct gcaatcccag cactttggga    77940
ggctgaggca ggtggatcac ctgaggtcag gagtttgaga ccagcctgag caacatggcg    78000
aaaccccatc tctactaaaa atacaaaaat tagccagatg tggtgacgca tgcctgtaat    78060
cccagctact tgggaggctg aggcacaaga atagtttgaa cccgggaggc agaggtagca    78120
ttgagccaag atcaagccac tgcactccag cctgggcaac agagcaagac tctgtctcaa    78180 aaaaaagtt tatatagaac caaattaaaa ctactaataa gtgaaattca ggaagatggt    78240
gaaattatta gttctctctt tctttctgag acctgcatta ctgctttgat gtatgacatc    78300
caaaatgact gtcttattat ttcaagttta aaatgtcctc catgcaagca tatctctgtg    78360
cctattctag attattagat gtgagaataa aattagctca ggtagagaca ggatcccatc    78420
```

```
cccattatga tggggtgtgc atgagtggta gttttcagaa aaggacggtg tctgcttgcc   78480
atcttgaaca ctcagatttg caaaggtaat ttgcctcacc tggatgataa ttactgggtg   78540
atgtgatggt agaggtactc taaattggag aataaaggaa aacctcaaaa gctttggaaa   78600
gttcatagca tcgtagaggg taaaatatat gaagcttgtt tataaactat aaatcagagc   78660
attagagaat gaagtgatta tatgttagta aaatcagctg tgtccttgtg ttatgtgtta   78720
aaattaataa gagtgtgcac aggaaataga aaatggagaa ttggaaacaa caagggaagt   78780
aagatagtcg ttcatttcat ttttcaaagt taaggctaag ccgaagggtc ggaacatgtt   78840
gtatggaaga taggaacagc atgattttaa gagaagaata catgaacaag tgaaataaca   78900
gtggccgttt attgtctgct taccatgtag ttagcactgt tctaactgct tttcattaaa   78960
ttctcagaac aagtattaaa tgttagacat tattttccct cttttacaaa agggggaagc   79020
tgagaggtta aggaaacaaa gaggttaagt tgcttaccca aggacacata gttactagtg   79080
ttggagccag tttgaactca tggatccagt tccagaatgc tttttgtgta ctagatattt   79140
attaatgtat tagatgattg tttgccttaa tgtaattgac tatataggta attttgcttt   79200
gtaatttaaa ttagttcgaa tacataacgt gttttcattt tcccagcgta tttcaacttg   79260
gcttatctgc tcagtgttct tgggggagtt actagggaaa aaaatataac agtatttgtc   79320
ctcagagttt gcagtttgtt ctggcaacac gagaccacac ataaacggca taagtacagt   79380
aacaggaact tataaacaag agcaaattaa tgaattacaa agtagagaca tgtcttaaaa   79440
tgtgccatag ggaatctttc cataactttt tttttttttt aacttctgcc ctttatcttt   79500
catagtgttc tttggtttct tggggttttt taaagataag aagtacatag gccaggtgca   79560
gtggctcacg tctgtaatcc tagcactttg tgaggcagag gcgggtagat cacgaggtca   79620
ggagttcatc agccttgcca agatggtgaa accccatctc tactaaaatt ccaaaaatta   79680
gctgggtgtg gtggcaggtg cctgtagtcc cagctattca ggaggctgag gcaggagaat   79740
tgcttgaacc tgggaggcgg aggttgcagt aagccaagat tgcaccattg cactccagtc   79800
tgggcaacag agcgagactt catctcaaaa aaagaagtgg gggggtgggg gaatacatag   79860
acattggtag aaaataacaa aaacaaaatt aaaatttaca aattgcttgt atttactgat   79920
ttgcatgatt ttcacctaaa ctgcagaaaa ttgtccatag gagttttttac tagtagtatt   79980 ttatctttac cactgatcta atggtagaaa aagaaataga gctctaagag aggtttttttt   80040 ttcttctttt taaaagttat cacttgtctt ttgtttacat agaaaagtgt ggctttggaa   80100
taaattatat tacttgaccc acctcccaca aaagttttgc ttaaactcgg cctataggct   80160
ggaaggacta ggatgaaaag gggtattgct aatggatact ggtttctttt tgagtgatga   80220
aaatattcta acatttattg tcataagagg tgcagaactc tatactaaaa aacatttaac   80280
tgtgtgcttt aaatgggtga atttttatggc acgtgatata tatctcaata aagctgttta   80340
aaaaatcacc tggtgacgtg aatccattgg tcaaaaataa aataaagaga aaaaaaaaac   80400
caaaaaatac ctgacctaca gtgagcaaac agtgtcacct ataataaatt taaaactttt   80460
ttattgtggt aaatatatat aacaaaatta atcatttttc ggtacaattc agtggcatta   80520
catacatcca gtgctgtgca accatcacca ctatccattt atagaaacctt tcatcatct   80580 cagaaaataa ttttttaatat tctagttcaa gtttggaagc agtagtcttg acctactgca   80640
tttcaaaatc taggctctag aaatacttgc tccaccaaaa ttgagttgtg tctccacagt   80700
ttttagcctt tttgctggtt tcccctcaaa ccaacttttt cttttgtgtt tcctatctca   80760
```

```
ggtaatggca tcactattca tgaagttgtc caaacaagaa atacctatca tcgtttctct   80820
cctttatccc ctgtatttag tcaccagtgc ctatggatca tgcttcctta atatctttga   80880
acctgtctac ttctccatat ctcattgtta tttacttgac ttagatttct gtccactttc   80940
acctggtttt aatagccagc cagtcataat agtagaggaa tcagtcaagc aaaaatgctt   81000
tggaagaatt aaataagcaa tgctgaacat caggaattgt agatatccgt acagagagtt   81060
ccagtaaaat tttatgagtc cacgacccct tttctaagca gtctggtcca tgttggtctc   81120
atacctcata tgcaggattc attcattcat taaatatttg tttcatacct tgtttgtaac   81180
acttctgtct gccttctaaa tgtatcctca gtccactttc taccacttgc tactgtgttc   81240
atccaagtca ccatcttccc tcctgtggtg tctctgcttc cctctttgca tctattctaa   81300
atatagatag ctctcagtgt gatcctgatg ggagatcata tctatcttct gtttaagaac   81360
cctccccaaa ggccttctca tcccgcctaa agtcagtgaa gacctgtggg cccttgggat   81420
ctatctgtct gttgacttcc tctatcccac tcttcccctc actcgctgtt ccatatttct   81480
tgcatatgct gggtgtgctt tttgctccgg gtcttggcag tttatagaaa tagcacttgg   81540
ggctgggtgt ggtggctcac agctgtaatc ctagcacttt ggaaggccga ggcgggcaga   81600
tcacctaaga ttgggagttc gagaccagcc tgaccaacat ggagaaaccc tgtctctact   81660
gaaaatacaa gattagccag gtgtggtggc gcatgcctgt aatcccagct actcgggagg   81720
ctgaggcagg agaatcgctt gaacccggga ggcggagggt tgcagtgagc caagatggcg   81780
ccattgcact ccgcctgggc aacaagagcg aaactccatc tcaaaaaaaa aagaaatag    81840
cacttggctg catcaggtct ttcctgaaac acttctttag tgagtattaa ttttgtttgt   81900
tgtccatctc ccacactgga atgtaagctg cataaaggca ggagttttgt ctgtttcatt   81960
tgctgcagaa tgtccagggt ctagagcaat atctggtgca tcatgagtgc tcagcatatg   82020
tttttttaat gacatctgct tccctagtgc acaatatgtt ctccccttt tgtgtagtct    82080
tcttttttgcc tttggtgaaa tcaattttt tttattttgc ctttggtgaa atcaatttct   82140
atttcttcta tgtttagcat atgtgtgtgt gtgtgtgtac tgaaatatgt gaaatgttta   82200
ttatttaatt ttatatacca gatttctgtg ttaaaaattt tttatatcat aaagttagac   82260
tgccctgagg cttcagaaat gttagtagcc tcctaatttg acttctttag tgtttaagtt   82320
tctttcagaa atcctgaaac atatccacaa ccgctgtatg tatacagttt cttttaacac   82380
ttatttggtg aatttatcaa tatgaatttg tcatgtttct caaaatgagc acttttaaaa   82440
aattggtaat attgaatttg atgaaaccta ttatttatat ggagtaaata atatgaagtg   82500
gaacaaattt acatgttccc tttgagactt tttatagata tgcatttgtg tgtgtgtgtg   82560
tgtgtgtgtg tgtgtgtgtg tgtgtgtgag agagagagag aaagagagag agacagggtc   82620
tcattctgtt gtccaggctg tagtgcggcg gcatgctctc agctcactgc aacctctacc   82680
acccaggctc aagcagtcct cccacctcag cctcccaagt agttgggacc acaggcgtgc   82740
gtcaccacac ctggtaattt ttgtattttt tgtaaagacg gggttttgcc atgttgccca   82800
ggctggtctt gaactcctga gctcaaggga tcctcccgcc tcggcctccc aagagtgctg   82860
ggattacagg catgagccac tgcgcccagc ccatatttat tctaaaagaa agaagtagag   82920
gttataacag gaattcaaaa ttcagttggc accagcaaac cccagagact taggaatatt   82980
ttttgttact tttgctatcg aatctaaacg ttcatttgcc caacctactt cccctttctt   83040
gaaagaagta aaaattactt ttggaaattt cctgaataaa tggagtcagg aatcccagca   83100
gttcttactg ttaaaggacg tgcttgcaca cgtaaagaag ggtctgttta cctaaggttt   83160
```

```
atttagctct ggaacatcgt aagccctggt acaagtccag ccttcccgaa actaactgct    83220
tgcgtgtaca ctccctgctc agcttcgccc cttttaaaat gaagtcaaaa cattctaatt    83280
tggtaaaggt gttaggtcct gagaaattat tactttgtca atattaccgt atttgctttt    83340
cagaatttca gattccagtc atcctagaga gcatattatt tctacaaaaa ctgttttagg    83400
aggactttgt tatacattgc tattatactc acccagagac agttacttttt tttttttttt    83460 tttttttgcaa cggagtttcg ctcttgtcac ccatgctaga gtgcaatggc acagtcttgg    83520
ctcactgcaa cctctgcctc ctgggttcaa gcaattcttc tgactcagcc tcccaagtag    83580
ctggaactcc aggcgtgcac caccacgccc agctaatttt tgtatttttt tagtagagac    83640
agggtttcac catgttggtc aagctggtct caaactccga accgcaggtg atctgcccac    83700
cttggcctcc caaagtgctg ggattacagg cgtgagccac tgtgcccagc tgacatttaa    83760
attttttaat ctgaaactga ccttttctgt taacatgaag catttgttca tgctttgcta    83820
ctatggtggt gtcattttaa cttttttcttt gctgaataat tttgtactcc attgtatcct    83880
cataatttca attgtagtgt cccatagccc tccaaaaaaa gcagtcagaa tcagattttt    83940
tattttattt atttatttat ttttattttt attttattt tttgagacag agtcttgctc    84000
tgttgcccag gctggagtgc agtggcacta tctcggctca ctgcaagctc cgcctcctgg    84060
gttcacacca ttctcctgcc tcagcctccc gagtagctgg gactcaggc gcctgccacc    84120 acacccagct aattttttgt atttttagca gagatgggct ttcactgtgt tagccaggat    84180
ggtctccatc tcctgacctc gtgatccacc tgcctcggcc tcccaaagtg ctgggtttac    84240
aggtgtgagc caccgcgccc agcccagaat cagatttta tattaagtta ctaatttttt    84300
gtgccagccg tccatcagcc tccccatctt ggcagggtat gcagaagaaa aacctaatag    84360
taaaatatct agggaaaatg tcttcatgag aattaaagca aatgcacaga taaaaaacga    84420 atattttttat taccaggatt ttctattctg tgtattcatt cacgtgagca tttaaagaga    84480
gaaagggaaa gaagggaagg ccagctttca tttcttgcct caggacattt aagtttgaag    84540
tgctgttttc ctaacactta ccccatctta caatacaaat tcccggaata tgcagcacca    84600
aaaatttcag tattttttcca gatttgtctt aaaaccaaag gttaagagga gagttcctga    84660
gcccacacct gtaatattta gatggttctg ttttgttgtt gttgttgttt ttaagtaaaa    84720
ggggtattat taaataatag ttggctgtat ttaaaatcat caatagagag atgagaaatt    84780
taacctcaat tccatttttg tttaactttg ggtgattttc caagtatttt aaattttatt    84840
tttattctta ttgaagtatt gacattcata caatgaagtg tacagatctt agacatacag    84900
ttttcataaa tatactcatc taatcaccac ccagattgca gtataaaaca ttccaggctg    84960
ggtgcagtgg ctcacgcctg taatcccagc actttgggag gccaaggcca gcagatcacc    85020
tgaggttggg agttcaagac cagcctgacc aacatggaga accctgtct ctactaaaaa    85080 tacaaaatta gccgggcatg gtggcacttg ccttaatccc agctactcag gaggctgagg    85140
gaggagaatc gtttaaacct gggaggtgga ggttgcggtg accgagatt gtgccattgc    85200 actccagcct gggcaacaaa agcaaaactc catcacaaaa aagaagaaga agaagaagag    85260
gaggaggagg aggaggagga ggaggggag ggggaggagg aggaggagga ggagaaggag    85320
gagaagaaga agaagaagaa gaagaaagtc atggtccctg tgaagaaata actttcaggg    85380
cttatggtag agaacagtca accaggaaga gtaccatctt cctgaaagc atatggaata    85440 gtctagaggt attttttggtc acagactagg ttgctgtggc actgttggca tgcacagccc    85500
```

```
agaggccagt gatgctcaat gttgtgcaag gcactaaaca gcctaaacaa tgaagaactg    85560
ttttgcccaa aatgccaaca acaatcttac tgagaaactc tggaaatggt tgactgaaat    85620
tttgcagggt gccctctttg aagatgcag gatggcagaa atcctagatt aaaatgggaa     85680
aggagaatgc aggatggaag gaaatctgtg ggcaccacct ctttccctgg gattctgcat    85740
gatgtagtag actgaaggag aagcagtgtg atgtggcgga ggcggtgtta gggaagaatt    85800
cacagtaggt agatgagtct caacagggtg ggccaacgtg cattgttgat tatttgtaat    85860
gcaacaaagt tactcactta ttcctcttct aaattcctac gttaaatact taacattccc    85920
ttttagtcaa tcctagcaat acaggagcta gaatacatca ttgagtcatt caaagtccag    85980
tctttgaaac cagaagaacc agggagtcaa gtcttggttt ctctatttta agatatgtaa    86040
cctcactggg catcagttta gtttcttagc tgtaacataa ctcttaaata tgccttgctt    86100
ctaaagggga gaggtgggaa agcctactaa gtctgttctt cctctcagaa gttacttata    86160
tggtgtattg aaagatcttg tggtttaggc ctggtggatc acttgaggtc aggagtttga    86220
gacgagcctg gccaacgtgg tgaaaccctg tctctactaa aaatacaaaa attagctaag    86280
tctggtggcg ggcacctgta atcccagcta ctcaggaggc tgaggcacga gaatcgcttg    86340
aacctaggag gtggaggttg tagtgagctg agatcgtgcc gctgcactcc agcctgggca    86400
acagagcaag actccatctc aaaataaata aataaatatt tttttttttt aaaaagatc     86460 ctgtggttta aatgttgagc atgatggaaa tttgaaatgt tttaaccca ggtttgctta     86520 tcttttttg aaagcattac ctgatttcat ctgagatttt ctactatgca cactatttgg     86580
agttcttgga aatgatgtaa taacaatagt cactcctatc tcctcctcca cataagtcca    86640
agataccttc agctgagatg agattaagct gttgttctaa catgtggagt tagctgtagc    86700
accataaatg caagagaatt cttaatttaa attaatataa atcaacatat tctttcattt    86760
gtttatgata gactataaag tactgtctta tcaggagata aggcaggcta gcagttgact    86820
tggtaatatt tagagatgta gtaaccaaag caaaatgtaa tattcccctg cttagaaatt    86880
gctttactgg gccaggcagg tggatcacat tagcccagga gtttgagacc agcctggcca    86940
acatggtgaa gtcccatctc tactgaaaat acaaaaatga gccaggcatg gtggcgcaca    87000
tctgtaatcc cagctacttg ggaggctgag gcacgagaat ctcttgaatc caggaggtgg    87060
aggttgcagt aggccaagat tgcaccactg cactccagcc tgggcgacag aatgactctg    87120
tctcaaaaaa aaaaaaaaa aaaaagaaa gaaagaaatt gctttcctag aaaaagtgaa     87180
aaaaagcaaa cattaattgg gcctagcact gtgctatttt ctttactcac tttgcttaaa    87240
gggagtcagt actgagagct tccataatta ctttggtaat agcctttgaa aacgtagttt    87300
gctttgactt atctgatgtt ataaacactt gtgtaagagg tctttaagat ataagttcca    87360
gttttagatt tcaatagaga cacacaacgc aggcaaagta aacatcaagg gtatgtaagt    87420
ttatttctat cagtggagaa catactttgt catgtcctgg tttaaactgt cctagaaaag    87480
gcatatttgt taaaaaaaaa aaaaaaaaaa aagaagaag ttttcaaaga gaaacttcac     87540
aggaatgaaa tgtgttcttt ctctctctat agtataatcc aaccaaagta aaatatgaga    87600
aaaggtgtac ttccaaataa taaaaataag gctgggcaca gtgactcacg cctgtaatcc    87660
cagcattttg ggaggctgag gtgggtggat cacttgaggt cagacgttca agaccagcct    87720
ggccaacatg gtgaaaccct gtctctacta aaaatacaaa aaattaacc aggcatggtg     87780 gcgggcgcct gtaagctcag ctactcagaa ggctgaggca ggagaatctc ttgaacctgg    87840
gaggcagagg ttgcaacgag ccaagattgc accattgcat accagcctgg gcgacaagag    87900
```

```
tgagactctg tctcaaaaaa caaacaaaaa ataacaaaaa taagaccttt gaaacagatg    87960
attaaagtaa aagattgaca gttagcttca attcttataa aaaattgtta aatgaaagag    88020
atatgaaata accacaattt gctattatag tatatattag agctagatga tgggtagtat    88080
ttttccatat tttatcctgc tttatgtcaa ttaattccta gttaatgctg aaaactaact    88140
gaaaccattc ttggagctat ctatttgagg gaccctgagc tgatatagaa aacttttacc    88200
tgctttgaga atataacctt taagaagaaa agggggggct gggcgcagtg cctcatgcct    88260
gtaatcccag cactttggga ggccgaggcg ggcagatccc tgaggtcag gagttcgaga     88320 ccagcctgat caacatggag aaaccccgtc tctactaaaa atacgaaatt agccaggcat    88380
ggtggcacat gcctgtaatc ccagctactc gggaggctga gtcaggagaa ttgcctgaac    88440
ccgggaggcg gaggttgcta tgagccgaga tcgcgccatt gcactcctgc ctgggcaaca    88500
agagtgaaac tccatctcaa aaaaaaaga agaggaaaag aggggtgggg aagttcttca     88560
atttcaaatt ctttcagtgc actgtaatta attggaaagt ataagttgga ggagtagcag    88620
taattttatt ttattttccc caggaagaca gattatatat cagcatattc aggaaatcta    88680
agaagattag gagctgtgta atgaagtata atatgagtta ggagatcaac tctggctgaa    88740
catccttaat atttgtgtcc tttattttga aagatttcag ttaacaacag aaatgttatt    88800
tttgaagctg caggctcaaa catgtttttg ttggttatgg tataagttgt ataaaagctc    88860
atcagctaaa ctgaaaatca tattactact gaagcagctg agtgcatgct ctattctttg    88920
aagtataatg ctaaatagta ctagtttaag acaaaaatgt ctgctgcctt tatattcctt    88980
actttattac atggatcttt tcctggcttt caaaaaaaca aaaaaaaaag cagtcttgag    89040
cgttcagaaa atttatagaa cactgtctgt tctaagtcac acctatctag gagggcttat    89100
ggagtttatt tcagtaataa tatagtagtt ccttctaacc ttaagattac atgcatggct    89160
gagaatcttg agaaatttgg attaagactt gataaaatat tcctttaaa aatgactgaa     89220 aagcaattgg tacaccttaa atctgtttgg cagtgattaa tgtagttccc taaatctaat    89280
tctgttttgt aaacgtgatt gaaggttatc aatatctagt ggttatcagt aggtagataa    89340
ttgtggcgct ccttcaacct ctaccctcca tccttttcaa ggccttctag ttccttaaga    89400
gaactaaatc taggcctggt gcgatggatc agttgagggt caggagtttt agaccagcct    89460
ggccaacaaa gtgaagccct gtctctacta aaaatacaaa aaattagcca ggcatggtgg    89520
cacttgcctg taatcccagc tactcaggaa gctgaggcag gagaatcgct tgagcctgag    89580
aggcagagat tgcagtgagc tgagatcgca ccactgcact gcagcctggg caacagagtg    89640
acactccatc tcaattaaaa aaaaaaaaa agaggccggg cgcagtggct cacgcctgta    89700
atcccagcac tttgggaggc cgaggcaggt ggatcatgag gtcaggagat cgacatcatc    89760
ctgcctaaca tggtgaaacc ccatctctac taaaaataca aaaaattagc cgggtgttgt    89820
ggcgggttgc tgcagtccca gctactcggg agtctgaggc aggagaatgg cgtgaaccca    89880
ggaggcggag cttgcagtga gccaggagca cgccactgca ctccagcctg gcaacagag    89940 tgagactctg tctcaaaaaa aaaaaagaa ctaaataatc taatgatgct gttacagcat    90000
attgatcttt tatatctatt ccttccttcc tgagaataag atttattgta aagaggttga    90060
agactaaaaa tgacctgtta aagttatcta cattttccaa gaaattaact acatatttac    90120
ttttctctgt ctcttccatg ccaagctgta gattttttta cagtgagtt cctaaaaata     90180 gttttattct aacaaaccat attgaagtcc aaaaggacag ccacacagtt aagtttattt    90240
```

```
gtaaaattca agagtcagta cagattttc tcctccaaat tgcttttatg cttttatca     90300
cccttaaaag taaagattta tgtttgaaaa gtaggaaaga attctgacct ctttatattt    90360
ccatctgtgt tctttcggag ccaaagataa aaacttctta agagcagtat tttttaaac     90420
agtgctaaac tttcttcttt gtttcaagtc tgtattagac cagatacttg ctgaaactct    90480
gcagtgaaaa atccttggga ctgagctact acactggcgt taaatagcaa ttggtcttct    90540
tgcataaata ttaactgcta ttttatatga tactcaagtc aaagtgggta actatgttgt    90600
ctgttaagat tcagtttcac tttaagagca aaggataact attttctaac gtgtaaatgc    90660
cagggcttac tgatttgtct acatttattt tactgctttt attttcctgt tattctcttt    90720
gaaattagta agttaaacca taagaaattt cctgctttaa ggtcaaaaat ggtagcatgt    90780
tggcagtttg atggttcagc ctagcaattt taaaggataa caggccactt tattttata     90840
tatttattta tttatttgag atggagtctc tgtcacccag gctggagtgc aatggcataa    90900
tctcggctca ctgcaagctc cgcctcctgg gttcatgcca ttctctcgcc tcagcctccc    90960
aggtagctgg gactacaggc gcccaccacc acgcccggct aatttgttt ttgcatttt      91020
agtagagacg gggtttcacc gtgttagcca ggatggtctc gatctcctga ccttgtgatc    91080
cgcccgcttc agcctcccaa agtgctggga ttacaggcgt gagccaccat gcccagccct    91140
cctttttaaa tttttttaat ttttctttt ttttttcgag acggagtttc actcttattg      91200
cccagggcag agtgcaatgg cgcagtctcg ctcacggcaa cctctacctc ccaggttcaa    91260
gcaattctcc tgcctcagcc tctgagtag ctgggattac aggcatgcac caccacacct     91320
ggctaattt gtattttgg tagagatggg atttctccat ttggtcaggc tactctcaaa       91380
ctcccaacct caggtggtcc gcctgtctgg gcctcccaaa gtgctgggat tacaggcgtg    91440
agccaccgtg cctggctcat ttttcgtaag tgacagagtc tcacactatg ttacccaggc    91500
tggagtgcag tggctgttta caggtgcagt catagctcac tacagcccca aactcctgac    91560
tcaagagatc ctcctgcctc agcccccaa gtagccagaa tcacaccact gtgcctggct     91620
ttccttttt taaaaattga tacataatat ttatgggta catatgatat tttgatagat       91680
gcatacggta tcaaatattc tgatcaaatc agagtatttt ggatatgtgt caccgcaaac    91740
attatcattt ctgtgtgttt agaacatttc agctcttcta gctatttga aatacacggt      91800
aaactattgt taactgtagt catcctgtgc tatcaaaagc tataattat tcctcctatc      91860
taactatatg tttgtaccca ttaaccaacc tctcttcaat ccccctttcc ctaccattcc    91920
cagcctctgg taaccactgt tctactctct acctccatga gatcaacttt tttagctccc    91980
acatgagtca gaacatgcga tacgtgtctt tccgtgcctg gctcatttca cttaacatca    92040
tgaccttcag tcccatccat cttgtgcaaa tgacagcatt tcattctttt catggctgga    92100
tagtattccg ttgtgtgcat ctgccacatt ttctttatcc attcatccgc tgatacttag    92160
aatgattccg tatttggctc ttgtgaatag tgctgtagta aacatagctg tgcacacatc    92220
cctttgatac actgatttcc ttttatttgg ataaacagca gtagtgggat tgctggattg    92280
tatggtagtt ccattttag tttgaaaaaa cttttttttt tttttttaac agaggctagt     92340
taatttgtga ttagatagct aaaaggtttg tgattttttt ttaaaggtgg tggctgggca    92400
gcatggtggc tcactcctgt aatcccatgc cacaatcaag gttagaatat tttcatcgtc    92460
cctcctggaa gttcccttct gccccttgc tatcagccgc cttcccatac tttctggcaa    92520
ccatgaatct gttttctgtc attacagtat gtctttttag agtttcatac aaacgaattc    92580
atacagtgtg cagtctcatg tctggcttat ttcaatgaac attatatttt gagattcatc    92640
```

```
agcattgttg ccttagcaat catttgttcc ttttcatata tttcctttct ctcctcatgt   92700
ttcttctacc ttttttgaaca tatagatcat atttataatg gcctttaaca tccatatctg   92760
ctaatactcc gttattttg gtcggttttt attgactgac ttttcccctg gttgtacgtc   92820
atattttcct gtttctttga atgcctggaa ttttaaaatt atatgttgga cattaatttt   92880
acattgctag tttctatatc ttgttgtttt cctttaggta atgttggact ttgttcttgg   92940
aatcagtagg atccttcaa agcttgcttt taaggttagg gtgggttcag accaattttt   93000
agtctagggt tcatttatct ccactactaa ggtgatagga gtagagtccc cttctgagga   93060
ctctgttaga taacccacat attataagat ctttatattt tggtggacaa aaatacaaac   93120
tattcccagc tccatgtgag tgcaggaatt gtttggccta ttgctttctg atggatcttt   93180
tccccagcct ctgctagttt cttttcatgc gtatagaaat cagtacccctt cccaaagttc   93240 aaagggaccc ttcagcagat ctctaaagct ctctcatcgc accccacctc cctgctcctg   93300
tacactgccc aacaaattct agccccgca gcctccccag ctctgatctc aactgaccac   93360
tctccactcc aatctcagat gtcctcagct ggcaagactg ggccctcctt ccctgtgcag   93420
cagcctgcaa cctgccttca ggcagcacag tctggcattc cccgtggttc aatgtctaaa   93480
agtcattgtt tatgtacttt gtccagtttc ctattgttta cagcaggaag ataaatccag   93540
cctctagtac tccatggcca gaagaagtct catcttctaa atgtaaatta agcatgtatt   93600
gatacttcta gggggaagtt aggggacttg gctcatcagt tcccaacata cttaaatata   93660
acacacttta atgtctgctt tcttctttgt aacttaagcg atgacataaa tgatgctctt   93720
cagtgctcac actaggctaa tctaagcttg agtgtttttc tgtgatcaac ttgaaattat   93780
ctacataaag agtattaatt ttgacttatt tgtggccaac ttatatagag tagcttccca   93840
tgaatgatgg atatgttagt attctgattc taaggacatt gttagctatc tgtatgtctg   93900
gttaatttgt cataagaact tatgtcatgt atcatgcttg gacttttaaa aatatgaact   93960
tgctgatttt ataatctata tatgaaaatt actgcagcct tttctattca tgagtattca   94020
tggttgagaa gattctaaaa cagttcttag ccctttccaa gcagatcttt taaatttatt   94080
gctttgctct gtataacaga acagttgttt ggatatcttt tcaaagattg acttaccata   94140
atgtcaaaac ctgcccaaat atttagtcag ttggcaattg cagacagaaa cgtgtgtttt   94200
aatctatttg tgttttaggg aagatgagca aaataggatt aaagatacga ttttatacta   94260
ttacagatat gttactgttg tctggtaaga attttaagga aacaggctag gcgcggtggc   94320
tcatgtctgt aatcccagca ctttgggagg ccaaggtggg tagatcactt gaggttaggg   94380
gttcgagacc agcctggcca acatggcgaa accctgtctc tactaaaaat acaaaagtta   94440
gctgggcgtg gtgatgtgca cccgtaaccc cagctatcag gaagctgaga caggagaatc   94500
gcttgaaccc gggaagcaga gattgcagtg agccaagatc gtgccgttgc actccagcct   94560
gggcgacaga gtgagacacc gtctcaaaaa aaaagaaag aaaaagaaaa aagaattgt   94620 aaggaaacaa caaaatgaaa ctcagaagat gaaaatttgg gggtctaaag gcttcatctc   94680
tggtcttatg tgtaaaattt atttgcagca cagttaatta gaatgaatct taaagttaga   94740
agatgtaaat tctagttgca gctatgccac ttgctacttg taatgtgcca cacactattg   94800
tgcaactgta ggcatgtcac taccttggtg agagtctccc cacctataat atgaagataa   94860 tcataaaatat cctgcctact gtcaagggat ttgtggagtg ctcagtgagg gggtatggct   94920
gaaattcttt gaggatgcta acgctccatt aaacgttttt tacattatta taacttctgc   94980
```

-continued

```
tgttaacagg tagaatgaca gaatacaaaa tgagacattt tacatttata ttccatatgg    95040
tttactctgt aaaatatttt atggtgaaat ggaaaaaaac gaaacagaac tgattagata    95100
gaatggagat agaggagatt tactgtcttt tttccattcc tttttactta ggattatttt    95160
gttttctctc accgtgactt tccaggtaaa gagtgtgtac aacagttagc tgaaaacacc    95220
aggtatttca ggagacgcct gaaagagatg ggcttcatca tctatggaaa tgaagactct    95280
ccagtagtgc ctttgatgct ctacatgcct gccaaaattg ggtacgtttt gttgcagatc    95340
acagaccagt ctgtccttat ccttatctgt gatgtgagac cagggcttat gtattttgtt    95400
agggaaaatg gtcttgtcct tactgtgtta accttcattt ggtacatatg ccatagatca    95460
aatagtggat tccaaattgt aaagtatgtt aatttgttct tctttcatta aacatttgag    95520
tttcatgtac tctctagggg cctgggatag atcagtgaat aaaatacaaa catctctgtc    95580
cttgtggagc ttacagtcta gtaggggca acagtcagac agacataata aacaaatgaa    95640
ctgtgtacga tgttagaagg tgtcaagtgc tatggaaaaa aatagagcag gacctatatg    95700
gggagttgag agtgccctgt gggcgggccg ataacactat taaataggggt ggtcaggta    95760 aggaagcctc cttgggaagg aaaatgacat ctgagcaaag atttgaagga gctgacagcc    95820
actggagaaa gaagcatctg tgcaaaggcc acagtacaga agcgagcttg cttagctgac    95880
ggaagagtag caaagaggtc cctggaattg gagcaccgtg ccccagggcg agcagtgggc    95940
catgaggtca gagaggtttt atcagagtgt gttattggat acttaccagg tgtgcagatt    96000
acaccagctt ctttggtttg tatgaggcat acataatgga aagccctgcc ctaggatagc    96060
tttcaatgta tttgagaagt ccagatgtat aatgaaacca gaagcatttt gaaaagcaaa    96120
tgaacagtaa ttatactgaa caaattttat tatatgcaaa gtggccctga agatgtagaa    96180
taaggagtgc acctgcttag tataggctca gtaagaaagg cacatcttgt tggatgggtg    96240
agttttgagc tggatcttaa agcatttctc cagtttgatt gaactcattg aaggagcaat    96300
ttttgtaaat ttttgaatcc ccagtgtcca ccacagtctc cgacactcag taaatgttta    96360
ctgaaatgaa tatgggagag gaaattaaat cagggaacct ggaagtaatg tgattcaaag    96420
agaatgaaag ggaagtaagg aaaaggtgct ccctgagaga aaaagaagaa tttgggtttc    96480
aacatgaagt catatgggca gttggtatta tggcttcaga ggggatgggg aaggattttc    96540
ttcattcttc tttaagtgga attctcataa acaaacatga agagttatca gatccaaagg    96600
actcagtcta gagctctctt taaagaaggc tgtgtctcct ttattctaca taggtgcaac    96660
tgactgtgta cactttaatt aggaaagatt tagagaaggt acaggaccca aaagggcaca    96720
aaaaagcaat aactactaaa tataaggaaa acaactctgt atacagcatg tataaagaaa    96780
agcaaggtat atttggggag ataaaagttg taaaggcatt aagatgtgtg tttgttgaga    96840
aaaaataaat ttgtgcattt aagaagttaa aaaaaaaaga tttagagaag gtaaagaatt    96900
agaataaggc actagacagt ttgggagcat gtgctgaaga tacagggcac ccaggttcat    96960
gctgacacaa aggaggtatg ttgaggaaga tgtactggta ctacagagag tgggaaaagg    97020
ctgtgaaaag actggcatta atgtaatgcc aaatgtgcag gatctgtata gcccaggctg    97080
gagtgcaatg gcgtgatctc ggcttactgc aacctccacc tcccaggttc aagcaaatct    97140
tgtgcttccg cctccccagt agctgggatt acagatgtgt gccaccacac ctggctaatt    97200
tttgtatttt ttagtggaga tggggtctaa ccatgttggc caggctggtc tccaactcct    97260
gacctcaggt gatctgcccg cctcggcctc ccaaagtgct gggattacag gcacgagcca    97320
ctggcccggc cacatttttt tattctcaaa caaatgctgt aaacagctta aaggaaaagt    97380
```

```
tgaaacataa gggaggtcaa taagaggaaa agacaaaaag caacataatt tgggccaggc    97440
acagtggctc acacctgtaa tcccactttg ggaggccgag gtgggtggat cacaaggtca    97500
ggagatcgag accatcctgg ccaacatggt gaaaccccgt ctctactaaa aatacgaaaa    97560
tcatctgggt gtggtggtgc acacctgtaa tcccagctgc tcgggaggct gaggcaggag    97620
aattgctaga atctgggagg tggaggttat ggtgagccaa gatcgtgcca ctgcactgca    97680
gcctggcgac aaagcgagag actcaaaaaa aaacccacat aatttagtag acaaaattaa    97740
ctaaaagtta gaatgtgtta tttagacaag atacagatgt ggagtaaggc cacagggcct    97800
ccaatttggc ttacgatagg ggtgggggat tgttaaatac gaattgtgtg gtctgagtaa    97860
tcagctgaag ccagcgggtg aactggcctg acagacacca aaggaagccc tgaattctga    97920
agcagtgttg ttcccaagac aattaaagaa acgtgtgatc tggagagctc atgccagtca    97980
gccattctgc tagcagaaaa gatgtgccgt gttacagcag atcccccaca gctgcagaat    98040
cctcagaatt tgcggattaa tgttaaactg ccaagcttaa catttcaagg accagatttt    98100
aattaaatac aggttcattt tgaagcctct gaaccactat tacatatcag ggacactttt    98160
tttttttttt gagacagagc cttgctctgt tgctcaggct ggagtacagt cgtgtgatct    98220
tgccttacta cagcttctgc ctccaagctt cgagagattc tcatgcctca gcctcctgag    98280
tagctgggac tacaggtgca tgccaccaca catagctaat ttttttgtatt tttggtagag    98340
acgggatttc accatgttgc ccaggctggt tatttcagtt ttgtgaagga caccatatag    98400
gagaagactg ctttaggatt gactttaaaa gtatttgtga gctgtcaatt ttaactttaa    98460
aaggagttaa aggaaactcc tattagaagt ctccaatgcc tgcatcacca aagagttgaa    98520
atctttgagg acagcaggtc ctctgtaatg agtgcttttt cactcctcct ggtttctgtt    98580
cttgttttcc cctttgcagc gcctttgac gggagatgct gaagcggaac atcggtgtcg    98640
ttgtggttgg atttcctgcc accccaatta ttgagtccag agccaggttt tgcctgtcag    98700
cagctcatac caaagaaata cttgatactg taagtaggca ctttcacctt gatataaata    98760
tgccttttat taaagggcc tgtatattag atgaaattca taatatattg atcttgatgt    98820
tcttgtgagc acctaagaca gaggggggtga cagtgctacc aaaaacattg gcatttacaa    98880
aaaaactgtc acccaccaca cctgcatcat gagagctctg gagaattttc cggctttgtc    98940
ttgctctact gtctccctca ctatggactc tacaattctc tttccactct agctatttct    99000
acattaagct ttctcatatg ttgttctgtc taaaattttc tctcttgagc tttctctccc    99060
ctctgcctgg ctgactgcca ctcattcttc acatctccat ttaaaggaaa attgctcagg    99120
ggcgccccac accttcttgc tctgtgttcc cttggaatcc tgagattctc ccttactaaa    99180
ttcttcacac ctataattat ttaatagcag tcttctccat tagataaata ttgaggatag    99240
gaataagtct gttttactga ttctatatcc cagcacccac cacactgcca ggcatctagt    99300
tgggatcat tattactaag cttaattatt tattatctca agatattctc atctctatat    99360
attctcttaa tatgttattg ttgcaagtct aagatttcag agtttaaatc attattgcca    99420
tctgggagtt tataaagctt tagaacatga catttgcata aaattagttg ctagaaatat    99480
ccattaatga gttagagagc tactaatttt tttttctttt tttgagagag agttttgccc    99540
ttgttgccca ggctggagtg caatggcgtg atctcagctc accacatcct ctgcctcctg    99600
ggttcaagca attctgcctc agccccctga gtagctggga ttacaggcat gcgccaccat    99660
gcccagctag tttttgtattt ttagtagagt cagggtttct ccatgttggt caggctggtc    99720
```

-continued

```
tcgaactccc gacctcaggt gatccgcctg cctcagcctc ccaaagtgct gggattgcag    99780
gcgtgagcca ctgcctggca agagctacta atcctaaaga acattatgaa tgcttcttta    99840
taaaagttaa ttataacaat ttgatggaca ttttgtattc ctgaatagcc gaagacttga    99900
cttttcttct ctgtttctac acagcaaaat ttctatgagt ataagtgtat tcccttttaa    99960
aaaacaaaat tgtagtaaga acacttaaca tgagatctgt cctcttaaca aattttttcca  100020 tgtcgaatac agtattgtta actataggca cagtgttgtg agcatattct taattacatt  100080
ctgacaatat ccaattagat tcaactttt gatattgtat cttttttttc tttatttga   100140 ttatgcctgt cagattttc caatggattt ttctcatttc tcagaaattt tactggtgaa   100200
tttctgtgat gatttttttt aacctagaga tttcagcttt tctttccttc ctactctatt  100260
gatgttttaa gaattttctt ttttctttct catgttcacc tgttaactca gaatttcaat  100320
gtgcctttaa aaaaaagtct gtgtaactat aaccagtgtc tatggcagta atccatgcct  100380
tctgaccaca actttgactt ctgagaactg tacacattca tgaaagaatt tagatgtaac   100440
caggatatct ccttaggata tctaaggaga tttctgttgc caacaagtat gtttgccaac   100500
tgagagttct aatcctttc ataagattct cttgagggat tgttgggctt tgcctcccat   100560
ttagtttttt aaagcataaa gtgcatttt tgaaaccatg gatttgttaa agtcattttg   100620
tcttatgatg ttttatggaa ctaaacgtgt actagaccat tatgagatac aaattaattt   100680
tcatttaata atgggcctca tgacatgatt ctgtatatag aaagtgctgt aaaatacaca   100740
cacacacatg cgcgcgcgcg cacacacaca cacacacagc tagagctcat aaatgaattc   100800
atcaaagttg cagggtaaaa gatcagcaca caaaaaatta gtgcttttat acaccagcaa   100860
tgaacaaatg aaaagaaaat ttcttttaca attttcaaaa gaagaaaata cctagtaata   100920
aacttaagaa agccttctcct ggctgggtgc ggtggctcac acctgtaatc ccagcacttt   100980
gggaggtcag gcgtttgaga tcagccttgc caacacagtg aaacctcatc tctactgaaa   101040
atacaaaaaa ttagccaggc atggtggggg gcacctgtaa tcccagctac tcgggagact   101100
gaggcggaag aaccacttga atctgggagg cggaggttgc agtgagctga gatcgcacca   101160
ctgcactcca gcccgggcga cagtgcgaga ctctgtctca aaaaaaaaaa aaaaaaaaa   101220 aaaagccttt cccttgtaca ctggctaatt tacacttgta cactgtatttt ttagatgtgt   101280 atattgaaaa ctataaaact ttgctgaaag aaattacaga agacttaaag aaatggaatg   101340
acatcctgtg ttcatggatt ggaagattta atattgttaa gatggcagta tagcaaccta   101400
cagatcctgt gttcagcatt tctcagaaaa aaatggactg ggagaccca agccactggc    101460 ccttttttgc agaaattaaa aggctgatcc tcaaatgtat atggaactgg cagggaatag   101520
ctaaaatagt actgaaaagg aaaagcaaag tgggaggact cacacttctt aatttaaaa    101580 caaagctaat tactacaaag ctacagtaat tacaacagtc gagtactagc ataaggatag   101640
acgtatagac cagtgaagta gaattcgagag ttcagaaata aagcacaagc atctatggcc   101700
aatttgtttt caacaaggga gccaagacca gtcaatgaga aaagaatagt ctcttcaaca   101760
aacagtacta ggtcagctgg atgcagaaga gtgaagtttt aaccctacag catggataaa   101820
ccttgaaaac attaggctaa atgaaagaag ccaaacaaa gactacataa cttacaattc   101880
catttataag agatgtccag aacaggcaaa tcatagggtc agaaaataga ttggtggcag   101940
ccagcctgag aggagggga gtgaggattg agacaacgag tattggggttg cttttttagg   102000 tgataaaaat actctaaaac tagatagtga caaaagttgc acaactctgt gaatatactt   102060
agaagcaatg aattgtatac tttaaaagtg aattttgctg aatgtgaatt gtatctcaaa   102120
```

```
gctataattt tgttatttttt taaaatggga agcgcaagga tattggctca ggggagcggc    102180
aggatggctg tcctagagga ttcggttact cagctctata atgaatacat gtttttctcc    102240
tagaacccca ccttacctgt gatctagagg ttctgtgtag actgttaatg aatggcgatg    102300
catgtaatgg ctgcctgtcc ctaacatacc caaatacccc acacaagagt cagcactcat    102360
tagaatgtca tcttatattc acatgacacc gatttgtctg aaatatttgg agtgggatca    102420
aaggaaatct tgtaatctag atcccctcgg gctactgagg atttctttt ctatctaatg    102480 attacttttc tacattgatg aaaaaattct agattcttct aaagtttata aatgtccatt    102540
actttgtgat cttagtcatg tgcactttgt tcttattatt attattttga ggcagggtct    102600
cagtcaccca ggctggagta cagtggcatg atcttggctc actgcagcct ccatctccca    102660
gcctcaaggg atcgtcccac ctcagcctcc agcatagctg gactatgcc tgccaatttt    102720 ttttctttt aagagacgag gtcttactat gttgcccagg ctggtctcaa actcctgggt    102780
tcaagcagtc cgcctgcctt ggcctcccaa agtgctgtga ttacaggctt gagccaccgt    102840
gttcagcctt gactttttt ttttttttt tgagacagag ttttgctctt gttgcccagg    102900
ctggagggca atggcatgaa ctcaactcac cgcagcctcc gcccctggg ttcaagcgat    102960 tctcctgcct cagcctcccg agtagctggg attacaggca tgtgccacca cgcccagcta    103020
attttgtatt ttcagtagag acaggggtttc tccatgttgg tcaggctgat ctcaaactcc    103080
cgacctcagg tgatctgccc atctcagcct cccaaagtgc tggaattata cagacatgag    103140
ccaccgcgcc cggccagctt tgacttttgt cttaaattat tacatcttgt cacagaggtc    103200
aggtgaataa atggtcgatg ggttctccca gcttaatttc agacttaaat tgtttccatg    103260
tggagctttc acttatacct cttctcagag gtaccgctgt tgtgatagca cattgacgtt    103320
cagctcttat ttgcttttat attttcaca ttttgaaatg aagaatattt ttcttgtgc    103380 tacaatacat cagtaatact ggtggttttc tctctccaaa cactgatttt ttaaaaaaat    103440
gaagtttaag atgccaggtg tggtggctca tgcctgtaat cctaacactt tgggaggcag    103500
aggtgggtgg gtaacttggt gccaggagtt caagactagc ctggccaaca tggcaaaacc    103560
ctgtctggac aaaaattagc tgggtgtgat ggcacatgcc tgtagtccca gctactcaag    103620
aggctgaggc agagaatctc ttgaacccag gaggcagagg ctgcagtgag ccgagatggt    103680
gccactgtac tccagcctgg gtaataaagc aagactctgt ctcaaaaaaa aaaaaaaaa    103740 aaaaaaaaa gttgctgggt tcgttggctt acgcctataa tcccaacact ttgggaggcc    103800
aaggtggtgg atcacttgag gttgggagtt caagaccagc ctggccaaca tggtgaaacc    103860
ccatctctac taaaaataca aaaattagct gagcatgatg gcgggcacct gtaatcccag    103920
ctacttggga ggctgtggca ggagaatcac ttgaacctgg gaagtggagg ttgcagtgag    103980
ctcggagggc gccacagcac tccagcctga gcaacagagc gatactccat ctcaaaaaca    104040
aaagggagag atgacaaatt gtattcggtt ttgtaagttc agagtgcata taacttttc    104100 taccaagcat atcatacttt gaattatagc ctttattctg catacctggc tattcacaac    104160
ccattattca tggtgagctt gaaggccttg ttcaaaaagc agctccttcc acagctgtat    104220
tgtagtctga tcttgtaaat gcactagaca taagtcctgc cgaaggataa tcttgccatg    104280
attgttttta gcaaagtaaa acaccaggca tgcctgcatc ctactggctc tgacagacct    104340
ctactttgtc ttgtgtattt taggcttaa aggagataga tgaagttggg gacctattgc    104400
agctgaagta ttcccgtcat cggttggtac ctctactgga caggccctttt gacgagacga    104460
```

```
cgtatgaaga aacagaagac tgagcctttt tggtgctccc tcagaggaac tctccctcac   104520
ccaggacagc ctgtggcctt tgtgagccag ttccaggaac cacacttctg tggccatctc   104580
acgtgaaaga cattgcctca gctactgaag gtggccacct ccactctaaa tgacattttg   104640
taaatagtaa aaaactgctt ctaatccttc ctttgctaaa tctcaccttt aaaaacgaag   104700
gtgactcact ttgctttttc agtccattaa aaaaacattt tattttgcaa ccattctact   104760
tgtgaaatca cgctgaccct agcctgtctc tggctaacca cacaggccat tcccctctcc   104820
cagcaccttg cagacttggg cccatcaaga gctactgctg gccctggctc cgcagcctgg   104880
atacttacct ggccctcctc cctagggagc aagtgccttc cacttacttc ccatccaggt   104940
ctcagaggtc tcaaggccaa ccttggaatc cttatttaac cattcaagta atcaacggaa   105000
gttttcaccc tttaatctta agtttagcct tttaagaaaa acagtaagcg atgactgctg   105060
aaaggctcat tgtgtaatct cccaagggtt tggtcttatt ccatttctt ctggtcacca    105120 gatgatttct tcctttacca tcaaatactt cttcataatg gtcacagtct gaggatgtgc   105180
gcaaattctg gttcttccca agctctaacc gtaacacgtc ccacccctt tttaaagcac    105240 ttactgtttt cagagcaccc atatcccacc ctggtgagaa ggccactctc acatctgagt   105300
gttgggtaca aagctgctcc gtagagtgat gtgcactcct ggtgggtgag gggcagggc    105360 agtggcagtg tgcaaagaat tgattactcc ttgcagagcc tgtggcttgc atttcctact   105420
gctttctacg tttgaaaatt atgacagtct ctggctaggt ctgggtccag attaggattt   105480
aaactgataa aggaaactgt tggtaaatcc tctgctcaga aagcatttat catgttccta   105540
tttaaggatt aggtttatta atttaggcct cttagaagct aacccactta aatattactc   105600
ttctgaatgc tagttctctt ttattcttga tgtcctaagt caattgaatc tggcatctgg   105660
ggctagggtc tgcctgtcta catatttttt attttttct gagaaattct gaacacatag    105720
atctctttcc taaactgaca ttttctattt tgactgtttt catactataa ccaggtaaag   105780
ggacttcttt cagagagctt tatactgcct gaccaaagaa caaatctgaa aatcaccatt   105840
ttaaagttat ttttttcagtt gaaccaaagt ttaagtgaag aggacttttg gcatattata   105900
cccaggatca gtttgtcttt ttgtatccat caagtattac aggagaagga ttgggaacag   105960
aatggaaaaa cagtgtatga aagtcatgtt acaggccgag tgcggtggct cacacctgta   106020
atcctagcac tttgggaggc tgaggcaggt ggctcacttg aggtcaggaa ttcaagacca   106080
gcctggccaa catggtgaaa ccccgtctct actaaaaaga caaaaaatta gctgggcgtg   106140
gtggcgggca cctataatcc cacctacttg gtaggctgag gcaggagaat cgcttgaacc   106200
caggaggcgg aggttgcagt gagacgagat tgtgccactg cactctagcc tgggtgacag   106260
agcaaaactg tgtctcaaaa aaaaaagtca tgttacacat ttaagttttt gaaattgctc   106320 ctttttatcgg taaagattct caatccaaat tctcctgggt gtgttgtcat cagctgtgat   106380
atgtttgtgc acattacgta tagcagagga tgtaagcaat attattgttt gtgaagtttt   106440 gttttttaatg tcttgagtat gagttatgtt tagtcactgt cagcatctga aactttaat    106500 aagcccttga gatattccaa agttttattt tactttttta aagaacagaa aaagatgaat   106560
gaaagaacca aggagagatg cagagactat atttagcatg tataggttaa agtaagaagg   106620
aggttgtggt aactaaatag gagtcctata aaatcaaata cattgtcaac cttttctgca   106680
catctagttt cctaccatag aatcccactg gaataccaca tagcttttgc actgcagtta   106740
ctatttacta atgtaaacgt aggggtttgta aaagtcacaa acttataagc aatgaactta   106800
cctgctagtc tttttatttt ggcttgcatg aagtcactgc aaattcaaat gtcagtaccg   106860
```

```
gcatttaaaa tatatctata tcactttgtt ggtacaaagt tatttcaaga taagtgtaat 106920
tttgttacaa gtttattttg aagagacaaa tctcctgtga tctatgcagg acctctgtac 106980
tttctaaaga acaaaatgtt atgtagacat tatacatggt tggttgtctc ttcttgaaac 107040
tgtaatgtaa atctagggtc cagtcatatc ctaggtatca tcatttatcc aagtacttgg 107100
aggaatacaa gtatatataa atacagtcat tgagaataag tcgatttgag gcatacaaga 107160
gtagtttctt acacagttta acacggcctg attcaagact ctgataggat tcaaacagat 107220
accggttaac catgactacc aaaactgatc atctgagtcg attgatagag gtgtgactag 107280
tccttagcac tttttctcat tcctctttt attcagcatt gctgttacct atttcaggtt 107340
tataagacct ctttcagcag atcacatcag aagccaggaa atgcatagct aggagatgtc 107400
aaaagcccat atgaggagtg gaccaagcag cagtggcggt ttctcctcgc atcttttttt 107460
ttttaagctt taacttagca ggggcatgga cttatagca ctttttcaac ttttgctt 107520 gctttggata agaaatcctt acctttaaaa aaagcttcta gtctccataa cccccaaagt 107580
actgcttatt tgtttgaaga atccagccat cgtagtgctt tagtcactat cgtaaacatt 107640
catgataggg caaggatttt aaaacaggat tcttgcttct gtagtcatca aggtgaacag 107700
aagcatccta cacaaccact aagggctcta tgtttgtgtc atgcctcttc aaacaccaag 107760
gagttgaaca tgcttccagt gatttgtctc cgtaatgcct tcttcctta tttgccttt 107820 cttctttct gtaccttcaa gttcttgatt tttaaaattc caactctaga gaaaaccaat 107880
atatggtggt gctgggcttt gaagatagca tatcagacgc cttggttctg tttgtacact 107940
tagccttaca tttcaggagg aggcttttca ttagggggctt aagctagctc ctttggcttt 108000
taaaaaaaat ttttttttcaa atttcttcat tacctaaggg agcctgcatc taaatttctc 108060
aactagttca gcctagctga attttctagt gtgttataca ctttgcttcc ttcttattgg 108120
tgaaaaccag ggggatgagt ggcttccatg gagagatttc ctgatttctc agggaggaaa 108180
aaagtgatga catttaccac tacttttatg tttttcccct tttccaaat tgataaggat 108240 ttctggttcc tagtgatccg ggattgggca acagtgcaga actgccagtc atgccgtagg 108300
ccgtgaagaa agaatgtgag taactgttgt tttgcaagga tttgtagggt tatgggcagt 108360
tgttgtttga agcattgcta tgacctaatt cccaaggtat cttcctctc ttggtgttct 108420 aggtaagcca atgagcttta atctctactt gctataaccg tgtgcttaga aaagaggtg 108480 agagtagtgg ttttccttca aactgtccac attcatgaag attatgaatt gttaggacag 108540
ccagggcaag atagaccctg tctctacaaa aattttttc taaattaacc gggcatggtg 108600
gtgcctgcct gtagtcccac ctgtgtggga gaatcacttg agcctgggag gtcaaggctg 108660
cagtgagcca tgattgcacc cctgcactcc agcctgggtg acagagtgag accctggctc 108720
aataagaggg ggaaaaaaaa ttgttaggag ctgggtgcgg atgcagcctg caatcccagc 108780
tacttgagag gctgaggccg gaggattgct taaaccccaag aatttgagcg tagcctgggc 108840
aacacagcaa gaccccatct aagaaaaaaa tgtttttta atcagcttag cccaaagggg 108900
ttgtgaatgg ggaggtataa aaagcaaaga ttatttttg gctactaagc caagaactta 108960
cagggatttt ttttttcagt cccagaacct acagataccc tgctacttgc ttcacgtgga 109020
tgctcagtgc ccagcagcca tcttaataca ttaaaccagt ttaaaaaata ccttccatgt 109080
ggagaaaaac atgtcttttt ctcgcctcaa ctttatccac atgaaatatg tgcccatggc 109140
tgggcgcagt ggctcacctg taatcccaac actttgggag gctgaagcag gcagattgct 109200
```

```
tgaggccagg agttcgagaa cagtctggcc aacatggcga aacctcatct ctactaaaat   109260
tacaaaaatt agccgggcat ggtggcacat gcctgtaatc ccagctacgt caggaggctg   109320
aggcacagga attgcttgaa cccaagaggc agaggatgca atgagccaag atcacaccac   109380
tgcactccag ccttggcgac agagggagac tctgtctcaa aaaaaaaaaa aaaaggtgtg   109440
cccaggcccc tagccattgc catgtgccca gccagagagc caaattagag ggctggcttc   109500
cctatcacac agaataaatg ctagtgctag ccaatgatcc ctttgctttt aatgtataga   109560
aaatactgtt gttccttttg tcatttccag tgacatctgt tttctaagca gctcttttct   109620
agggaggaaa ccaaagggggc taggttaaga ccctaataga aatgtttttt ctaatctctg   109680
gtgagtctgg aagtgtcaca ttcacagtcc acccttggga gtggcttggt ggagctgggg   109740
acaaggtttt gtttactaca tagtgcacat gataaatggc cttaaactgt gattcttttct   109800 ggtaggataa gttataataa actgaccccta aagaatgcaa t                    109841
```

<210> SEQ ID NO 2
<211> LENGTH: 7250
<212> TYPE: DNA
<213> ORGANISM: Homo sapiens

<400> SEQUENCE: 2

```
ccttggccga gaccggtcct ctgcggagag ggccccgccc tctgtgaagg cccgccgggg     60
aattggcggc ggcgctgcag ccatttccgg tttcggggag gtgggtgggg tgcggagcgg    120
gacttggagc agccgccgcc gctgccaccg cctacagagc ctgccttgcg cctggtgctg    180
ccaggaagat gcgccggag cccggaggct gctgctgccg ccgcacggtg cgggcgaatg    240
gctgcgtggc gaacggggaa gtacggaacg ggtacgtgag gagcagcgct gcagccgcag    300
ccgcagccgc cgccggccag atccatcatg ttacacaaaa tggaggacta tataaaagac    360
cgtttaatga agcttttgaa gaaacaccaa tgctggttgc tgtgctcacg tatgtggggt    420
atggcgtact caccctcttt ggatatcttc gagatttctt gaggtattgg agaattgaaa    480
agtgtcacca tgcaacagaa agagaagaac aaaaggactt tgtgtcattg tatcaagatt    540
ttgaaaactt ttatacaagg aatctgtaca tgaggataag agacaactgg aatcggccaa    600
tctgtagtgt gcctggagcc agggtggaca tcatggagag acagtctcat gattataact    660
ggtccttcaa gtacagggg aatataataa agggtgttat aaacatgggt tcctacaact    720
atcttggatt tgcacggaat actggatcat gtcaagaagc agccgccaaa gtccttgagg    780
agtatggagc tggagtgtgc agtactcggc aggaaattgg aaacctggac aagcatgaag    840
aactagagga gcttgtagca aggttcttag gagtagaagc tgctatggcg tatggcatgg    900
gatttgcaac gaattcaatg aacattcctg ctcttgttgg caaaggttgc ctgattctga    960
gtgatgaact gaatcatgca tcactggttc tgggagccag actgtcagga gcaaccatta   1020
gaatcttcaa acacaacaat atgcaaagcc tagagaagct attgaaagat gccattgttt   1080
atggtcagcc tcggacacga aggccctgga agaaaattct catccttgtg gaaggaatat   1140
atagcatgga gggatctatt gttcgtcttc ctgaagtgat tgccctcaag aagaaataca   1200
aggcatactt gtatctggat gaggctcaca gcattgcgc cctgggcccc acaggccggg   1260
gtgtggtgga gtactttggc ctggatcccg aggatgtgga tgttatgatg ggaacgttca   1320
caaagagttt tggtgcttct ggaggatata ttggaggcaa gaaggagctg atagactacc   1380
tgcgaacaca ttctcatagt gcagtgtatg ccacgtcatt gtcacctcct gtagtggagc   1440
agatcatcac ctccatgaag tgcatcatgg ggcaggatgg caccagcctt ggtaaagagt   1500
```

```
gtgtacaaca gttagctgaa aacaccaggt atttcaggag acgcctgaaa gagatgggct   1560
tcatcatcta tggaaatgaa gactctccag tagtgccttt gatgctctac atgcctgcca   1620
aaattggcgc ctttggacgg gagatgctga agcggaacat cggtgtcgtt gtggttggat   1680
ttcctgccac cccaattatt gagtccgagg ccaggttttg cctgtcagca gctcatacca   1740
aagaaatact tgatactgct ttaaaggaga tagatgaagt tggggaccta ttgcagctga   1800
agtattcccg tcatcggttg gtacctctac tggacaggcc ctttgacgag acgacgtatg   1860
aagaaacaga agactgagcc ttttggtgc tccctcagag gaactctccc tcacccagga   1920
cagcctgtgg cctttgtgag ccagttccag gaaccacact tctgtggcca tctcacgtga   1980
aagacattgc ctcagctact gaaggtggcc acctccactc taaatgacat tttgtaaata   2040
gtaaaaaact gcttctaatc cttcctttgc taaatctcac ctttaaaaac gaaggtgact   2100
cactttgctt tttcagtcca ttaaaaaaac attttatttt gcaaccattc tacttgtgaa   2160
atcacgctga ccctagcctg tctctggcta accacacagg ccattcccct ctcccagcac   2220
cttgcagact tgggcccatc aagagctact gctggccctg gctccgcagc ctggatactt   2280
acctggccct cctccctagg gagcaagtgc cttccactta cttcccatcc aggtctcaga   2340
ggtctcaagg ccaaccttgg aatccttatt taaccattca agtaatcaac ggaagttttc   2400
acccttaat cttaagttta gccttttaag aaaaacagta agcgatgact gctgaaaggc   2460
tcattgtgta atctcccaag ggtttggtct tattccattt tcttctggtc accagatgat   2520
ttcttccttt accatcaaat acttcttcat aatggtcaca gtctgaggat gtgcgcaaat   2580
tctggttctt cccaagctct aaccgtaaca cgtcccaccc ccttttttaaa gcacttactg   2640
ttttcagagc acccatatcc caccctggtg agaaggccac tctcacatct gagtgttggg   2700
tacaaagctg ctccgtagag tgatgtgcac tcctggtggg tgaggggcag gggcagtggc   2760
agtgtgcaaa gaattgatta ctccttgcag agcctgtggc ttgcatttcc tactgctttc   2820
tacgtttgaa aattatgaca gtctctggct aggtctgggt ccagattagg atttaaactg   2880
ataaaggaaa ctgttggtaa atcctctgct cagaaagcat ttatcatgtt cctatttaag   2940
gattaggttt attaatttag gcctcttaga agctaaccca cttaaatatt actcttctga   3000
atgctagttc tcttttattc ttgatgtcct aagtcaattg aatctggcat ctggggctag   3060
ggtctgcctg tctacatatt ttttattttt ttctgagaaa ttctgaacac atagatctct   3120
ttcctaaact gacattttct atttttgactg ttttcatact ataaccaggt aaagggactt   3180
ctttcagaga gctttatact gcctgaccaa agaacaaatc tgaaaatcac cattttaaag   3240
ttatttttc agttgaacca aagtttaagt gaagaggact tttggcatat tatacccagg   3300
atcagtttgt cttttgtat ccatcaagta ttacaggaga aggattggga acagaatgga   3360
aaaacagtgt atgaaagtca tgttacaggc cgagtgcggt ggctcacacc tgtaatccta   3420
gcactttggg aggctgaggc aggtggctca cttgaggtca ggaattcaag accagcctgg   3480
ccaacatggt gaaaccccgt ctctactaaa aagacaaaaa attagctggg cgtggtggcg   3540
ggcacctata atcccaccta cttggtaggc tgaggcagga gaatcgcttg aacccaggag   3600
gcggaggttg cagtgagacg agattgtgcc actgcactct agcctgggtg acagagcaaa   3660
actgtgtctc aaaaaaaaaa gtcatgttac acatttaagt ttttgaaatt gctccttta   3720
tcggtaaaga ttctcaatcc aaattctcct gggtgtgttg tcatcagctg tgatatgttt   3780
gtgcacatta cgtatagcag aggatgtaag caatattatt gtttgtgaag ttttgttttt   3840
```

```
aatgtcttga gtatgagtta tgtttagtca ctgtcagcat ctgagaactt taataagccc    3900
ttgagatatt ccaaagtttt attttacttt tttaaagaac agaaaaagat gaatgaaaga    3960
accaaggaga gatgcagaga ctatatttag catgtatagg ttaaagtaag aaggaggttg    4020
tggtaactaa ataggagtcc tataaaatca aatacattgt caaccttttc tgcacatcta    4080
gtttcctacc atagaatccc actggaatac acatagctt ttgcactgca gttactattt    4140
actaatgtaa acgtagggtt tgtaaaagtc acaaacttat aagcaatgaa cttacctgct    4200
agtcttttta ttttggcttg catgaagtca ctgcaaattc aaatgtcagt accggcattt    4260
aaaatatatc tatatcactt tgttggtaca agttatttc aagataagtg taattttgtt    4320
acaagtttat tttgaagaga caaatctcct gtgatctatg caggacctct gtactttcta    4380
aagaacaaaa tgttatgtag acattataca tggttggttg tctcttcttg aaactgtaat    4440
gtaaatctag ggtccagtca tatcctaggt atcatcattt atccaagtac ttggaggaat    4500
acaagtatat ataaatacag tcattgagaa taagtcgatt tgaggcatac aagagtagtt    4560
tcttacacag tttaacacgg cctgattcaa gactctgata ggattcaaac agataccggt    4620
taaccatgac taccaaaact gatcatctga gtcgattgat agaggtgtga ctagtcctta    4680
gcactttttc tcattcctct ttttattcag cattgctgtt acctatttca ggtttataag    4740
acctctttca gcagatcaca tcagaagcca ggaaatgcat agctaggaga tgtcaaaagc    4800
ccatatgagg agtggaccaa gcagcagtgg cggtttctcc tcgcatcttt ttttttttaa    4860
gctttaactt agcaggggca tggactttat agcacttttt caacttttg ctttgctttg     4920 gataagaaat ccttaccttt aaaaaagct tctagtctcc ataaccccca aagtactgct     4980
tatttgtttg aagaatccag ccatcgtagt gctttagtca ctatcgtaaa cattcatgat    5040
agggcaagga ttttaaaaca ggattcttgc ttctgtagtc atcaaggtga acagaagcat    5100
cctacacaac cactaagggc tctatgtttg tgtcatgcct cttcaaacac caaggagttg    5160
aacatgcttc cagtgatttg tctccgtaat gccttcttcc tttatttggc ctttcttct     5220 ttctgtacct tcaagttctt gattttaaa attccaactc tagagaaaac caatatatgg     5280
tggtgctggg ctttgaagat agcatatcag acgccttggt tctgtttgta cacttagcct    5340
tacatttcag gaggaggctt tcattaggg gcttaagcta gctccttttgg cttttaaaaa    5400 aaatttttt tcaaatttct tcattaccta agggagcctg catctaaatt tctcaactag    5460
ttcagcctag ctgaattttc tagtgtgtaa tacactttgc ttccttctta ttggtgaaaa    5520
ccagggggat gagtggcttc catggagaga tttcctgatt tctcagggag gaaaaaagtg    5580
atgacattta ccactacttt tatgtttttc ccctttttcc aaattgataa ggatttctgg    5640
ttcctagtga tccgggattg ggcaacagtg cagaactgcc agtcatgccg taggccgtga    5700
agaaagaatg tgagtaactg ttgttttgca aggatttgta gggttatggg cagttgttgt    5760
ttgaagcatt gctatgacct aattcccaag gtatctttcc tctcttggtg ttctaggtaa    5820
gccaatgagc tttaatctct acttgctata accgtgtgct tagaaaaaga ggtgagagta    5880 gtggtttttcc ttcaaactgt ccacattcat gaagattatg aattgttagg acagccaggg    5940
caagatagac cctgtctcta caaaaatttt tttctaaatt aaccgggcat ggtggtgcct    6000
gcctgtagtc ccacctgtgt gggagaatca cttgagcctg ggaggtcaag gctgcagtga    6060
gccatgattg caccctgca ctccagcctg ggtgacagag tgagaccctg gctcaataag     6120 aggggaaaa aaaattgtta ggagctgggt gcggatgcag cctgcaatcc cagctacttg     6180
agaggctgag gccggaggat tgcttaaacc caagaatttg agcgtagcct gggcaacaca    6240
```

```
gcaagacccc atctaagaaa aaaatgtttt ttaaatcagc ttagcccaaa ggggttgtga    6300
atggggaggt ataaaaagca aagattattt tttggctact aagccaagaa cttacaggga    6360 ttttttttt cagtcccaga acctacagat accctgctac ttgcttcacg tggatgctca    6420
gtgcccagca gccatcttaa tacattaaac cagtttaaaa ataccttcc atgtggagaa     6480 aaacatgtct ttttctcgcc tcaactttat ccacatgaaa tgtgtgccca tggctgggcg    6540
cagtggctca cctgtaatcc caacactttg ggaggctgaa gcaggcagat tgcttgaggc    6600
caggagttcg agaacagtct ggccaacatg gcgaaacctc atctctacta aaattacaaa    6660
aattagccgg gcatggtggc acatgcctgt aatcccagct acgtcaggag ctgaggcac    6720 aggaattgct tgaacccaag aggcagagga tgcaatgagc caagatcaca ccactgcact    6780
ccagccttgg cgacagaggg agactctgtc tcaaaaaaaa aaaaaaaagg tgtgcccagg    6840
cccctagcca ttgccatgtg cccagccaga gagccaaatt agagggctgg cttccctatc    6900
acacagaata aatgctagtg ctagccaatg atcccctttgc ttttaatgta tagaaaatac    6960
tgttgttcct tttgtcattt ccagtgacat ctgttttcta agcagctctt ttctagggag    7020
gaaaccaaag gggctaggtt aagaccctaa tagaaatgtt ttttctaatc tctggtgagt    7080
ctggaagtgt cacattcaca gtccaccctt gggagtggct tggtggagct ggggacaagg    7140
ttttgtttac tacatagtgc acatgataaa tggccttaaa ctgtgattct ttctggtagg    7200
ataagttata ataaactgac cctaaagaat gcaaaaaaaa aaaaaaaaa               7250
```

<210> SEQ ID NO 3
<211> LENGTH: 561
<212> TYPE: PRT
<213> ORGANISM: Homo sapiens

<400> SEQUENCE: 3

Met Arg Pro Glu Pro Gly Gly Cys Cys Cys Arg Arg Thr Val Arg Ala
1               5                   10                  15

Asn Gly Cys Val Ala Asn Gly Glu Val Arg Asn Gly Tyr Val Arg Ser
            20                  25                  30

Ser Ala Ala Ala Ala Ala Ala Ala Gly Gln Ile His His Val
        35                  40                  45

Thr Gln Asn Gly Gly Leu Tyr Lys Arg Pro Phe Asn Glu Ala Phe Glu
    50                  55                  60

Glu Thr Pro Met Leu Val Ala Val Leu Thr Tyr Val Gly Tyr Gly Val
65                  70                  75                  80

Leu Thr Leu Phe Gly Tyr Leu Arg Asp Phe Leu Arg Tyr Trp Arg Ile
                85                  90                  95

Glu Lys Cys His His Ala Thr Glu Arg Glu Glu Gln Lys Asp Phe Val
            100                 105                 110

Ser Leu Tyr Gln Asp Phe Glu Asn Phe Tyr Thr Arg Asn Leu Tyr Met
        115                 120                 125

Arg Ile Arg Asp Asn Trp Asn Arg Pro Ile Cys Ser Val Pro Gly Ala
    130                 135                 140

Arg Val Asp Ile Met Glu Arg Gln Ser His Asp Tyr Asn Trp Ser Phe
145                 150                 155                 160

Lys Tyr Thr Gly Asn Ile Ile Lys Gly Val Ile Asn Met Gly Ser Tyr
                165                 170                 175

Asn Tyr Leu Gly Phe Ala Arg Asn Thr Gly Ser Cys Gln Glu Ala Ala
            180                 185                 190

```
Ala Lys Val Leu Glu Glu Tyr Gly Ala Gly Val Cys Ser Thr Arg Gln
            195                 200                 205

Glu Ile Gly Asn Leu Asp Lys His Glu Leu Glu Glu Leu Val Ala
210                 215                 220

Arg Phe Leu Gly Val Glu Ala Ala Met Ala Tyr Gly Met Gly Phe Ala
225                 230                 235                 240

Thr Asn Ser Met Asn Ile Pro Ala Leu Val Gly Lys Gly Cys Leu Ile
                245                 250                 255

Leu Ser Asp Glu Leu Asn His Ala Ser Leu Val Leu Gly Ala Arg Leu
            260                 265                 270

Ser Gly Ala Thr Ile Arg Ile Phe Lys His Asn Asn Met Gln Ser Leu
        275                 280                 285

Glu Lys Leu Leu Lys Asp Ala Ile Val Tyr Gly Gln Pro Arg Thr Arg
290                 295                 300

Arg Pro Trp Lys Lys Ile Leu Ile Leu Val Glu Gly Ile Tyr Ser Met
305                 310                 315                 320

Glu Gly Ser Ile Val Arg Leu Pro Glu Val Ile Ala Leu Lys Lys Lys
                325                 330                 335

Tyr Lys Ala Tyr Leu Tyr Leu Asp Glu Ala His Ser Ile Gly Ala Leu
            340                 345                 350

Gly Pro Thr Gly Arg Gly Val Val Glu Tyr Phe Gly Leu Asp Pro Glu
        355                 360                 365

Asp Val Asp Val Met Met Gly Thr Phe Thr Lys Ser Phe Gly Ala Ser
370                 375                 380

Gly Gly Tyr Ile Gly Gly Lys Lys Glu Leu Ile Asp Tyr Leu Arg Thr
385                 390                 395                 400

His Ser His Ser Ala Val Tyr Ala Thr Ser Leu Ser Pro Pro Val Val
                405                 410                 415

Glu Gln Ile Ile Thr Ser Met Lys Cys Ile Met Gly Gln Asp Gly Thr
            420                 425                 430

Ser Leu Gly Lys Glu Cys Val Gln Gln Leu Ala Glu Asn Thr Arg Tyr
        435                 440                 445

Phe Arg Arg Arg Leu Lys Glu Met Gly Phe Ile Ile Tyr Gly Asn Glu
450                 455                 460

Asp Ser Pro Val Val Pro Leu Met Leu Tyr Met Pro Ala Lys Ile Gly
465                 470                 475                 480

Ala Phe Gly Arg Glu Met Leu Lys Arg Asn Ile Gly Val Val Val Val
                485                 490                 495

Gly Phe Pro Ala Thr Pro Ile Ile Glu Ser Arg Ala Arg Phe Cys Leu
            500                 505                 510

Ser Ala Ala His Thr Lys Glu Ile Leu Asp Thr Ala Leu Lys Glu Ile
        515                 520                 525

Asp Glu Val Gly Asp Leu Leu Gln Leu Lys Tyr Ser Arg His Arg Leu
530                 535                 540

Val Pro Leu Leu Asp Arg Pro Phe Asp Glu Thr Thr Tyr Glu Glu Thr
545                 550                 555                 560

Glu

<210> SEQ ID NO 4
<211> LENGTH: 53
<212> TYPE: DNA
<213> ORGANISM: Artificial Sequence
<220> FEATURE:
<223> OTHER INFORMATION: Primer
```

<400> SEQUENCE: 4
gggacaagtt tgtacaaaaa agcaggctat gcggccggag cccggaggct gct    53

<210> SEQ ID NO 5
<211> LENGTH: 53
<212> TYPE: DNA
<213> ORGANISM: Artificial Sequence
<220> FEATURE:
<223> OTHER INFORMATION: Primer

<400> SEQUENCE: 5
ggggaccact ttgtacaaga aagctgggtc cgtcttctgt ttcttcatac gtc    53

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ccacaggccg gggtatggtg gagtac    26

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gtactccacc atacccggc ctgtgg    26

<210> SEQ ID NO 8
<211> LENGTH: 43
<212> TYPE: DNA
<213> ORGANISM: Artificial Sequence
<220> FEATURE:
<223> OTHER INFORMATION: Primer

<400> SEQUENCE: 8
gaacgttcac aaagagtttt gttgcttctg gaggatatat tgg    43

<210> SEQ ID NO 9
<211> LENGTH: 43
<212> TYPE: DNA
<213> ORGANISM: Artificial Sequence
<220> FEATURE:
<223> OTHER INFORMATION: Primer

<400> SEQUENCE: 9
ccaatatatc ctccagaagc aacaaaactc tttgtgaacg ttc    43

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
ttcctgccac cccaattttt gagtccagag cc    32

<210> SEQ ID NO 11
<211> LENGTH: 32

```
<212> TYPE: DNA
<213> ORGANISM: Artificial Sequence
<220> FEATURE:
<223> OTHER INFORMATION: Primer

<400> SEQUENCE: 11
ggctctggac tcaaaaattg gggtggcagg aa                                    32

<210> SEQ ID NO 12
<211> LENGTH: 126
<212> TYPE: DNA
<213> ORGANISM: Artificial Sequence
<220> FEATURE:
<223> OTHER INFORMATION: Primer

<400> SEQUENCE: 12
gccactacct gagcccgttg tcagcgtagt ctgggacgtc gtatgggtaa gcgtagtctg      60
ggacgtcgta tgggtaagcg tagtctggga cgtcgtatgg gtagacaccc ctccttatta     120
catttc                                                               126

<210> SEQ ID NO 13
<211> LENGTH: 126
<212> TYPE: DNA
<213> ORGANISM: Artificial Sequence
<220> FEATURE:
<223> OTHER INFORMATION: Primer

<400> SEQUENCE: 13
gaaatgtaat aaggaggggt gtctacccat acgacgtccc agactacgct tacccatacg      60
acgtcccaga ctacgcttac ccatacgacg tcccagacta cgctgacaac gggctcaggt     120
agtggc                                                               126

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gcccaactgg tcgcggtatg tgtgaaatat ttggcg                                36

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
cgccaaatat ttcacacata ccgcgaccag ttgggc                                36

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
gtactttcac taagtcgttt gttgctgctg gtggttacat tg                         42

<210> SEQ ID NO 17
```

<211> LENGTH: 42
<212> TYPE: DNA
<213> ORGANISM: Artificial Sequence
<220> FEATURE:
<223> OTHER INFORMATION: Primer

<400> SEQUENCE: 17
caatgtaacc accagcagca acaaacgact tagtgaaagt ac        42

<210> SEQ ID NO 18
<211> LENGTH: 43
<212> TYPE: DNA
<213> ORGANISM: Artificial Sequence
<220> FEATURE:
<223> OTHER INFORMATION: Primer

<400> SEQUENCE: 18
cttatcctgc tactccgctg tttgaatcaa gagtaagatt ctg       43

<210> SEQ ID NO 19
<211> LENGTH: 43
<212> TYPE: DNA
<213> ORGANISM: Artificial Sequence
<220> FEATURE:
<223> OTHER INFORMATION: Primer

<400> SEQUENCE: 19
cagaatctta ctcttgattc aaacagcgga gtagcaggat aag       43

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
ctaatgggta ctttcactac ttcgtttggt gctgctggtg           40

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
caccagcagc accaaacgaa gtagtgaaag tacccattag           40

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gagtccagag ccaggttttg                                 20

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23

```
ctgagggagc accaaaaag                                             19

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
gagagggtta gggataggct tac                                        23

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
gcagccattt ccggtttc                                              18

<210> SEQ ID NO 26
<211> LENGTH: 18
<212> TYPE: DNA
<213> ORGANISM: Artificial Sequence
<220> FEATURE:
<223> OTHER INFORMATION: Primer

<400> SEQUENCE: 26
ggattgccca gcggatgg                                              18

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ttacaggtgt gagccagtgc                                            20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
tgtgcaaaaa tactaagatt tc                                         22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
cacaatcttg cacgtaatga aa                                         22

<210> SEQ ID NO 30
<211> LENGTH: 23
<212> TYPE: DNA
```

<213> ORGANISM: Artificial Sequence
<220> FEATURE:
<223> OTHER INFORMATION: Primer

<400> SEQUENCE: 30
cctcagctgc tactcctatt ttg                                          23

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
tctgcttcct tttgtgtcac c                                            21

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tcagaaaaac aaagcattct tca                                          23

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
agtctgaaaa ggacacaaca ca                                           22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
gctcactctg actgcttttc aa                                           22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tgatcactgt gctgttgtgc                                              20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
aagactggac cggaagaaca t                                            21

```
<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
tgaggcatgg tttctgaatg                                              20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tgctgactct gtttccaggt                                              20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
acttcagcct ggacaatgga                                              20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gagcctaaac cagaggcaaa                                              20

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gaccatgttg gttgaccttg t                                            21

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
gtccatggaa accacacacc                                              20

<210> SEQ ID NO 43
<211> LENGTH: 25
<212> TYPE: DNA
<213> ORGANISM: Artificial Sequence
<220> FEATURE:
```

<223> OTHER INFORMATION: Primer

<400> SEQUENCE: 43
aaatatttta tggtgaaatg gaaaa					25

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
tggcatatgt accaaatgaa gg					22

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gcctgcatca ccaaagagtt					20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
cactgtcacc ccctctgtct					20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
cctgccgaag gataatcttg					20

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
gcaaaggaag gattagaagc a					21

<210> SEQ ID NO 49
<211> LENGTH: 17
<212> TYPE: DNA
<213> ORGANISM: Artificial Sequence
<220> FEATURE:
<223> OTHER INFORMATION: Primer

<400> SEQUENCE: 49
caaacggtgc agagacc					17

```
<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
aacccttcat aagatgaact cta                                              23

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
taacaggaga atgctaacct t                                                21

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
cactttagag aggagtaggc                                                  20

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
agataacctt ctacctctgt tctaa                                            25

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
ttgtcatcta gtggccat                                                    18

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
gaatcgtgca taatcctgg                                                   19

<210> SEQ ID NO 56
<211> LENGTH: 19
<212> TYPE: DNA
<213> ORGANISM: Artificial Sequence
<220> FEATURE:
<223> OTHER INFORMATION: Primer
```

```
<400> SEQUENCE: 56
agagacagac acaaggaat                                               19

<210> SEQ ID NO 57
<211> LENGTH: 19
<212> TYPE: DNA
<213> ORGANISM: Artificial Sequence
<220> FEATURE:
<223> OTHER INFORMATION: Primer

<400> SEQUENCE: 57
aatcttggcc ttgttgaaa                                               19

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
tctaacaagg acctactcag a                                            21

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
ctgtccccac aagttgtttt                                              20

<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
gtcaccttga agagcagaa                                               19

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
tttaggtctg agtgtgaaca ta                                           22

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
tctgtttagc taggaaaggt ga                                           22

<210> SEQ ID NO 63
<211> LENGTH: 19
```

```
<212> TYPE: DNA
<213> ORGANISM: Artificial Sequence
<220> FEATURE:
<223> OTHER INFORMATION: Primer

<400> SEQUENCE: 63
ggagggtatt tgttagtta                                            19

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
ggtgtggtga actgaattg                                            19

<210> SEQ ID NO 65
<211> LENGTH: 19
<212> TYPE: DNA
<213> ORGANISM: Artificial Sequence
<220> FEATURE:
<223> OTHER INFORMATION: Primer

<400> SEQUENCE: 65
agggatggga ctagatgta                                            19

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gggagattaa tgaggcagaa                                           20

<210> SEQ ID NO 67
<211> LENGTH: 17
<212> TYPE: DNA
<213> ORGANISM: Artificial Sequence
<220> FEATURE:
<223> OTHER INFORMATION: Primer

<400> SEQUENCE: 67
atgcttgcca agttgac                                              17

<210> SEQ ID NO 68
<211> LENGTH: 19
<212> TYPE: DNA
<213> ORGANISM: Artificial Sequence
<220> FEATURE:
<223> OTHER INFORMATION: Primer

<400> SEQUENCE: 68
cataatctaa cgcctgtgc                                            19

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
```

```
catattcctt ttttgtcag                                                  19

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
taaataaccc aagagaaac                                                  19

<210> SEQ ID NO 71
<211> LENGTH: 19
<212> TYPE: DNA
<213> ORGANISM: Artificial Sequence
<220> FEATURE:
<223> OTHER INFORMATION: Primer

<400> SEQUENCE: 71
gctattaatc tgggctctg                                                  19

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
ggagaaatcc atttatattc cttg                                            24

<210> SEQ ID NO 73
<211> LENGTH: 50
<212> TYPE: PRT
<213> ORGANISM: Homo sapiens

<400> SEQUENCE: 73

Ser Ile Gly Ala Leu Gly Pro Thr Gly Arg Gly Val Val Glu Tyr Phe
1               5                   10                  15

Gly Leu Asp Pro Glu Asp Val Asp Val Met Met Gly Thr Phe Thr Lys
            20                  25                  30

Ser Phe Gly Ala Ser Gly Gly Tyr Ile Gly Gly Lys Lys Glu Leu Ile
        35                  40                  45

Asp Tyr
    50

<210> SEQ ID NO 74
<211> LENGTH: 50
<212> TYPE: PRT
<213> ORGANISM: Bos taurus

<400> SEQUENCE: 74

Ser Ile Gly Ala Leu Gly Pro Thr Gly Arg Gly Val Val Asp Tyr Phe
1               5                   10                  15

Gly Leu Asp Pro Glu Asp Val Asp Ile Met Met Gly Thr Phe Thr Lys
            20                  25                  30

Ser Phe Gly Ala Ser Gly Gly Tyr Ile Gly Gly Lys Lys Ala Leu Ile
        35                  40                  45

Asp Tyr
    50
```

-continued

<210> SEQ ID NO 75
<211> LENGTH: 50
<212> TYPE: PRT
<213> ORGANISM: Rattus norvegicus

<400> SEQUENCE: 75

Ser Ile Gly Ala Leu Gly Pro Ser Gly Arg Gly Val Val Asp Tyr Phe
1               5                   10                  15

Gly Leu Asp Pro Glu Asp Val Asp Val Met Met Gly Thr Phe Thr Lys
            20                  25                  30

Ser Phe Gly Ala Ser Gly Gly Tyr Ile Gly Gly Lys Lys Glu Leu Ile
        35                  40                  45

Asp Tyr
    50

<210> SEQ ID NO 76
<211> LENGTH: 50
<212> TYPE: PRT
<213> ORGANISM: Mus musculus

<400> SEQUENCE: 76

Ser Ile Gly Ala Leu Gly Pro Ser Gly Arg Gly Val Val Asp Tyr Phe
1               5                   10                  15

Gly Leu Asp Pro Glu Asp Val Asp Val Met Met Gly Thr Phe Thr Lys
            20                  25                  30

Ser Phe Gly Ala Ser Gly Gly Tyr Ile Gly Gly Lys Lys Glu Leu Ile
        35                  40                  45

Asp Tyr
    50

<210> SEQ ID NO 77
<211> LENGTH: 50
<212> TYPE: PRT
<213> ORGANISM: Danio rerio

<400> SEQUENCE: 77

Ser Ile Gly Ala Leu Gly Pro Gly Gly Arg Gly Val Val Glu Tyr Phe
1               5                   10                  15

Gly Leu Asp Pro Arg Asp Val Asp Ile Met Met Gly Thr Phe Thr Lys
            20                  25                  30

Ser Phe Gly Ala Ala Gly Gly Tyr Ile Gly Gly Arg Lys Asp Leu Ile
        35                  40                  45

Asp Tyr
    50

<210> SEQ ID NO 78
<211> LENGTH: 50
<212> TYPE: PRT
<213> ORGANISM: Drosophila melanogaster

<400> SEQUENCE: 78

Ser Val Gly Ala Met Gly Ser Arg Gly Arg Gly Val Thr Asp Tyr Phe
1               5                   10                  15

Asn Val Asp Pro Lys Glu Val Asp Ile Leu Met Gly Thr Phe Thr Lys
            20                  25                  30

Ser Phe Gly Ser Ala Gly Gly Tyr Leu Ala Gly Ser Lys Lys Leu Ile
        35                  40                  45

Asp Phe
    50

<210> SEQ ID NO 79
<211> LENGTH: 50
<212> TYPE: PRT
<213> ORGANISM: Saccharomyces cerevisiae

<400> SEQUENCE: 79

Ser Ile Gly Ala Met Gly Pro Thr Gly Arg Gly Val Cys Glu Ile Phe
1               5                   10                  15

Gly Val Asp Pro Lys Asp Val Asp Ile Leu Met Gly Thr Phe Thr Lys
            20                  25                  30

Ser Phe Gly Ala Ala Gly Gly Tyr Ile Ala Ala Asp Gln Trp Ile Ile
        35                  40                  45

Asp Arg
    50

<210> SEQ ID NO 80
<211> LENGTH: 49
<212> TYPE: PRT
<213> ORGANISM: Sphingomonas paucimobilis

<400> SEQUENCE: 80

Ser Met Gly Phe Phe Gly Pro Asn Gly Arg Gly Val Tyr Glu Ala Gln
1               5                   10                  15

Gly Leu Glu Gly Gln Ile Asp Phe Val Val Gly Thr Phe Ser Lys Ser
            20                  25                  30

Val Gly Thr Val Gly Gly Phe Val Val Ser Asn His Pro Lys Phe Glu
        35                  40                  45

Ala

<210> SEQ ID NO 81
<211> LENGTH: 43
<212> TYPE: PRT
<213> ORGANISM: Homo sapiens

<400> SEQUENCE: 81

Gly Phe Pro Ala Thr Pro Ile Ile Glu Ser Arg Ala Arg Phe Cys Leu
1               5                   10                  15

Ser Ala Ala His Thr Lys Glu Ile Leu Asp Thr Ala Leu Lys Glu Ile
            20                  25                  30

Asp Glu Val Gly Asp Leu Leu Gln Leu Lys Tyr
        35                  40

<210> SEQ ID NO 82
<211> LENGTH: 43
<212> TYPE: PRT
<213> ORGANISM: Bos taurus

<400> SEQUENCE: 82

Gly Phe Pro Ala Thr Pro Ile Ile Glu Ser Arg Ala Arg Phe Cys Leu
1               5                   10                  15

Ser Ala Ala His Thr Arg Glu Thr Leu Asp Thr Ala Leu Lys Glu Ile
            20                  25                  30

Asp Glu Val Gly Asp Leu Leu His Leu Lys Tyr
        35                  40

<210> SEQ ID NO 83
<211> LENGTH: 43
<212> TYPE: PRT
<213> ORGANISM: Rattus norvegicus -continued

<400> SEQUENCE: 83

Gly Phe Pro Ala Thr Pro Ile Ile Glu Ser Arg Ala Arg Phe Cys Leu
1               5                   10                  15

Ser Ala Ala His Thr Lys Glu Ile Leu Asp Thr Ala Leu Lys Glu Ile
            20                  25                  30

Asp Glu Val Gly Asp Leu Leu Gln Leu Lys Tyr
        35                  40

<210> SEQ ID NO 84
<211> LENGTH: 43
<212> TYPE: PRT
<213> ORGANISM: Mus musculus

<400> SEQUENCE: 84

Gly Phe Pro Ala Thr Pro Ile Ile Glu Ser Arg Ala Arg Phe Cys Leu
1               5                   10                  15

Ser Ala Ala His Thr Lys Glu Ile Leu Asp Thr Ala Leu Lys Glu Ile
            20                  25                  30

Asp Glu Val Gly Asp Leu Leu Gln Leu Lys Tyr
        35                  40

<210> SEQ ID NO 85
<211> LENGTH: 43
<212> TYPE: PRT
<213> ORGANISM: Danio rerio

<400> SEQUENCE: 85

Gly Phe Pro Ala Thr Pro Ile Ile Glu Ser Arg Ala Arg Phe Cys Ile
1               5                   10                  15

Ser Ala Ala His Ser Lys Glu Met Leu Asp Arg Ala Leu Asp Val Ile
            20                  25                  30

Ser Glu Val Gly Asp Leu Leu Gln Leu Lys Tyr
        35                  40

<210> SEQ ID NO 86
<211> LENGTH: 43
<212> TYPE: PRT
<213> ORGANISM: Drosophila melanogaster

<400> SEQUENCE: 86

Gly Phe Pro Ala Thr Pro Ile Met Glu Gly Arg Ile Arg Phe Cys Leu
1               5                   10                  15

Ser Ala Ala His Thr Lys Glu Gln Leu Asp Phe Ala Leu Glu Ala Ile
            20                  25                  30

Asp Glu Ile Ala Asp Asp Leu Gly Leu Lys Tyr
        35                  40

<210> SEQ ID NO 87
<211> LENGTH: 50
<212> TYPE: PRT
<213> ORGANISM: Saccharomyces cerevisiae

<400> SEQUENCE: 87

Ala Tyr Pro Ala Thr Pro Leu Ile Glu Ser Arg Val Arg Phe Cys Met
1               5                   10                  15

Ser Ala Ser Leu Thr Lys Glu Asp Ile Asp Tyr Leu Leu Arg His Val
            20                  25                  30

Ser Glu Val Gly Asp Lys Leu Asn Leu Lys Ser Asn Ser Gly Lys Ser
        35                  40                  45

```
<210> SEQ ID NO 88
<211> LENGTH: 43
<212> TYPE: PRT
<213> ORGANISM: Sphingomonas paucimobilis

<400> SEQUENCE: 88

Arg Pro Pro Ala Thr Pro Ala Gly Thr Phe Leu Leu Arg Cys Ser Ile
1               5                   10                  15
Cys Ala Glu His Thr Pro Ala Gln Ile Gln Thr Val Leu Gly Met Phe
                20                  25                  30
Gln Ala Ala Gly Arg Ala Val Gly Val Ile Gly
            35                  40
```